(12) United States Patent
Zhang et al.

(10) Patent No.: US 10,597,399 B2
(45) Date of Patent: Mar. 24, 2020

(54) SUBSTITUTED TRIAZOLOPIPERAZINE PARP INHIBITOR, PREPARATION METHOD THEREFOR AND USE THEREOF

(71) Applicants: Ao Zhang, Shanghai (CN); Zehong Miao, Shanghai (CN); Pingyuan Wang, Shanghai (CN); Shanshan Song, Shanghai (CN); Zilan Song, Shanghai (CN); Xiajuan Huan, Shanghai (CN); Zhoulong Fan, Shanghai (CN); Jian Ding, Shanghai (CN)

(72) Inventors: Ao Zhang, Shanghai (CN); Zehong Miao, Shanghai (CN); Pingyuan Wang, Shanghai (CN); Shanshan Song, Shanghai (CN); Zilan Song, Shanghai (CN); Xiajuan Huan, Shanghai (CN); Zhoulong Fan, Shanghai (CN); Jian Ding, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/987,458

(22) Filed: May 23, 2018

(65) Prior Publication Data
US 2018/0265516 A1     Sep. 20, 2018

Related U.S. Application Data

(63) Continuation of application No. PCT/CN2016/106707, filed on Nov. 22, 2016.

(30) Foreign Application Priority Data

Nov. 23, 2015  (CN) .......................... 2015 1 0818057

(51) Int. Cl.
| | | |
|---|---|---|
| C07D 487/04 | (2006.01) | |
| A61K 31/444 | (2006.01) | |
| A61K 31/437 | (2006.01) | |
| A61K 31/502 | (2006.01) | |
| C07D 471/04 | (2006.01) | |
| A61K 31/4985 | (2006.01) | |
| A61P 35/00 | (2006.01) | |

(52) U.S. Cl.
CPC .......... *C07D 487/04* (2013.01); *A61K 31/437* (2013.01); *A61K 31/444* (2013.01); *A61K 31/4985* (2013.01); *A61K 31/502* (2013.01); *A61P 35/00* (2018.01); *C07D 471/04* (2013.01)

(58) Field of Classification Search
CPC .................................................. C07D 487/04
See application file for complete search history.

(56) References Cited

FOREIGN PATENT DOCUMENTS

| | | |
|---|---|---|
| CN | 101501006 A | 8/2009 |
| CN | 102731416 A | 10/2012 |
| CN | 102898377 A | 1/2013 |
| CN | 103570725 A | 2/2014 |
| JP | 2009538896 A | 11/2009 |
| JP | 2009538897 A | 11/2009 |
| JP | 2015527336 A | 9/2015 |
| WO | WO 2007/138351 A2 | 12/2007 |
| WO | WO 2007/138351 A3 | 12/2007 |
| WO | WO 2012/019427 A1 | 2/2012 |
| WO | WO 2014/019468 A1 | 2/2014 |

OTHER PUBLICATIONS

Menear et al., "4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1", KuDOS Pharmaceuticals Ltd., Journal of Med. Chemical, Sep. 19, 2008, pp. 6581-6591.

Kim et al., "Discovery of Potent and Selective Dipeptidyl Peptidase IV Inhibitors Derived from β-Aminoannides Bearing Subsituted Triazolopiperazines", Merck Research Laboratories, Journal of Med. Chemical, Jan. 18, 2008, pp. 589-602.

Kumar et al., "An expeditious synthesis of 1-aryl-4-methyl-1,2,4-triazolo[4,3-a]quinoxalines under solvent-free conditions using iodobenzene diacetate", Department of Chemistry, Birla Institute of Technology and Science, The Royal Society of Chemistry Journal, Jan. 27, 2004, pp. 156-157.

(Continued)

*Primary Examiner* — Brian E McDowell
(74) *Attorney, Agent, or Firm* — Reinhart Boerner Van Deuren P.C.

(57) ABSTRACT

A class of substituted triazolopiperazine compounds represented by formula (I), tautomers, enantiomers, diastereomers, racemates, metabolites, metabolic precursors, and pharmaceutically acceptable salts, esters, prodrugs or hydrate thereof, a preparation methods therefor, intermediates and a use thereof in the preparation of drugs for prevention and treatment of diseases associated with PARP including various ischemic diseases, neurodegenerative diseases and cancers.

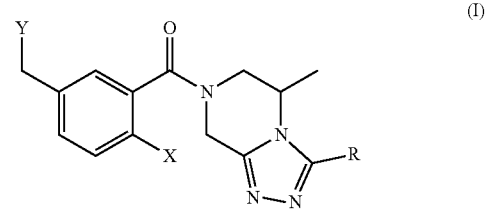

(I)

9 Claims, 2 Drawing Sheets

(56) References Cited

OTHER PUBLICATIONS

Menear et al., "Novel alkoxybenzamide inhibitors of poly(ADP-ribose) polymerase", KuDOS Pharmaceuticals Ltd, Bioorganic & Medicinal Chemistry Letters 18, Jun. 12, 2008, pp. 3942-3945.
Ferrigno et al., "Development of substituted 6-[4-fluoro-3-(piperazin-1-ylcarbonyl)benzyl]-4,5-dimethylpyridazin-3(2H)-ones as potent poly(ADP-ribose) polymerase-1 (PARP-1) inhibitors active in BRCA deficient cells", IRBM, Merck Research Laboratories Rome, Bioorganic & Medicinal Chemistry Letters 20, Nov. 22, 2009, pp. 1100-1105.

SUBSTITUTED TRIAZOLOPIPERAZINE PARP INHIBITOR, PREPARATION METHOD THEREFOR AND USE THEREOF

CROSS-REFERENCE TO RELATED PATENT APPLICATIONS

This patent application is a continuation of PCT/CN2016/106707, filed Nov. 22, 2016, which claims priority to Chinese Application No. 201510818057.7, filed Nov. 23, 2015, the entire teachings and disclosure of which are incorporated herein by reference thereto.

TECHNICAL FIELD

The present invention relates to a class of novel compounds as PARP inhibitors having substituted triazolopiperazine structure represented by the following formula (I), stereoisomers, a preparation method, intermediates of the same and a use thereof in the preparation of drugs for prevention and treatment of diseases associated with PARP including various ischemic diseases, neurodegenerative diseases, and cancers.

BACKGROUND

1. PARP Family and Structural Characteristics

It has been more than 50 years since the poly(ADP-ribose) polymerase (PARP) was firstly observed by Chambon and coworkers thereof in 1963, and PARP has attracted the attention of many researchers because of the applications in the repair of damage and maintenance of genome stability. Out of PARP family of enzymes, PARP-1 is the first found and extensively studied enzyme with the most typical structure. PARP-1 plays a key role in DNA repair, apoptosis, proliferation, etc., which is regarded as "the guardian angel of DNA". The poly(ADP-ribose) polymerase (PARP) is present in eukaryotes, catalyzes nicotinamide adenine dinucleotide (NAD$^+$) to release ADP-ribose, and further catalyze ADP-ribose to polymerize at the specific sites of various important proteins including PARP itself to form polymeric adenosine diphosphate ribose (poly (ADP-ribose) or PAR), thereby regulating the function of the protein and playing key roles during the repair of the single-strand DNA breaks.

PARP constitutes a family of cellular ribozyme proteins that catalyze the synthesis of poly(ADP-ribose). So far, 18 members in this family have been isolated and identified including: PARP-1, PARP-2, PARP-3, vPARP (PARP-4), Tankyrase-1 (PARP-5), Tankyrase-2 (PARP-5b), PARP-6, tiPARP (PARP-7), PARP-8, PARP-10, PARP-11, PARP-12, ZAP (PARP-13), BAL-1 (PARP-9), BAL-2 (PARP-14), BAL-3 (PARP-15), PARP-16, PARG. Among them, PARP-1 is the earliest discovered and the most well-known member of the PARP family, and the activity thereof accounts to more than 90% of the total cellular PARP activity. It is a polypeptide chain composed of 1014 amino acids having a molecular weight of 116 kDa. including three main functional domains: N-terminal DNA binding domain (DBD), auto-modification domain (AMD), and C-terminal catalytic domain. The DNA binding domain (DBD) contains two zinc-finger (referred as ZnF1 and ZnF2 below) motifs and a nuclear localization sequence. These two zinc-finger motifs are involved in the recognition of DNA nicks. The ZnF1 recognizes single-strand DNA damage and double-strand DNA damage, and its mutation can significantly reduce the activity of the PARP; the ZnF2 can only participate in the recognition of the single-strand DNA damage. The auto-modification domain of PARP-1 contains 15 glutamate residues as targets for ADP ribosylation itself, which is the main regulatory site. The C-terminal catalytic domain is the basis for the conversion of NAD$^+$ to ADP ribose.

In the PARP family, PARP-1 and PARP-2 share the highest homology (up to 69%). Therefore, all reported PARP-1 inhibitors have considerable inhibitory activity against PARP-2 till now.

2. PARP and Disease Treatment

The DNA damages are repaired mainly via base excision repair (BER) or homologous recombination (HR) repair under normal conditions. PARP and BRCA are the major enzymes involved in base excision repair and homologous recombination repair, respectively. For most of the ovarian cancer and triple negative breast cancer patients, two hypotypes BRCA1 and BRCA2 of BRCA usually have mutation, resulting in the loss of DNA damage repair ability, thus cell repair is mainly performed through base excision repair in which PARP enzymes are involved. Cancers could be treated effectively if the function of PARP enzyme to repair DNA damage is blocked, which results in apoptosis.

According to statistics, the prevalence of BRCA1 mutations was 45% for families with multiple cases of breast cancer, and was 90% for families with high incident breast and ovarian cancers. BRCA1 mutations have also been described in sporadic breast cancer cases. In addition, BRCA1/2 mutations are also found in other solid tumors such as ovarian cancer.

In 2005, Bryant and Framer respectively reported that using PARP inhibitors in cells lacking BRCA1/2-mediated homologous recombination repair function, thereby inhibiting PARP-mediated base excision repair (BER) pathways, ultimately causing synergistic lethality of tumor cells. This indicates that PARP inhibitors may be employed alone for the treatment of certain tumors. The results of this study quickly attracted wide attention from pharmaceutical companies and academia. Therefore, new era was opened for the development of PARP inhibitors as highly selective antitumor drugs. Recently, PARP-1 has been identified as a potential therapeutic target for the study of antitumor drugs.

3. PARP Inhibitors

It has been reported by Armin et. al. that the catalytic active sites of PARP-1 can be roughly divided into two domains, donor domain and acceptor domain, both using PARP substrate NAD$^+$ as a scaffold. Acceptor domain binds to ADP of polymeric adenosine diphosphate ribose chains. Donor domain binds to NAD$^+$, and this site can be further divided into three sub-binding domains: nicotinamide-ribose binding site (NI site), phosphate binding site (PH site), and adenosine-ribose binding site (AD site), respectively. Most of the PARP inhibitors interact with the NI site of PARP and competitively inhibit NAD$^+$. Therefore, their structures are similar to nicotinamide. For example, AZD2281 (olaparib/KU-59436) developed by AstraZeneca is an oral small molecule PARP inhibitor, which has shown promising therapeutical effects in treating ovarian cancer, breast cancer and solid tumor in combination with drugs such as cisplatin, carboplatin, paclitaxel and so on. Currently, AZD2281 is on the market.

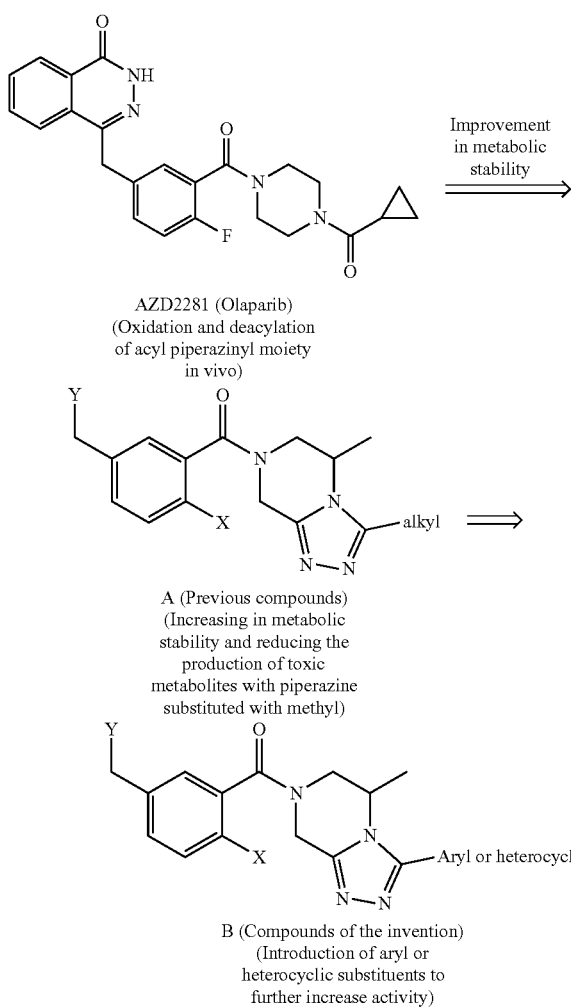

However, the compound AZD2281 showed weak selectivity and inhibitory activity against PARP-1. The effective dose of the inhibitory activity at the cellular level was 200 nM, and the in vivo dose above 100 mg just showed significant anti-tumor activity. The clinical daily dose is also up to 400 mg (50 mg capsules, 8 capsules). The in vivo action time and half-life time of compound AZD2281 are relatively short (<1 hours), and its bioavailability is also low (<15%). The metabolites of the compound AZD2281 mainly result from the oxidation and deacylation of piperazinyl moiety in the hydrophilic region of the molecule.

Therefore, the structurally stable piperazinotriazine moiety A was introduced in the previous stage by the inventor's team. With optimization of substituent on the piperazine ring, the introduction of methyl group is found to effectively improve the stability of the piperazine substituent moiety and reduce the production of toxic products (CN 103570725 A). Consequently, the triazine fragment was further optimized in the present invention based on the mode of action of PARP enzyme and small molecule, and the derivative B substituted by aryl, heteroaryl, or heterocycloalkyl was found to have relatively high activity.

BRIEF SUMMARY

One object of the present invention is to provide a class of substituted triazolopiperazine compounds represented by formula (I), or tautomers, enantiomers, diastereomers, racemates, metabolites, metabolic precursors, pharmaceutically acceptable salts, esters, prodrugs or hydrates thereof.

Another object of the present invention is to provide a method for preparing the substituted triazolopiperazine compounds as described above.

Another object of the present invention is to provide key intermediates of these compounds.

Another object of the present invention is to provide compounds represented by formula (I) and their stereoisomers.

Another object of the present invention is to provide a use of the compounds in the preparation of medicament for the prevention and treatment of diseases associated with PARP.

Diseases associated with PARP include various ischemic diseases (brain ischemia, ischemic disease of spinal cord, ischemic heart disease, ischemic disease of digestive tube, retinal ischemic disease etc.), neurodegenerative diseases (Parkinson's disease, Alzheimer's disease, muscular dystrophy etc.) and cancers (breast cancer, ovary cancer, liver cancer, melanoma, prostate cancer, colon cancer, gastric cancer, and other solid tumors)

The present invention provides a substituted triazolopiperazine compound represented by following formula (I), tautomers, enantiomers, diastereomers, racemates, metabolites, metabolic precursors, pharmaceutically acceptable salts, ester, prodrugs or hydrates thereof:

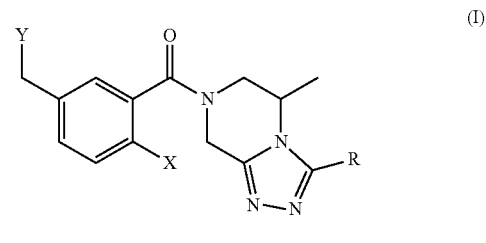

wherein,
Y is

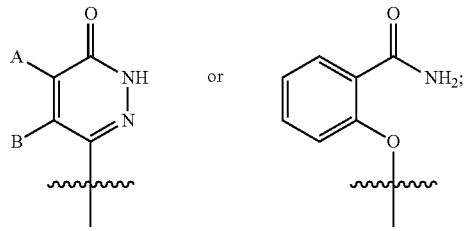

A and B are each independently hydrogen or substituted or unsubstituted C1-C8 alkyl, wherein the substituent in the substituted C1-C8 alkyl is selected from one or more of the group consisting of halogen, cyano, nitro, hydroxyl and amino;

alternatively, A and B together with the carbon atoms to which they are attached form a substituted or unsubstituted C4-C8 aliphatic ring, a substituted or unsubstituted C6-C10 aromatic ring, a substituted or unsubstituted 4-8 membered heterocyclic ring containing 1-3 heteroatoms selected from N, O and S, or a substituted or unsubstituted 5-8 membered heteroaromatic ring containing 1-3 heteroatoms selected from N, O, and S; wherein the substituent in the substituted rings is selected from one or more of the group consisting of halogen, cyano, nitro, hydroxyl, and amino;

X is hydrogen, halogen, hydroxyl, or cyano;

R is halogen, $COOR^1$, a substituted or unsubstituted heterocyclic ring, a substituted or unsubstituted heteroaromatic ring, a substituted or unsubstituted aromatic ring, wherein the substituent in the substituted heterocyclic ring, heteroaromatic ring or aromatic ring is selected from one or more of the group consisting of substituted or unsubstituted C1-C8 alkyl, halogen, cyano, nitro, hydroxyl, amino, C1-C6 alkoxy, C2-C6 alkylcarbonyl, C2-C6 alkoxycarbonyl, C2-C6 alkenyl, C2-C6 alkynyl, and C6-C10 aryl, wherein the substituent in the substituted C1-C8 alkyl is selected from one or more of the group consisting of halogen, cyano, nitro, hydroxyl, amino;

$R^1$ is selected from the group consisting of hydrogen, C1-C8 alkyl, substituted or unsubstituted aryl, or substituted or unsubstituted heterocyclyl, wherein the substituent in the substituted aryl or heterocyclyl is selected from one or more of the group consisting of C1-C8 alkyl, halogen, cyano, nitro, hydroxyl, amino, C1-C6 alkoxy, C2-C6 alkylcarbonyl, C2-C6 alkoxycarbonyl, C2-C6 alkenyl, C2-C6 alkynyl, and C6-C10 aryl.

Further preferably, in the compound of formula (I), Y is

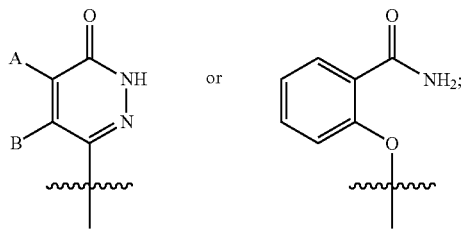

A and B are each independently hydrogen or C1-C4 alkyl;

alternatively, A and B together with the carbon atoms to which they are attached form a substituted or unsubstituted C4-C6 aliphatic ring or a substituted or unsubstituted C6-C8 aromatic ring, wherein the substituent in the substituted rings is selected from one or more of the group consisting of halogen, cyano, nitro, hydroxyl, and amino;

X is hydrogen, halogen, hydroxyl, or cyano;

R is halogen, $COOR^1$, a substituted or unsubstituted heterocyclic ring, a substituted or unsubstituted heteroaromatic ring, a substituted or unsubstituted aromatic ring, wherein the substituent in the substituted heterocyclic ring, heteroaromatic ring, or aromatic ring is selected from one or more of the group consisting of substituted or unsubstituted C1-C4 alkyl, halogen, cyano, nitro, hydroxyl, amino, C1-C4 alkoxy, C2-C4 alkylcarbonyl, C2-C4 alkoxycarbonyl, C2-C4 alkenyl, C2-C4 alkynyl and phenyl, wherein the substituent in the substituted C1-C4 alkyl is selected from one or more of the group consisting of halogen, cyano, nitro, hydroxyl, amino;

$R^1$ is selected from the group consisting of hydrogen, C1-C4 alkyl, substituted or unsubstituted aryl, or substituted or unsubstituted heterocyclyl, wherein the substituent in the substituted aryl or heterocyclyl is selected from one or more of the group consisting of C1-C4 alkyl, halogen, cyano, nitro, hydroxy, amino, C1-C4 alkoxy, C2-C4 alkylcarbonyl, C2-C4 alkoxycarbonyl, C2-C4 alkenyl, C2-C4 alkynyl and phenyl.

Specifically preferably, in the compound of formula (I), Y is

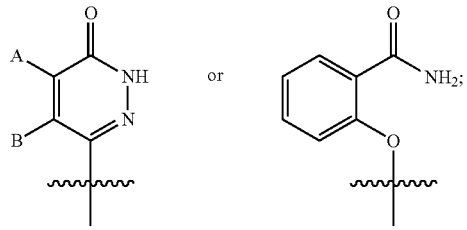

A and B are each independently hydrogen or methyl;

alternatively, A and B together with the carbon atoms to which they are attached form a benzene ring;

X is hydrogen or halogen;

R is halogen, $COOR^1$, substituted or unsubstituted phenyl, substituted or unsubstituted 5- and 6-membered heterocyclic ring, substituted or unsubstituted 5- and 6-membered heteroaromatic ring, wherein the substituent in the substituted phenyl, heterocyclic ring or heteroaromatic ring is selected from one or more of the group consisting of methyl, halogen, trifluoromethyl, methoxy, hydroxymethyl;

$R^1$ is selected from hydrogen, methyl and ethyl.

In the present invention, the halogen includes fluorine, chlorine, bromine, iodine; The alkyl group is preferably C1-C8 aliphatic alkyl groups, which may be linear alkyl, branched alkyl, spirocycloalkyl, fused cycloalkyl, bridged cycloalkyl, alkenylalkyl, alkynylalkyl, cycloalkyl, cycloalkenyl, cycloalkynyl, alkoxyalkyl, alkoxyacylalkyl, cycloalkylalkyl. Examples of the alkyl groups include but not limited to methyl, ethyl, n-propyl, isopropyl, n-butyl, isobutyl, tert-butyl, cyclopropyl, cyclobutanyl, cyclopentyl, cyclohexyl, allyl, propargyl, cyclobutenyl, cyclohexenyl;

The alkenyl refers to alkenyl having 2-10 carbon atoms, such as vinyl, propenyl, butenyl, styryl, cinnamyl;

The alkynyl refers to alkynyl having 2-10 carbon atoms, such as ethynyl, propynyl, butynyl, phenylethynyl, phenylpropargyl;

The cycloalkyl refers to saturated or partially unsaturated monocyclic or polycyclic cyclic hydrocarbon group having 3 to 20 carbon atoms, preferably 3 to 12 carbon atoms, more preferably cycloalkyl having 3 to 10 carbon atoms. Examples of monocyclic cycloalkyl include, but not limited to, cyclopropyl, cyclobutyl, cyclopentenyl, cyclohexyl, and cyclooctyl. Examples of polycyclic cycloalkyl include spirocycloalkyl, fused cycloalkyl, and bridged cycloalkyl.

The said spirocycloalkyl refers to a 5 to 20 membered polycyclic group in which the monocyclic rings share a common carbon atom (called as spiro atom) therebetween, one or more double bonds may be contained therein, but there is no rings having a completely conjugated π-electron system. The spirocycloalkyl is preferably 6 to 14 members, more preferably 7 to 10 members. According to the number of the common spiro atom, the spirocycloalkyl is divided into monospirocycloalkyl, dispirocycloalkyl or polyspirocycloalkyl. The spirocycloalkyl preferably refers to monospirocycloalkyl and dispirocycloalkyl, more preferably 4-membered/4-membered, 4-membered/5-membered, 4-membered/6-membered, 5-membered/5-membered, or 5-membered/6-membered monospirocycloalkyl. Representative examples of spirocycloalkyl include, but are not limited to the following groups:

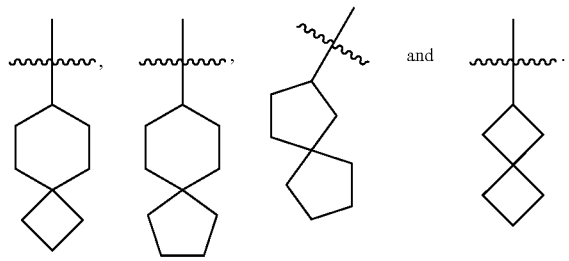

The said fused cycloalkyl refers to a 5 to 20 membered full-carbon polycyclic group, wherein each ring in the group shares an adjacent pair of carbon atoms with another ring in the group, one or more double bonds may be included in one or more rings, but there is no rings having a completely conjugated π-electron system. The preferred fused cycloalkyl is 6 to 14 membered, especially 7 to 10 membered. According to the number of the ring, fused cycloalkyl can be divided into fused bicyclic alkyl, fused tricyclic alkyl, fused tetracyclic alkyl or fused polycyclic alkyl. The fused cycloalkyl is preferably fused bicyclic alkyl or fused tricyclic alkyl, and more preferably 5-membered/5-membered bicyclic alkyl or 5-membered/6-membered bicyclic alkyl. Representative examples of fused cycloalkyl include, but are not limited to the following groups:

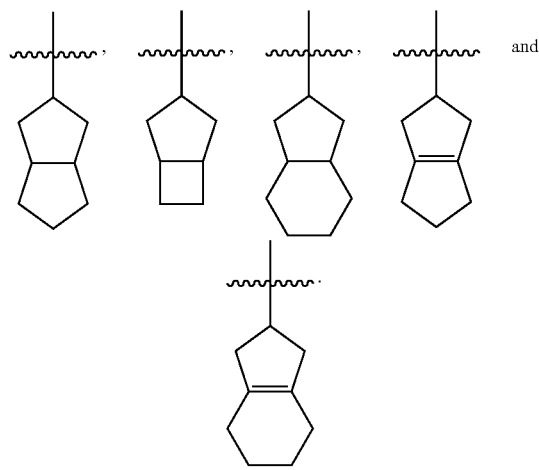

The said bridged cycloalkyl refers to a 5 to 20 membered full-carbon polycyclic group, in which any two rings share two disconnected carbon atoms, one or more double bonds may be contained therein, but there is no rings having a completely conjugated π-electron system. The bridged cycloalkyl is preferably 6 to 14 membered, more preferably 7 to 10 membered. According to the number of rings, bridged cycloalkyl is divided into bicyclic bridged cycloalkyl, tricyclic bridged cycloalkyl, tetracyclic bridged cycloalkyl, or polycyclic bridged cycloalkyl. The preferred bridged cycloalkyl is bicyclic bridged cycloalkyl, tricyclic bridged cycloalkyl, or tetracyclic bridged cycloalkyl, and especially bicyclic bridged cycloalkyl or tricyclic bridged cycloalkyl.

The heterocyclic ring group refers to a 3 to 12 membered saturated or partially saturated monocyclic or polycyclic hydrocarbon group, such as saturated or unsaturated monocyclic heterocyclyl, fused heterocyclyl, spiro heterocyclyl, bridged heterocyclyl, which has one or more heteroatoms (nitrogen, oxygen, sulfur). The heterocyclic ring group includes, but is not limited to morpholinyl, piperidyl, piperazinyl, piperazinyl substituted by N-alkyl or acyl, homopiperazinyl, homopiperazinyl substituted by N-alkyl or acyl, pyrroyl, pyrrolidyl, 7H-purinyl.

The aryl refers to a 6 to 10 membered full-carbon monocyclic or fused polycyclic group (a fused polycyclic group means that each ring shares an adjacent pair of carbon atoms with another ring), having a conjugated π-electron system, such as phenyl and naphthyl. The said aryl can be fused to the ring of heterocyclyl, heteroaryl, or cycloalkyl. Representative examples of aryl include, but are not limited to benzimidazolyl, benzothiazolyl, benzoxazolyl, benzisoxazolyl, benzopyrazolyl, quinolinyl, benzindolyl, benzodihydrofuryl.

The heteroaryl refers to a hetero aromatic system containing 5 to 14 ring atoms and 1 to 4 heteroatoms selected from the group consisting of oxygen, sulfur, and nitrogen. Preferably the heteroaryl is 5- to 10-membered ring. More preferably, heteroaryl is a 5- or 6-membered ring, such as furyl, thienyl, pyridyl, pyrrolyl, N-alkyl pyrrolyl, pyrimidinyl, pyrazinyl, imidazolyl, tetrazolyl. The heteroaryl can be fused with the aryl, heterocyclyl, or cycloalkyl, wherein the ring connected with parent structure is heteroaryl.

The present invention is meant to include all appropriate tautomeric forms of substituted triazolopiperazine compounds represented by formula I.

In one embodiment, when Y is

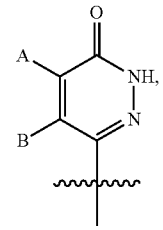

the tautomeric forms of substituted triazolopiperazine compounds represented by formula I may include, but are not limited to, the structure of following formula (II), wherein X, A, B, and R are as defined above:

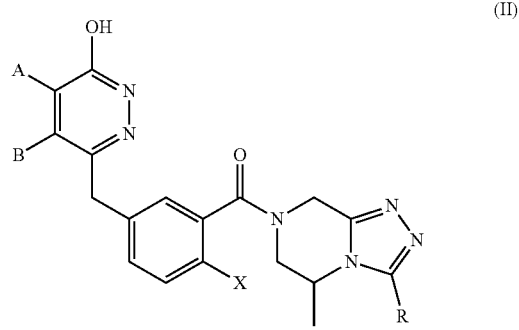

(II)

The representative compounds of present invention include, but are not limited to the following:
| Compound No. | Structure |
|---|---|
| S1 | 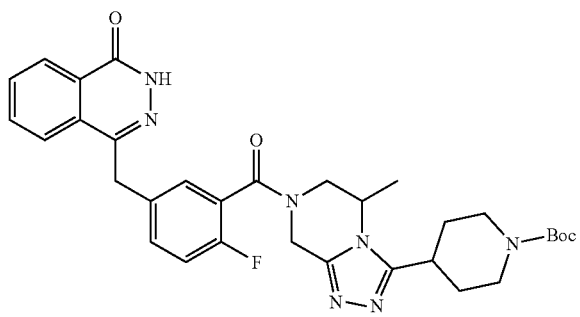 |
| S2 | 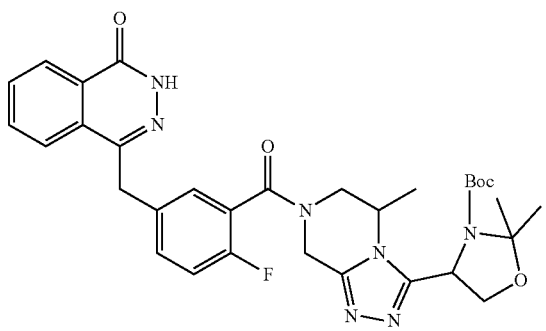 [SMILES: CC1CN(C(=O)c2cc(Cc3n[nH]c(=O)c4ccccc34)ccc2F)Cc2nnc(C3COC(C)(C)N3C(=O)OC(C)(C)C)n21] |
| S3 | 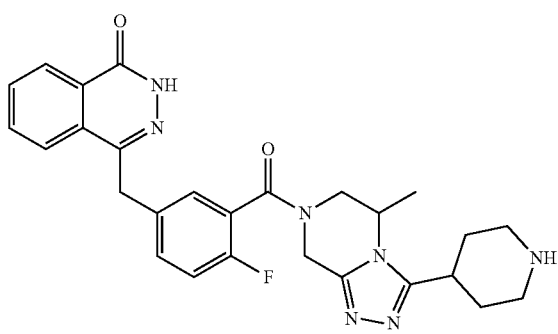 [SMILES: CC1CN(C(=O)c2cc(Cc3n[nH]c(=O)c4ccccc34)ccc2F)Cc2nnc(C3CCNCC3)n21] |
| S4 | 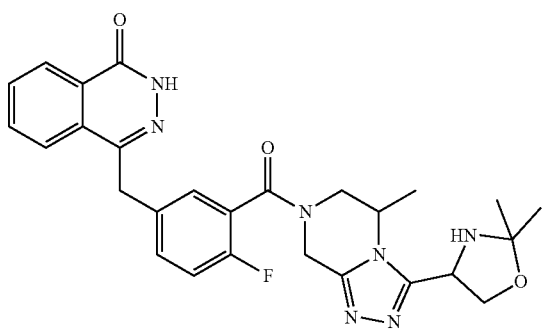 [SMILES: CC1CN(C(=O)c2cc(Cc3n[nH]c(=O)c4ccccc34)ccc2F)Cc2nnc(C3COC(C)(C)N3)n21] |

-continued
| Compound No. | Structure |
|---|---|
| S5 | 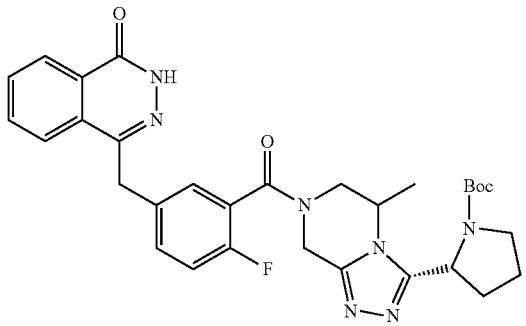 |
| S6 | 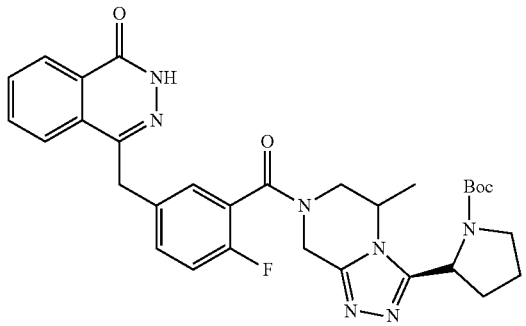 |
| S7 | 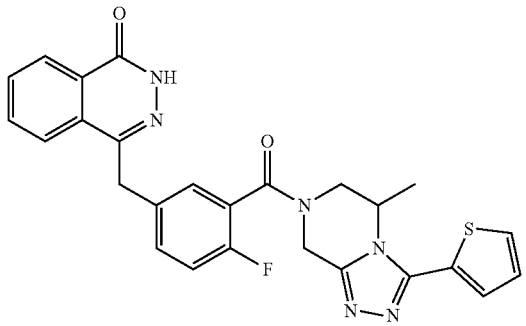 [SMILES: CC1CN(C(=O)c2cc(Cc3n[nH]c(=O)c4ccccc34)ccc2F)Cc2nnc(-c3cccs3)n21] |
| S8 | 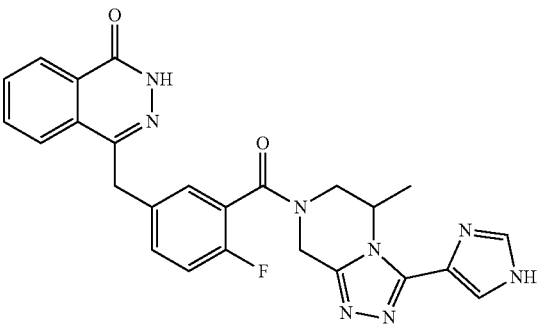 [SMILES: CC1CN(C(=O)c2cc(Cc3n[nH]c(=O)c4ccccc34)ccc2F)Cc2nnc(-c3c[nH]cn3)n21] |

| Compound No. | Structure |
|---|---|
| S9 | 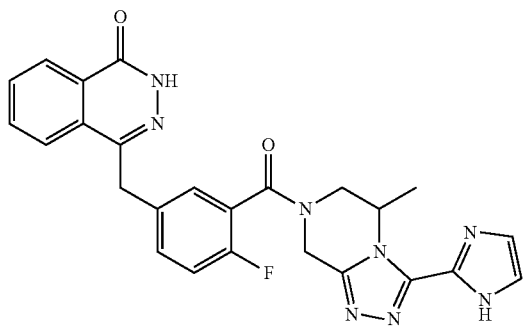 [SMILES: CC1CN(C(=O)c2cc(Cc3n[nH]c(=O)c4ccccc34)ccc2F)Cc2nnc(-c3ncc[nH]3)n21] |
| S10 | 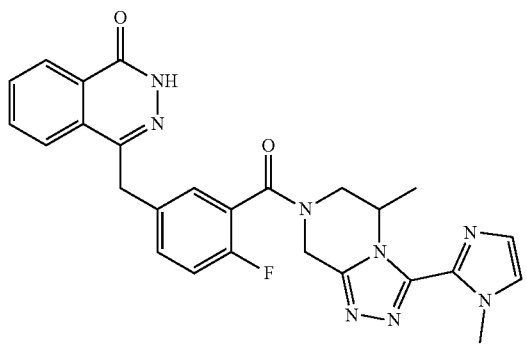 [SMILES: CC1CN(C(=O)c2cc(Cc3n[nH]c(=O)c4ccccc34)ccc2F)Cc2nnc(-c3nccn3C)n21] |
| S11 | 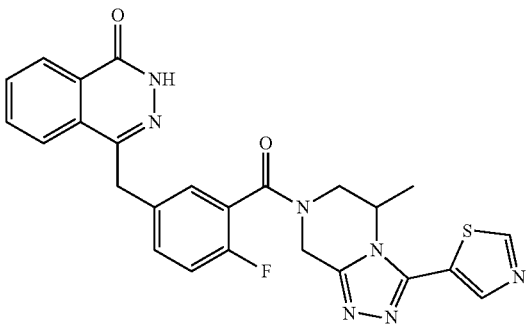 [SMILES: CC1CN(C(=O)c2cc(Cc3n[nH]c(=O)c4ccccc34)ccc2F)Cc2nnc(-c3cncs3)n21] |
| S12 | 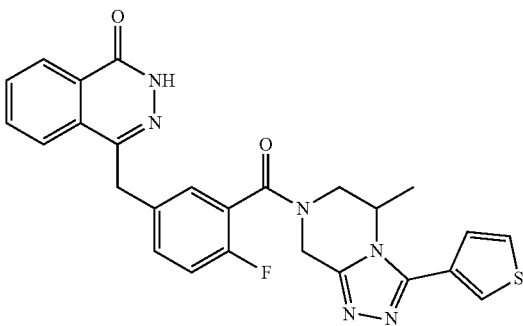 [SMILES: CC1CN(C(=O)c2cc(Cc3n[nH]c(=O)c4ccccc34)ccc2F)Cc2nnc(-c3ccsc3)n21] |

-continued
| Compound No. | Structure |
|---|---|
| S13 | 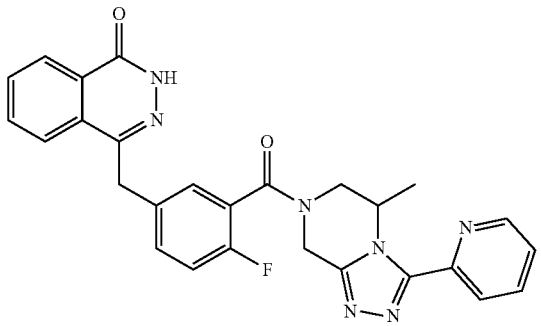 [SMILES: CC1CN(C(=O)c2cc(Cc3n[nH]c(=O)c4ccccc34)ccc2F)Cc2nnc(-c3ccccn3)n21] |
| S14 | 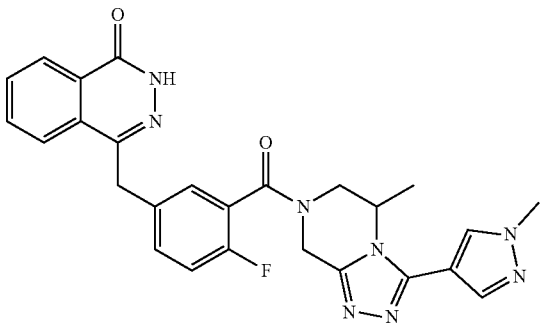 [SMILES: CC1CN(C(=O)c2cc(Cc3n[nH]c(=O)c4ccccc34)ccc2F)Cc2nnc(-c3cnn(C)c3)n21] |
| S15 | 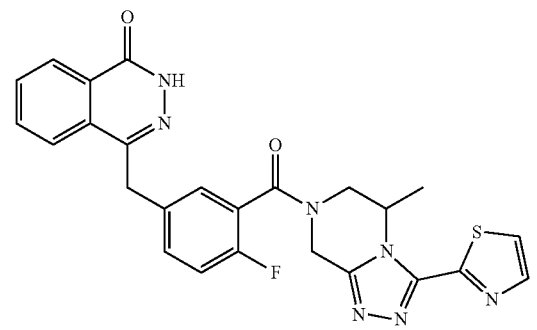 [SMILES: CC1CN(C(=O)c2cc(Cc3n[nH]c(=O)c4ccccc34)ccc2F)Cc2nnc(-c3nccs3)n21] |
| S16 | 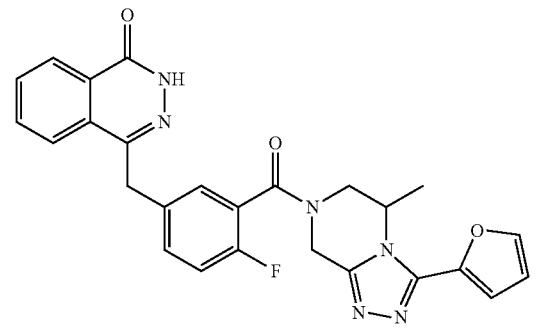 [SMILES: CC1CN(C(=O)c2cc(Cc3n[nH]c(=O)c4ccccc34)ccc2F)Cc2nnc(-c3ccco3)n21] |

-continued
| Compound No. | Structure |
|---|---|
| S17 | 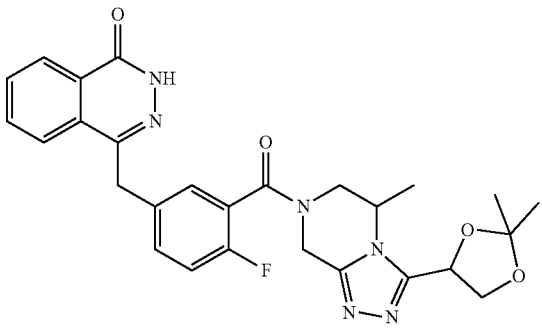 [SMILES: CC1CN(C(=O)c2cc(Cc3n[nH]c(=O)c4ccccc34)ccc2F)Cc2nnc(C3COC(C)(C)O3)n21] |
| S18 | 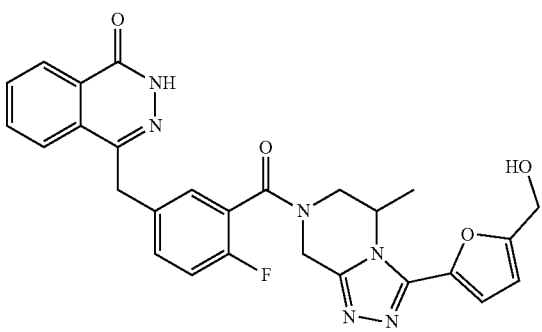 [SMILES: CC1CN(C(=O)c2cc(Cc3n[nH]c(=O)c4ccccc34)ccc2F)Cc2nnc(-c3ccc(CO)o3)n21] |
| S19 | 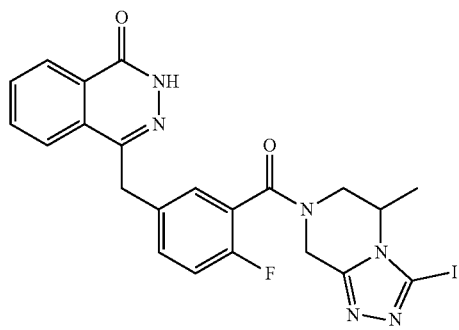 [SMILES: CC1CN(C(=O)c2cc(Cc3n[nH]c(=O)c4ccccc34)ccc2F)Cc2nnc(I)n21] |
| S20 | 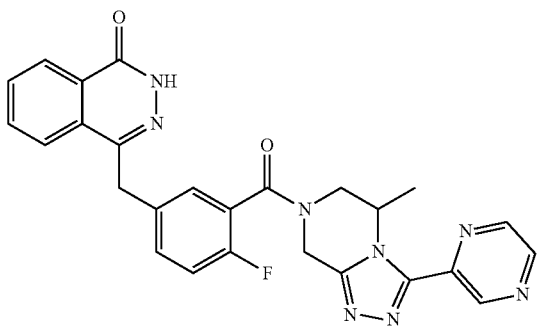 |

-continued
| Compound No. | Structure |
|---|---|
| S21 | 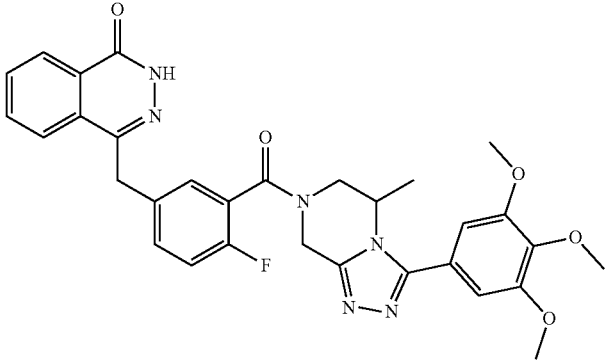 [SMILES: COc1cc(-c2nnc3n2C(C)CN(C(=O)c2cc(Cc4n[nH]c(=O)c5ccccc45)ccc2F)C3)cc(OC)c1OC] |
| S22 | 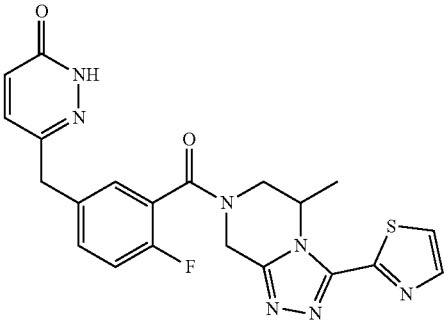 [SMILES: CC1CN(C(=O)c2cc(Cc3ccc(=O)[nH]n3)ccc2F)Cc2nnc(-c3nccs3)n21] |
| S23 | 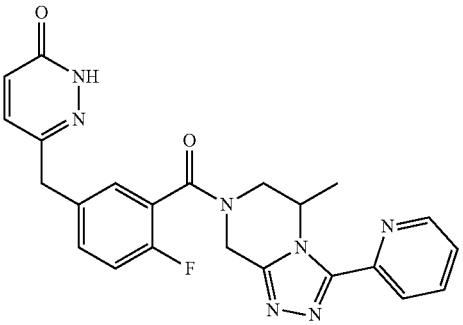 [SMILES: CC1CN(C(=O)c2cc(Cc3ccc(=O)[nH]n3)ccc2F)Cc2nnc(-c3ccccn3)n21] |
| S24 | 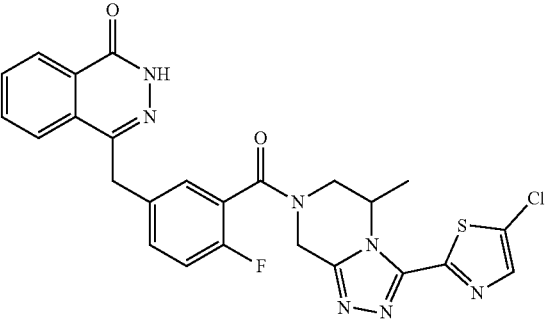 [SMILES: CC1CN(C(=O)c2cc(Cc3n[nH]c(=O)c4ccccc34)ccc2F)Cc2nnc(-c3ncc(Cl)s3)n21] |

| Compound No. | Structure |
|---|---|
| S25 | 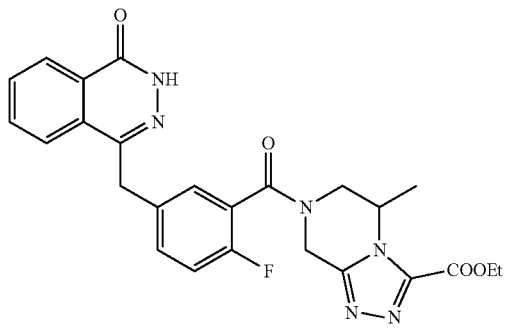 [SMILES: CCOC(=O)c1nnc2n1C(C)CN(C(=O)c1cc(Cc3n[nH]c(=O)c4ccccc34)ccc1F)C2] |
| S26 | 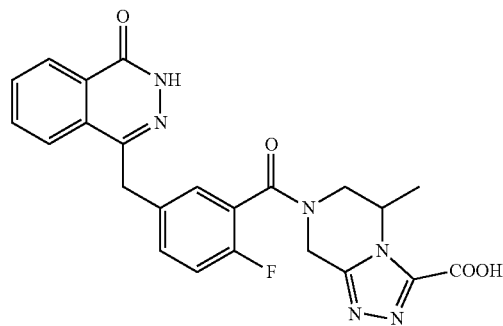 [SMILES: CC1CN(C(=O)c2cc(Cc3n[nH]c(=O)c4ccccc34)ccc2F)Cc2nnc(C(=O)O)n21] |
| S27 | 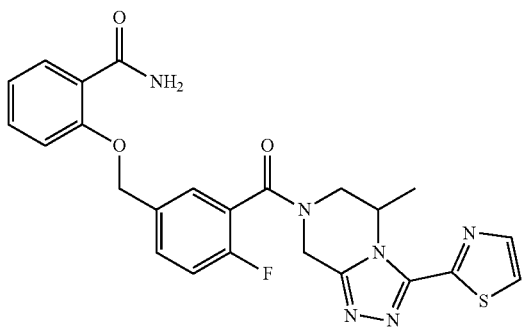 [SMILES: CC1CN(C(=O)c2cc(COc3ccccc3C(N)=O)ccc2F)Cc2nnc(-c3nccs3)n21] |
| S28 | 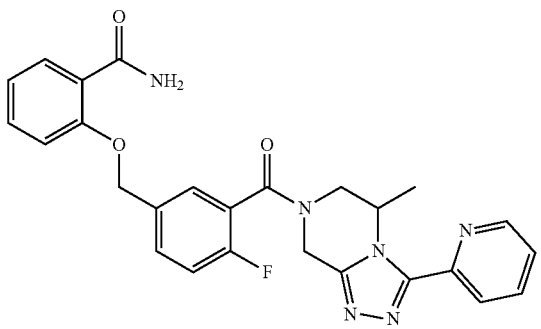 [SMILES: CC1CN(C(=O)c2cc(COc3ccccc3C(N)=O)ccc2F)Cc2nnc(-c3ccccn3)n21] |

-continued

| Compound No. | Structure |
|---|---|
| S29 | 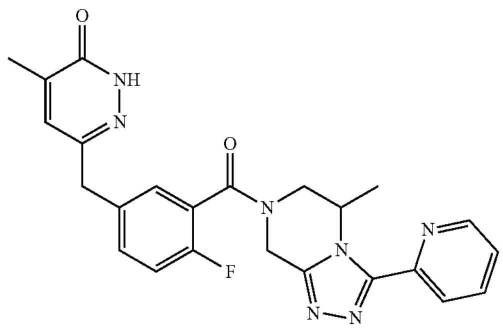 [SMILES: Cc1cc(Cc2ccc(F)c(C(=O)N3Cc4nnc(-c5ccccn5)n4C(C)C3)c2)n[nH]c1=O] |
| S30 | 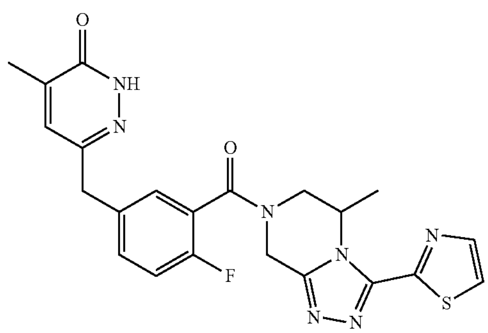 [SMILES: Cc1cc(Cc2ccc(F)c(C(=O)N3Cc4nnc(-c5nccs5)n4C(C)C3)c2)n[nH]c1=O] |
| S31 | 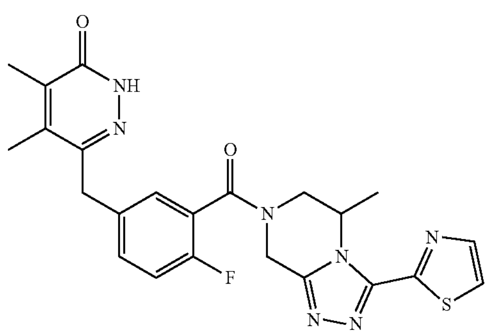 [SMILES: Cc1c(Cc2ccc(F)c(C(=O)N3Cc4nnc(-c5nccs5)n4C(C)C3)c2)n[nH]c(=O)c1C] |
| S32 | 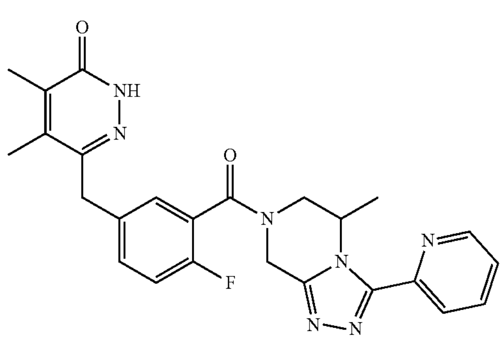 [SMILES: Cc1c(Cc2ccc(F)c(C(=O)N3Cc4nnc(-c5ccccn5)n4C(C)C3)c2)n[nH]c(=O)c1C] |

-continued
| Compound No. | Structure |
|---|---|
| S33 | 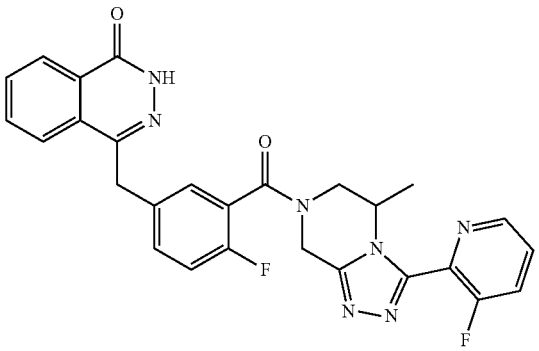 [SMILES: CC1CN(C(=O)c2cc(Cc3n[nH]c(=O)c4ccccc34)ccc2F)Cc2nnc(-c3ncccc3F)n21] |
| S34 | 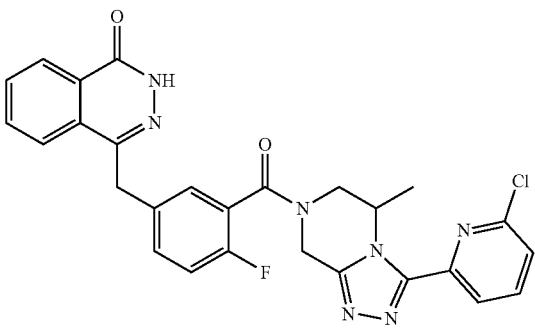 [SMILES: CC1CN(C(=O)c2cc(Cc3n[nH]c(=O)c4ccccc34)ccc2F)Cc2nnc(-c3cccc(Cl)n3)n21] |
| S35 | 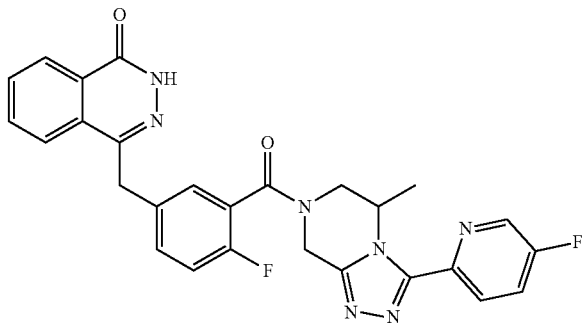 [SMILES: CC1CN(C(=O)c2cc(Cc3n[nH]c(=O)c4ccccc34)ccc2F)Cc2nnc(-c3ccc(F)cn3)n21] |
| S36 | 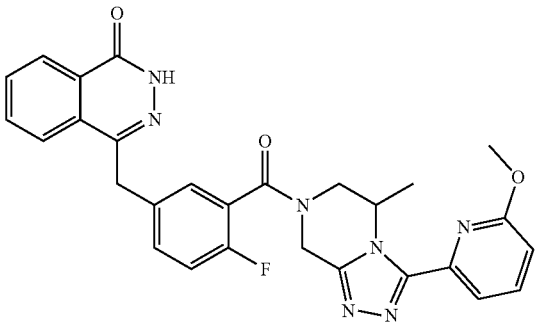 [SMILES: COc1cccc(-c2nnc3n2C(C)CN(C(=O)c2cc(Cc4n[nH]c(=O)c5ccccc45)ccc2F)C3)n1] |

| Compound No. | Structure |
|---|---|
| S37 | 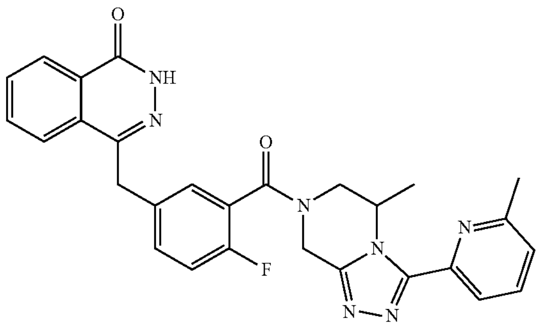 [SMILES: Cc1cccc(-c2nnc3n2C(C)CN(C(=O)c2cc(Cc4n[nH]c(=O)c5ccccc45)ccc2F)C3)n1] |
| S38 | 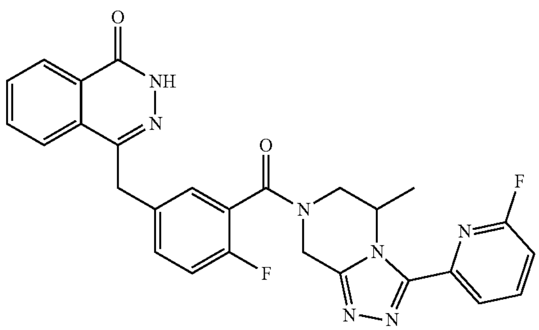 |
| S39 | 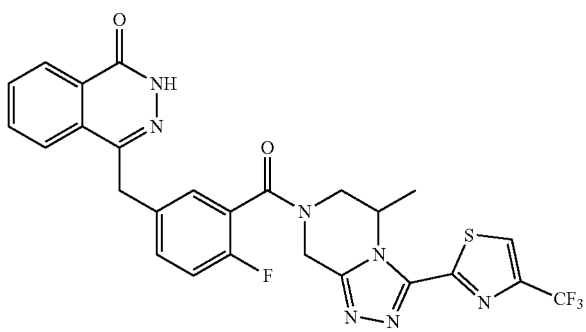 [SMILES: CC1CN(C(=O)c2cc(Cc3n[nH]c(=O)c4ccccc34)ccc2F)Cc2nnc(-c3nc(C(F)(F)F)cs3)n21] |

The substituted triazolopiperazine compound represented by formula (I) may be prepared by the following reaction route:

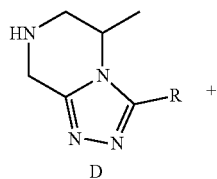

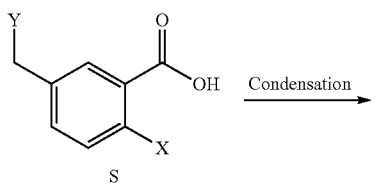

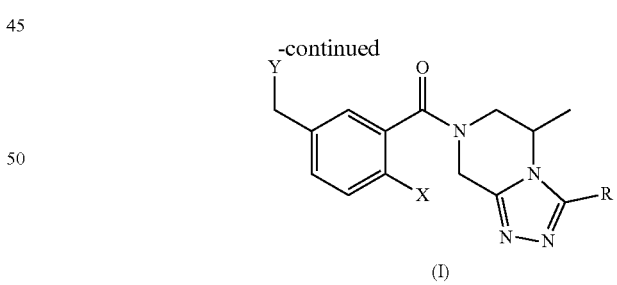

wherein, the definitions of X, Y, and R are the same as those in formula (I);

reacting compound S with compound D via condensation reaction to give a substituted triazolopiperazine compound represented by formula (I); preferably, reacting compound S with compound D in an appropriate solvent in the presence of a condensing agent and a suitable base; catalyst being used as needed.

Wherein, synthesis of compound S may be referred to the reference document, e.g., *J. Med. Chem.* 2008, 51, 6581-6591, *Bioorg. Med. Chem. Lett.* 2010, 20, 1100-1105, or Bioorg. Med. Chem. Lett. 2008, 18, 3942-3945, CN201110082475. Synthesis of compound D may be referred to the reference document, e.g, Green. Chem. 2004, 6, 156-157, J. Med. Chem. 2008, 51, 589-602.

The compound D may be prepared as follows:

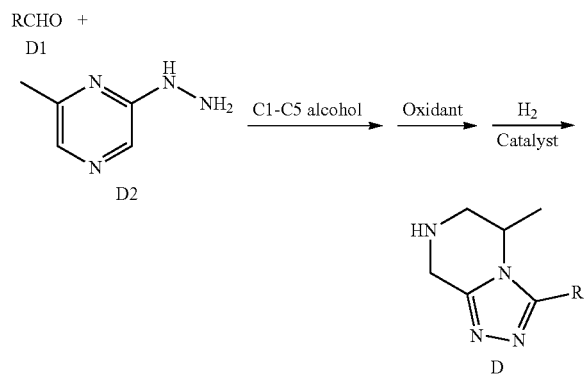

dissolving compound D1 and compound D2 in C1-C5 alcohol, then grinding with an oxidant, and dissolving the ground powder in dichloromethane; after that, washing, concentrating and then dissolving with C1-C5 alcohol, adding a catalyst and charging with $H_2$ to produce compound D.

A specific method for preparing the substituted triazolopiperazine compound represented by formula (I) is as follows:

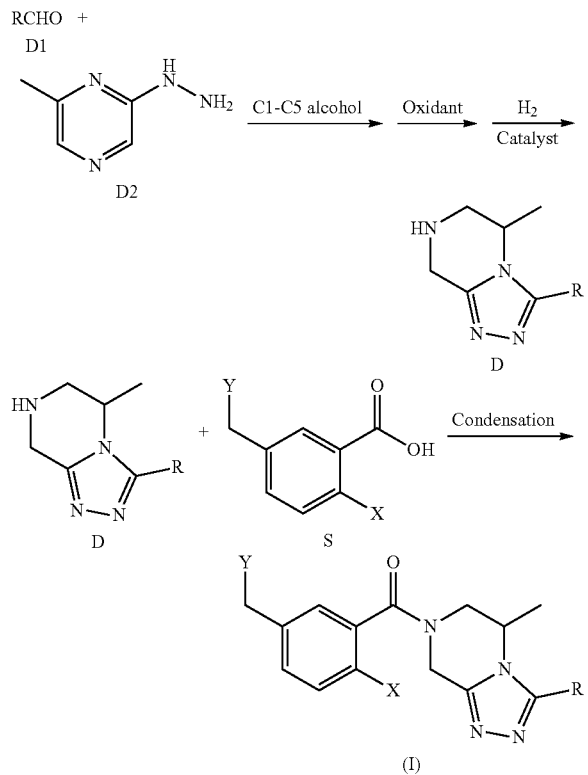

(1) dissolving compound D1 and compound D2 in C1-C5 alcohol and stirring overnight at room temperature; after the reaction completed, removing the solvent by rotary evaporation, adding the oxidant and grinding, then dissolving the ground powder in dichloromethane and washing with saturated sodium sulfite solution, brine, followed by concentration and dryness, then dissolving in C1-C5 alcohol, adding a catalyst and charging with $H_2$; stirring at 0 to 80° C. for 1-48 hours; after the reaction completed, carrying out filtration to remove the catalyst and concentrating the reaction mixture by rotary evaporation to obtain an amine D; wherein, the C1-C5 alcohol is one or more types of alcohols selected from methanol, ethanol, isopropanol, n-propanol, tert-butanol and n-butanol; preferably methanol, ethanol and combinations thereof; more preferably ethanol; the oxidant is selected from one or more of [bis(trifluoroacetoxy)iodo]benzene and (diacetoxyiodo)benzene; the catalyst is selected from one or more of palladium/carbon, Raney nickel and platinum carbon.

(2) reacting compound S with the compound D in an appropriate solvent in the presence of a condensing agent and an appropriate base; and adding a catalyst as needed; wherein, the condensing agent is selected from one or more of the group consisting of N,N'-dicyclohexylcarbodiimide (DCC), N-(3-Dimethylaminopropyl)-N'-ethylcarbodiimide or hydrochloride thereof (EDC or EDC-HCl), 1,1'-carbonyldiimidazole (CDI), N,N'-diisopropylcarbodiimide (DIC), O-(1,2-dihydro-2-oxo-pyridyl)-N,N,N',N'-tetramethyluronium tetrafluoroborate, O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), benzotriazole-N,N,N',N'-tetramethyluronium hexafluorophosphate (HBTU), 2-(7-azabenzotriazole)-N,N,N',N'-tetramethyluronium hexafluorophosphate, O-(6-chloro-1H-benzotriazol-1-yl)-N,N,N',N'-tetramethyluronium hexafluorophosphate, benzotriazol-1-yloxytris(dimethylamino)phosphonium hexafluorophosphate (BOP) and benzotriazole-1-yl-oxytripyrrolidinophosphonium hexafluorophosphate (PyBOP), preferably one or more of the group consisting of benzotriazole-N,N,N',N'-tetramethyluronium hexafluorophosphate, O-(benzotriazol-1-yl)-N,N,N',N'-tetramethyluronium tetrafluoroborate and O-(1,2-dihydro-2-oxo-pyridyl)-N,N,N',N'-tetramethyluronium tetrafluoroborate; wherein the base used is selected from one or more of the group consisting of triethylamine, diethylamine, tributylamine, tripropylamine, diisopropylamine, diisopropylethylamine (DIPEA), trimethylamine, pyridine, 2,6-lutidine, 4-dimethylaminopyridine, piperidine, pyrrolidine, quinoline, morpholine, N-methylmorpholine (NMM), N-ethylmorpholine, N-methylpiperidine, diisopropylamine, diisopropylethylamine, 1,8-Diazabicyclo[5.4.0]undec-7-ene, and 1,5-diazabicyclo[4.3.0]-non-5-ene; preferably triethylamine, diisopropylethylamine or mixture thereof; wherein, the solvent used is selected from one or more of the group consisting of benzene, xylene, toluene, dichloromethane, chloroform, carbon tetrachloride, tetrahydrofuran, 2-methyltetrahydrofuran, ethyl ether, acetone, 1,4-dioxane, N,N-dimethylformamide, N,N-diethylformamide, N,N-dimethylacetamide, acetonitrile, dimethyl sulfoxide; preferably selected from one or more of the group consisting of dichloromethane, chloroform, N,N-dimethylformamide, N,N-dimethylacetamide; wherein, the catalyst used is selected from one or more of the group consisting of 1-hydroxybenzotriazole (HOBt) and 4-dimethylaminopyridine (DMAP); the reaction temperature is controlled between −10° C. and 100° C., preferably between 15° C. and 40° C.; The reaction time is controlled between 1 and 48 hours, preferably between 6 and 24 hours.

Specifically, a preferred preparation method may include the following steps: (1) dissolving compound D1 (1 eq.) and compound D2 (1 eq.) in ethanol and stirring overnight at room temperature; after the reaction completed, removing the solvent by rotary evaporation, adding (diacetoxyiodo)benzene (1.5 eq.) and grinding for 2 minutes, then dissolving the ground powder in dichloromethane, washing with saturated sodium sulfite solution, brine, followed by concentration and dryness; thereafter, dissolving in ethanol, adding Palladium/carbon (0.1 eq.) and charging with $H_2$; heating the solution at 50° C. for 12 hours; after full completion, carrying out filtration to remove Palladium/carbon and concentrating the reaction mixture by rotary evaporation to obtain the amine D;

(2) dissolving compound S (1 eq.) and compound D (1 eq.) in DMF, cooling the solution with an ice bath, and adding benzotriazole-N,N,N',N'-tetramethyluronium hexafluorophosphate and diisopropylethylamine successively; gradually warming to room temperature and reacting for 12 hours; adding water with ice cooling and extracting with dichloromethane; washing the dichloromethane layer with brine, drying, and distilling off the solvent, followed by purification with column chromatography to afford the substituted triazolopiperazine compound represented by formula (I).

The synthesized compound may also be further transformed by reactions such as hydrolysis reaction. For example, when R is heterocyclic ring substituted by C2-C4 alkoxycarbonyl, heteroaromatic ring substituted by C2-C4 alkoxycarbonyl, or aromatic ring substituted by C2-C4 alkoxycarbonyl, a compound with an unsubstituted heterocyclic ring, an unsubstituted heteroaromatic ring, or an unsubstituted aromatic ring may be afforded via a hydrolysis reaction.

In another aspect of the present invention, provided is a use of the substituted triazolopiperazine compounds represented by formula (I), or tautomers, enantiomers, diastereomers, racemates, metabolites, metabolism precursors, pharmaceutically acceptable salts, esters, prodrugs or hydrates thereof, especially, as a novel highly selective PARP-1 inhibitor, in the preparation of medicament for the prevention and/or treatment of diseases associated with PARP (poly ADP ribose polymerase), the diseases include various ischemic diseases (brain ischemia, ischemic disease of spinal cord, ischemic heart disease, ischemic disease of digestive tube, retinal ischemic disease etc.), neurodegenerative diseases (Parkinson's disease, Alzheimer's disease, muscular dystrophy etc.) and cancers (breast cancer, ovarian cancer, liver cancer, melanoma, prostate cancer, colon cancer, gastric cancer and other solid tumors).

In another aspect of the present invention, provided is a pharmaceutical composition comprising a therapeutically effective amount of one or more substituted triazolopiperazine compounds represented by formula (I), tautomers, enantiomers, diastereomers, racemates, metabolites, metabolism precursors, pharmaceutically acceptable salts, esters, prodrugs or hydrates thereof, and optional one or more pharmaceutically acceptable carriers or excipients.

In another aspect of the present invention, provided is a PARP-1 inhibitor comprising a therapeutically effective amount of one or more substituted triazolopiperazine compounds represented by formula (I), tautomers, enantiomers, diastereomers, racemates, metabolites, metabolism precursors, pharmaceutically acceptable salts, esters, prodrugs or hydrates thereof, and optional one or more pharmaceutically acceptable carriers or excipients.

DETAILED DESCRIPTION OF EXEMPLARY EMBODIMENTS

Figure 1:
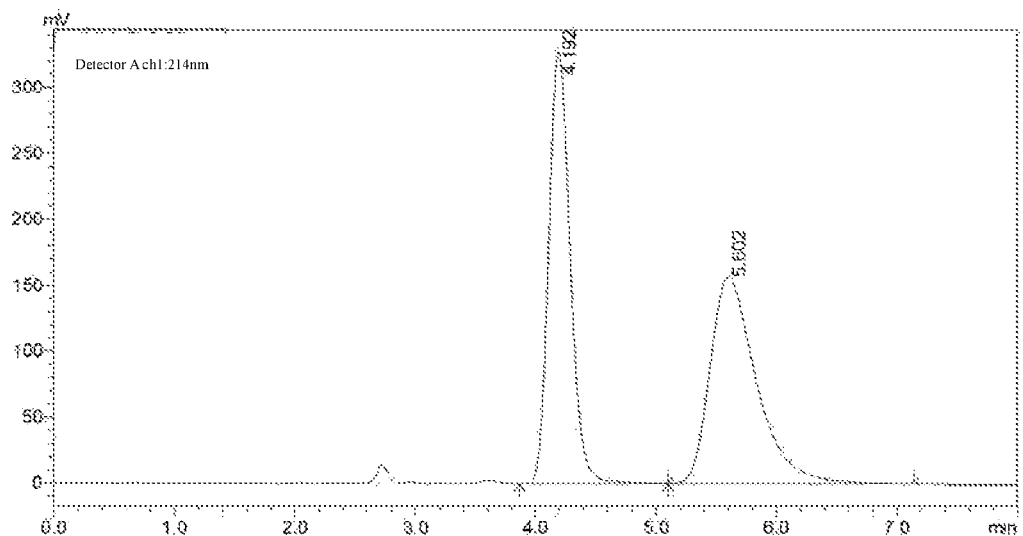
FIG. 1 is a HPLC spectrum of compound S13.

The present invention will be further illustrated based on the following examples, but the present invention will not be limited thereto.

I. Preparation Examples for Compounds

In following preparation examples, $^1$H-NMR was conducted on a MercuryAMX300 instrument manufactured by Varian. Mass spectra were obtained using either a VG ZAB-HS or a VG-7070 mass spectrometer by EI sources (70 ev) unless noted. All solvents were redistilled before use. All the anhydrous solvents used were dried by standard methods when necessary. Unless otherwise stated, all reactions were carried out under nitrogen protection and followed by TLC. The residue was washed with brine after quenching and dried over anhydrous $Na_2SO_4$. The silica gel plate (model GF 254) for thin layer chromatography (TLC) was manufactured by Huiyou Silica gel Development Co. Ltd., Yantai, Shandong. Unless noted, the compounds were purified by column chromatography with a silica gel of 200-300 mesh, manufactured by Qingdao Haiyang Chemical Co. Ltd.

1 Synthesis of Compound S1

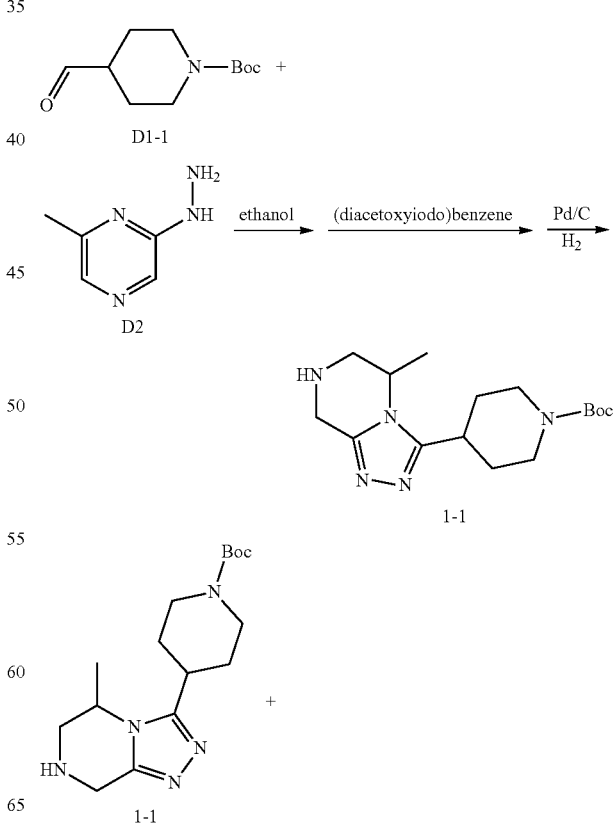

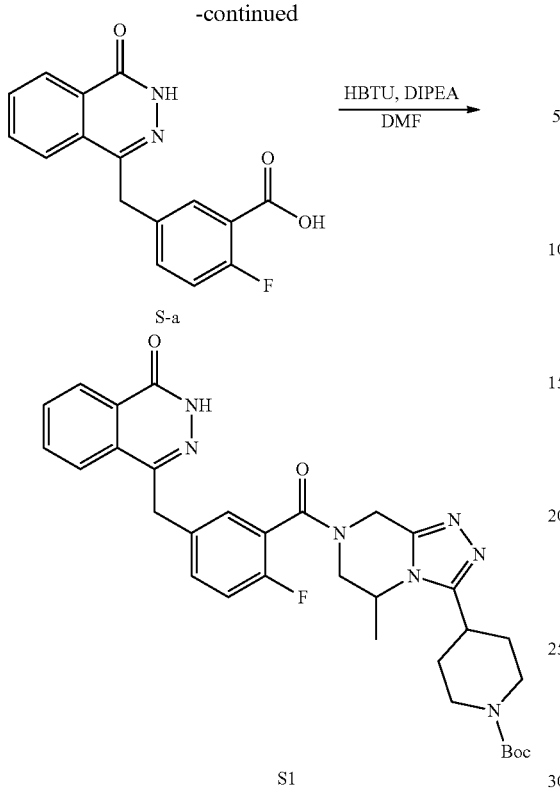

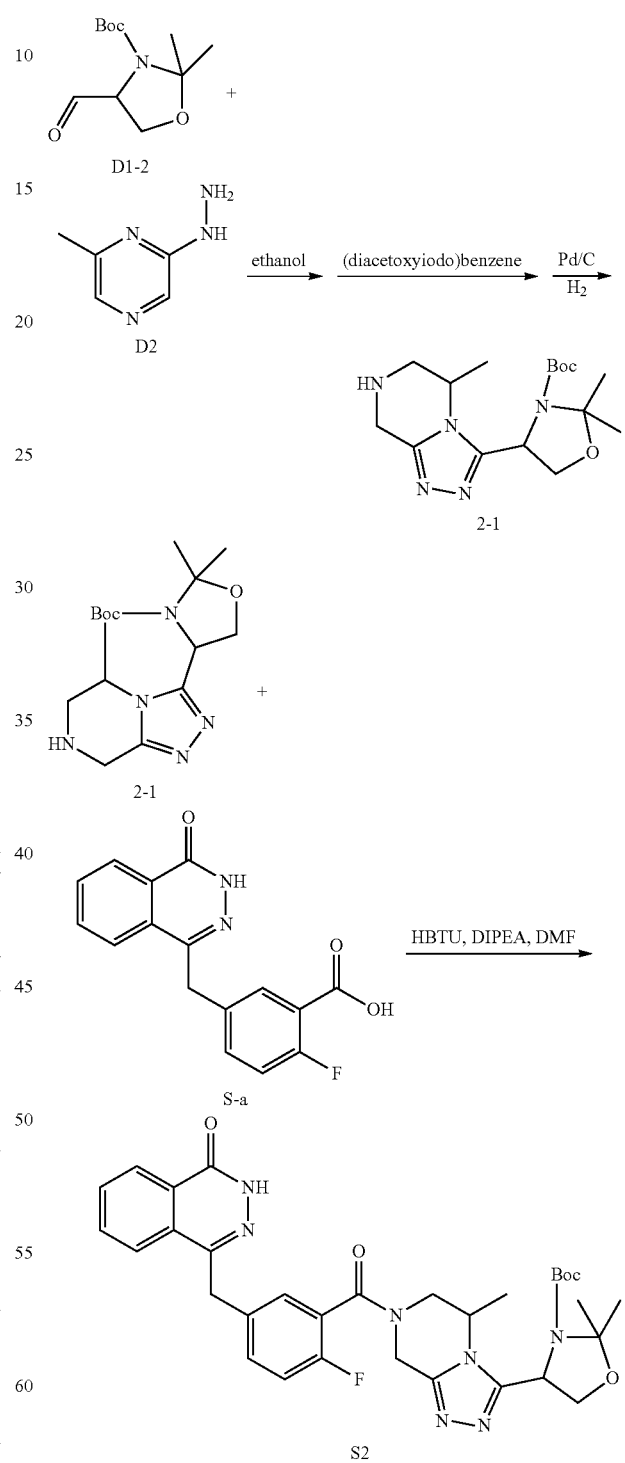

Thereinto, the synthesis of S-a is described in *J. Med. Chem.* 2008, 51, 6581-6591, and the synthesis of 1-1 is described in *Green. Chem.* 2004, 6, 156-157, *J. Med. Chem.* 2008, 51, 589-602. HBTU is the abbreviation for benzotriazole-N,N,N',N'-tetramethyluronium hexafluorophosphate, DIPEA is the abbreviation for diisopropylethylamine, DMF is the abbreviation for N,N-dimethylformamide.

The compound DI-1 (1 eq.) and D2 (1 eq.) were dissolved in ethanol and stirred overnight at room temperature. After the reaction was completed, the solvent was removed using rotary evaporation, then (diacetoxyiodo)benzene (1.5 eq.) was added, and ground for 2 minutes. The ground powder was dissolved in dichloromethane. The solution was washed with saturated sodium sulfite solution, brine, concentrated. The residue was dissolved in ethanol, added Palladium/carbon (0.1 eq.) and charged with $H_2$. The reaction was carried out at 50° C. for 12 hours. After the reaction was complete, palladium/carbon was filtered off and the residue was concentrated by rotary evaporation to give compound 1-1. $^1$H NMR (300 MHz, Chloroform-d) δ 4.32-4.00 (m, 4H), 3.17 (dd, J=13.3, 4.2 Hz, 1H), 3.04 (d, J=12.5 Hz, 1H), 2.79 (d, J=31.5 Hz, 2H), 2.07 (s, 2H), 1.94-1.75 (m, 3H), 1.50-1.39 (m, 9H).

Intermediate S (1 eq.) and 3-cyclopropyl-5-methyl-5,6,7,8-tetrahydro[1,2,4]triazolo[4,3-a]piperazine (compound 1-1) (1 eq.) were dissolved in DMF. Cooling with ice bath, benzotriazole-N,N,N',N'-tetramethyluronium hexafluorophosphate (1.5 eq.) then DIPEA (2 eq.) were added to the solution. The reaction mixture was gradually warmed to room temperature and reacted for 12 hours. Water was added under an ice bath. After the addition, the mixture was extracted three times with dichloromethane. The combined dichloromethane layers were washed with brine, dried, concentrated and purified using column chromatography to provide compound S1 as a white solid. $^1$H NMR (300 MHz, Chloroform-d) δ 11.07 (s, 1H), 8.43 (d, J=7.3 Hz, 1H), 7.71 (dt, J=19.3, 7.3 Hz, 3H), 7.32 (d, J=8.4 Hz, 2H), 7.07 (d, J=8.8 Hz, 1H), 4.85 (d, J=15.5 Hz, 2H), 4.50 (d, J=47.4 Hz, 2H), 4.24 (d, J=21.6 Hz, 4H), 3.37 (d, J=13.7 Hz, 1H), 2.86 (s, 3H), 2.13-1.67 (m, 5H), 1.44 (s, 9H).

2 Synthesis of Compound S2

Compound 2-1 was prepared by replacing the compound D1-1 in synthesis method of compound 1-1 with compound D1-2. Analysis data of 2-1: $^1$H NMR (300 MHz, Chloroform-d) δ 5.09 (dd, J=6.7, 3.2 Hz, 1H), 4.47-3.78 (m, 5H), 3.27-2.89 (m, 2H), 1.80 (s, 3H), 1.49 (d, J=42.3 Hz, 15H).

Compound S2 was prepared by replacing the compound 1-1 in synthesis method of compound S1 with compound 2-1. Analysis data of S2: ¹H NMR (300 MHz, Chloroform-d) δ 10.66 (s, 1H), 8.44 (d, J=7.3 Hz, 1H), 7.94-7.59 (m, 3H), 7.34 (d, J=6.0 Hz, 2H), 7.07 (t, J=8.8 Hz, 1H), 5.18-5.03 (m, 1H), 4.85 (d, J=15.8 Hz, 2H), 4.69-4.39 (m, 2H), 4.28 (s, 3H), 4.04 (s, 1H), 3.30 (d, J=14.0 Hz, 1H), 1.75 (d, J=14.5 Hz, 4H), 1.59-0.98 (m, 14H).

3 Synthesis of Compound S3

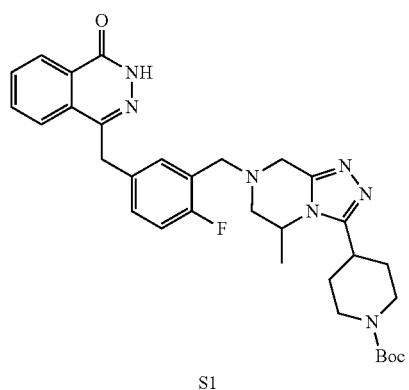

S1

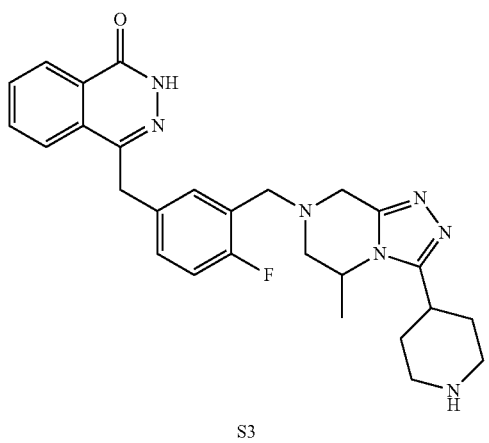

S3

The Compound S1 was dissolved in ethanol, then added 6N hydrochloric acid. The mixture was stirred at room temperature for overnight. Then, the solvent was removed by rotary evaporation and the residue was stirred with ammonium hydroxide for 30 minutes. After the reaction was completed, ammonium hydroxide was removed by rotary evaporation and the residue was purified by column chromatography to provide Compound S3 as a white solid. Analysis data of S3: ¹H NMR (400 MHz, DMSO-d₆) δ 12.62 (s, 1H), 8.26 (d, J=7.8 Hz, 1H), 8.11-7.75 (m, 3H), 7.61-7.22 (m, 3H), 5.42 (d, J=17.4 Hz, 0.5H), 4.88-4.47 (m, 4H), 4.36 (s, 2H), 3.95-3.60 (m, 8H), 3.50 (s, 0.5H), 1.25-1.00 (m, 3H).

4 Synthesis of Compound S4

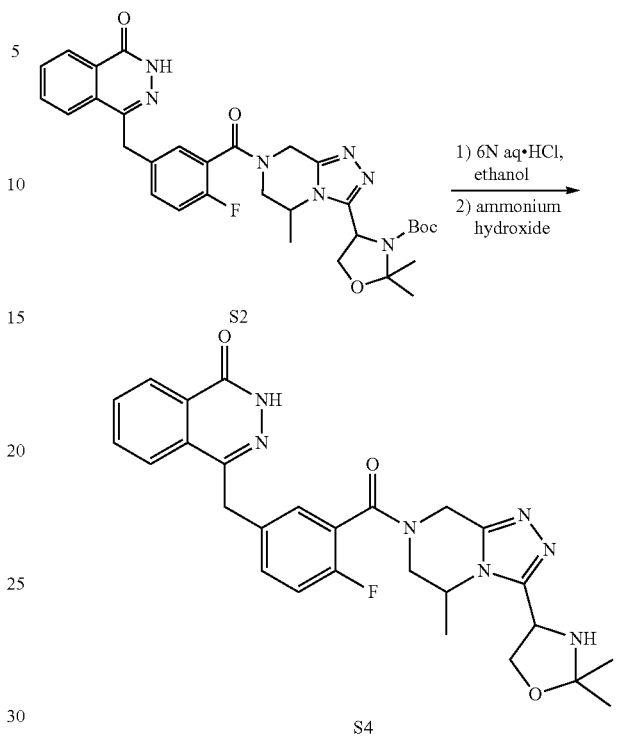

Compound S4 was prepared by replacing the compound S1 in synthesis method of compound S3 with compound S2. Analysis data of S4: ¹H NMR (400 MHz, DMSO-d₆) δ 12.63 (s, 1H), 8.26 (d, J=7.7 Hz, 1H), 8.09-7.75 (m, 3H), 7.65-7.19 (m, 3H), 5.39 (d, J=17.9 Hz, 1H), 4.85-4.44 (m, 3H), 4.35 (s, 2H), 3.41 (dd, J=81.2, 18.2 Hz, 4H), 3.04 (s, 2H), 2.30 (s, 6H), 1.40-0.96 (m, 3H).

5 Synthesis of Compound S5

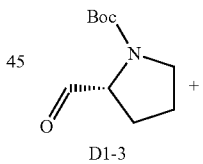

D1-3

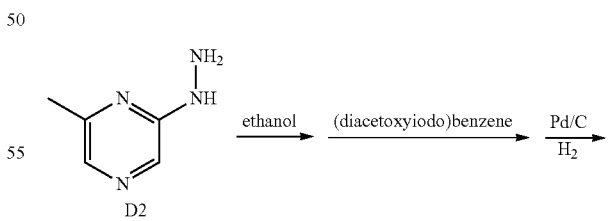

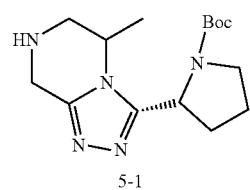

5-1

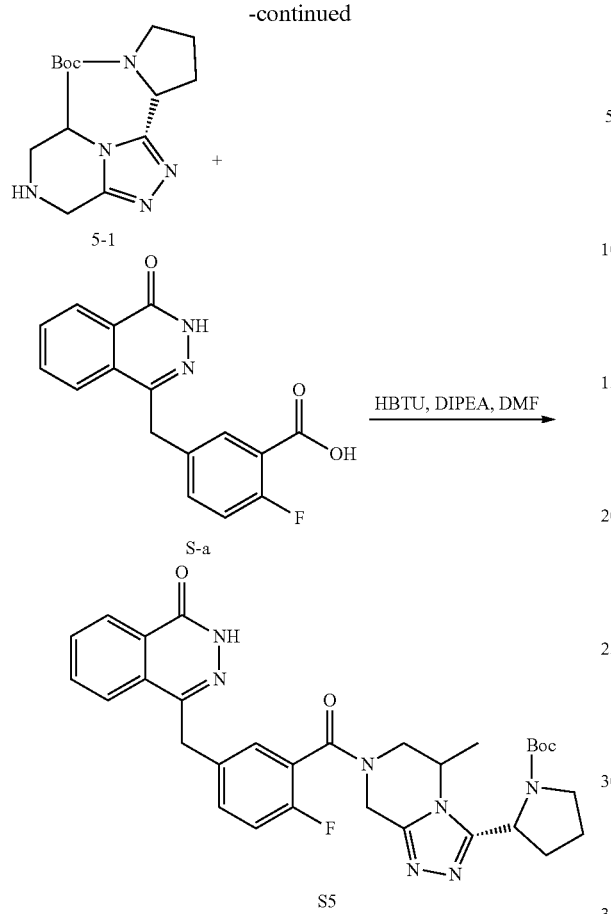

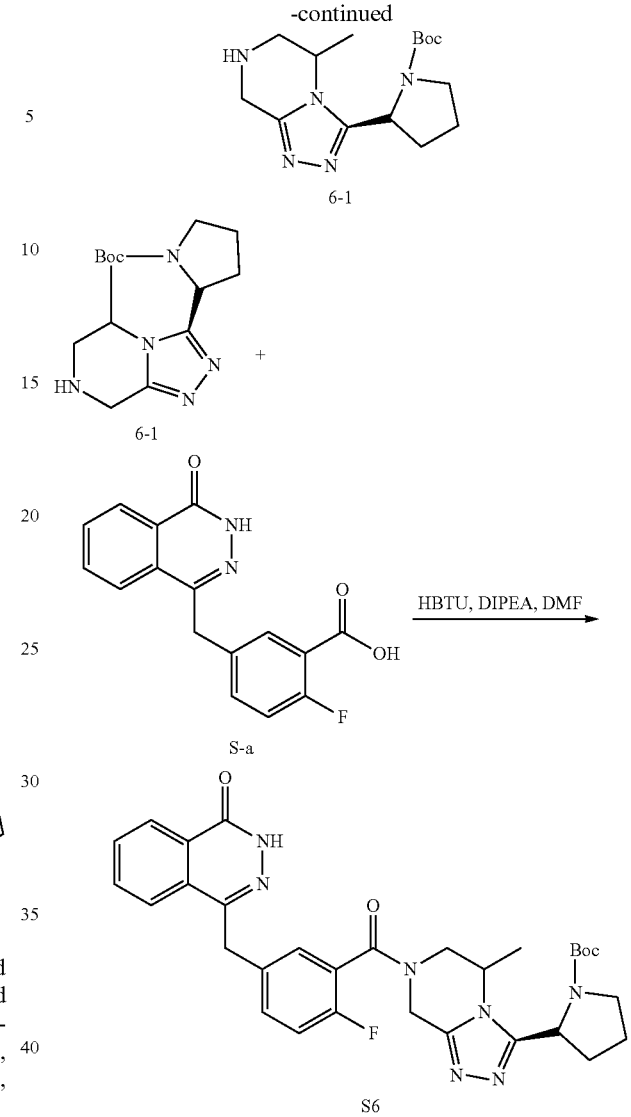

Compound 5-1 was prepared by replacing the compound D1-1 in synthesis method of compound 1-1 with compound D1-3. Analysis data of 5-1: ¹H NMR (300 MHz, Chloroform-d) δ 5.05 (d, J=7.8 Hz, 1H), 4.29 (d, J=17.3 Hz, 2H), 4.05 (d, J=16.7 Hz, 1H), 3.87-3.64 (m, 2H), 3.45 (s, 1H), 3.18-2.96 (m, 2H), 1.91 (s, 4H), 1.42 (s, 9H).

Compound S5 was prepared by replacing the compound 1-1 in synthesis method of compound S1 with compound 5-1. Analysis data of S5: ¹H NMR (300 MHz, Chloroform-d) δ 10.49 (d, J=18.1 Hz, 1H), 8.44 (d, J=7.2 Hz, 1H), 7.89-7.55 (m, 3H), 7.33 (s, 2H), 7.07 (t, J=8.6 Hz, 1H), 5.15-4.75 (m, 2H), 4.54 (s, 2H), 4.27 (d, J=4.6 Hz, 2H), 3.73-3.23 (m, 3H), 2.08 (d, J=73.5 Hz, 5H), 1.62-1.05 (m, 14H).

6 Synthesis of Compound S6

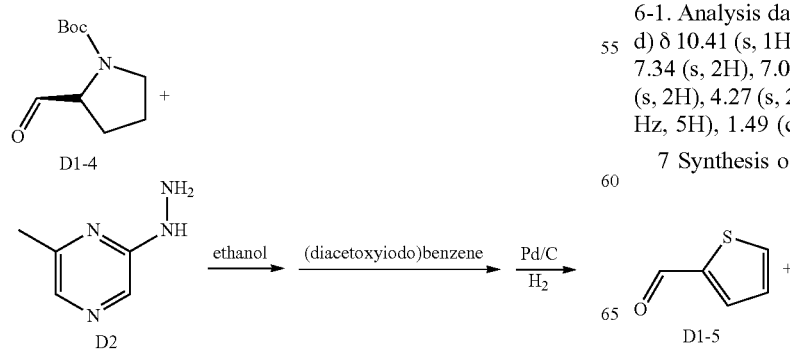

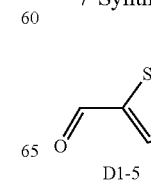

Compound 6-1 was prepared by replacing the compound D1-1 in synthesis method of compound 1-1 with compound D1-4. Analysis data of 6-1: ¹H NMR (300 MHz, Chloroform-d) δ 5.05 (d, J=7.8 Hz, 1H), 4.29 (d, J=17.3 Hz, 2H), 4.05 (d, J=16.7 Hz, 1H), 3.87-3.64 (m, 2H), 3.45 (s, 1H), 3.18-2.96 (m, 2H), 1.91 (s, 4H), 1.42 (s, 9H).

Compound S6 was prepared by replacing the compound 1-1 in synthesis method of compound S1 with compound 6-1. Analysis data of S6: ¹H NMR (300 MHz, Chloroform-d) δ 10.41 (s, 1H), 8.44 (d, J=7.4 Hz, 1H), 7.97-7.56 (m, 3H), 7.34 (s, 2H), 7.07 (t, J=9.1 Hz, 1H), 5.11-4.81 (m, 2H), 4.56 (s, 2H), 4.27 (s, 2H), 3.55 (d, J=46.4 Hz, 3H), 2.09 (d, J=72.1 Hz, 5H), 1.49 (q, J=48.1, 43.8 Hz, 14H).

7 Synthesis of Compound S7

8 Synthesis of Compound S8

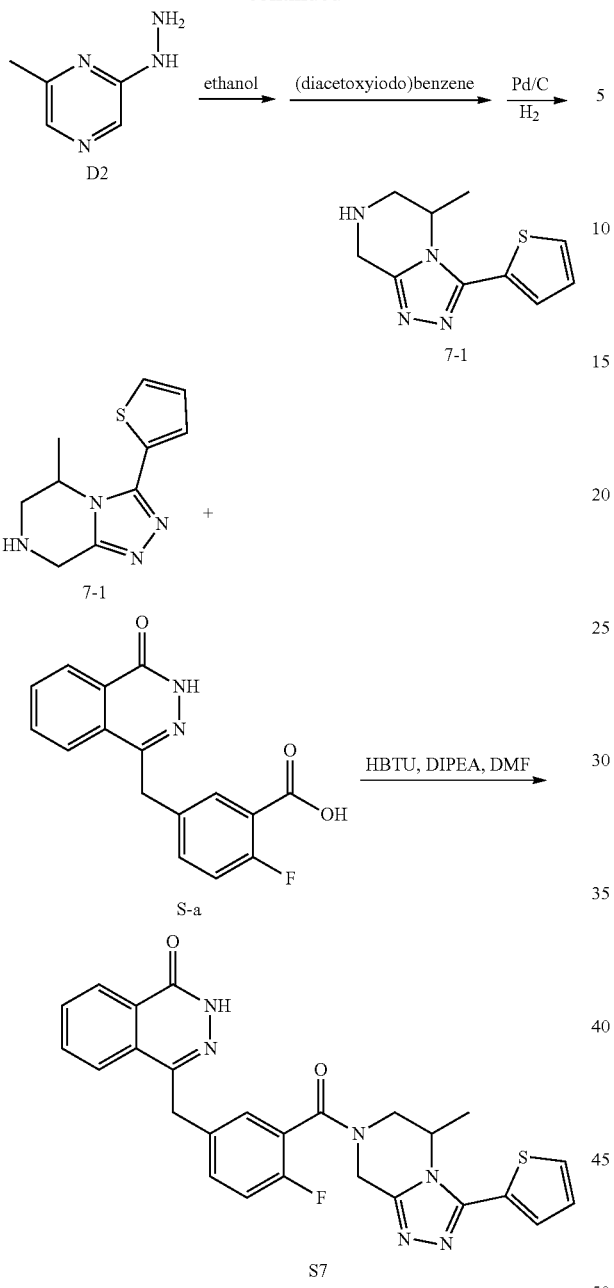

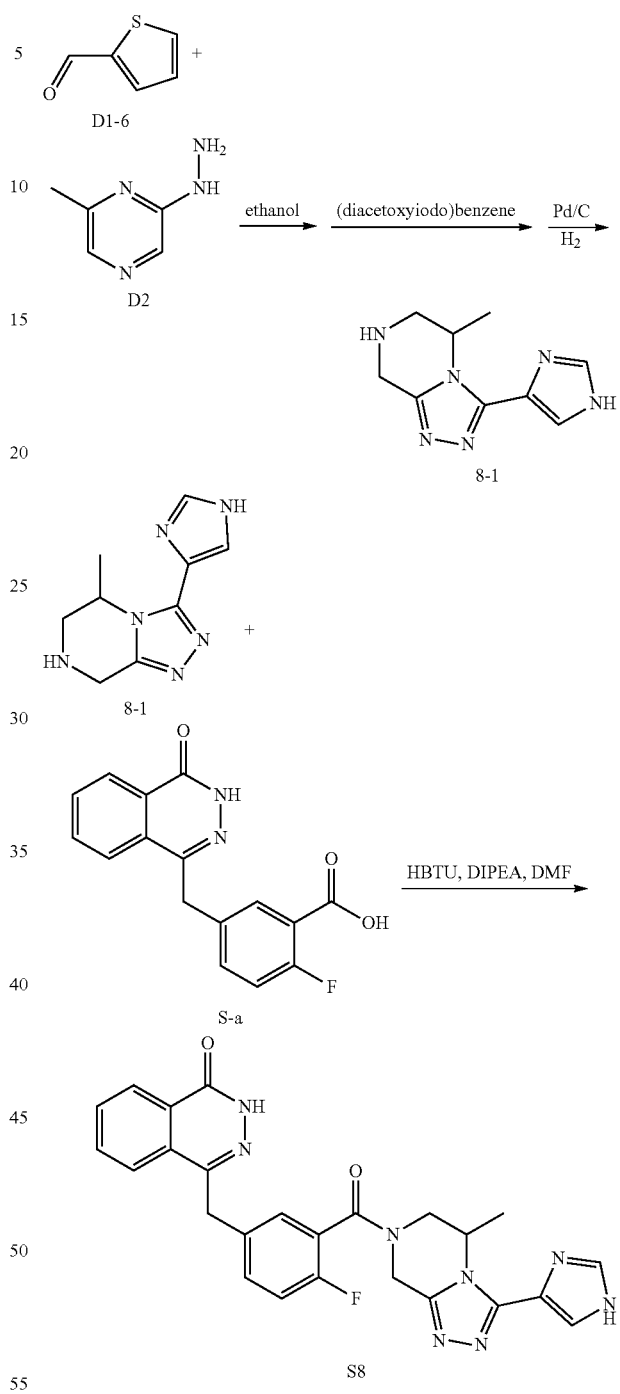

Compound 7-1 was prepared by replacing the compound DI-1 in synthesis method of compound 1-1 with compound DI-5. Analysis data of 7-1: ¹H NMR (300 MHz, Chloroform-d) δ 7.16 (ddt, J=4.8, 3.1, 1.6 Hz, 2H), 6.83 (td, J=3.5, 1.8 Hz, 1H), 4.26 (dd, J=8.1, 3.9 Hz, 1H), 4.02 (d, J=16.4 Hz, 1H), 3.79 (dd, J=16.7, 2.0 Hz, 1H), 3.15 (q, J=1.6 Hz, 2H), 3.05-2.90 (m, 1H), 2.77 (d, J=13.5 Hz, 1H), 1.06 (dd, J=6.5, 1.8 Hz, 3H).

Compound S7 was prepared by replacing the compound 1-1 in synthesis method of compound S1 with compound 7-1. Analysis data of S7: ¹H NMR (300 MHz, Chloroform-d) δ 11.02 (s, 1H), 8.44 (d, J=7.5 Hz, 1H), 7.87-7.64 (m, 3H), 7.62-7.30 (m, 4H), 7.25-6.95 (m, 2H), 5.08-4.51 (m, 4H), 4.28 (s, 2H), 3.47 (dd, J=13.7, 4.0 Hz, 1H), 1.43 (d, J=6.5 Hz, 3H).

Compound 8-1 was prepared by replacing the compound D1-1 in synthesis method of compound 1-1 with compound D1-6. Analysis data of 8-1: ¹H NMR (300 MHz, Chloroform-d) δ 11.38 (s, 1H), 8.47 (s, 1H), 7.69 (s, 1H), 4.38 (s, 1H), 4.28 (d, J=16.4 Hz, 1H), 4.04 (d, J=16.4 Hz, 1H), 3.65 (q, J=6.9 Hz, 1H), 3.21 (dd, J=13.4, 4.3 Hz, 1H), 3.03 (d, J=13.3 Hz, 1H), 1.33 (d, J=6.5 Hz, 3H).

Compound S8 was prepared by replacing the compound 1-1 in synthesis method of compound S1 with compound 8-1. Analysis data of S8: ¹H NMR (300 MHz, Chloroform-d) 511.38 (s, 1H), 10.98 (s, 1H), 8.39 (d, J=7.3 Hz, 1H), 7.71

(d, J=7.6 Hz, 4H), 7.30 (d, J=6.1 Hz, 1H), 7.05 (t, J=9.0 Hz, 1H), 5.50-5.19 (m, 1H), 4.89 (t, J=14.5 Hz, 1H), 4.57 (d, J=16.9 Hz, 1H), 4.24 (s, 2H), 3.58-3.37 (m, 1H), 1.19 (s, 3H).

9 Synthesis of Compound S9

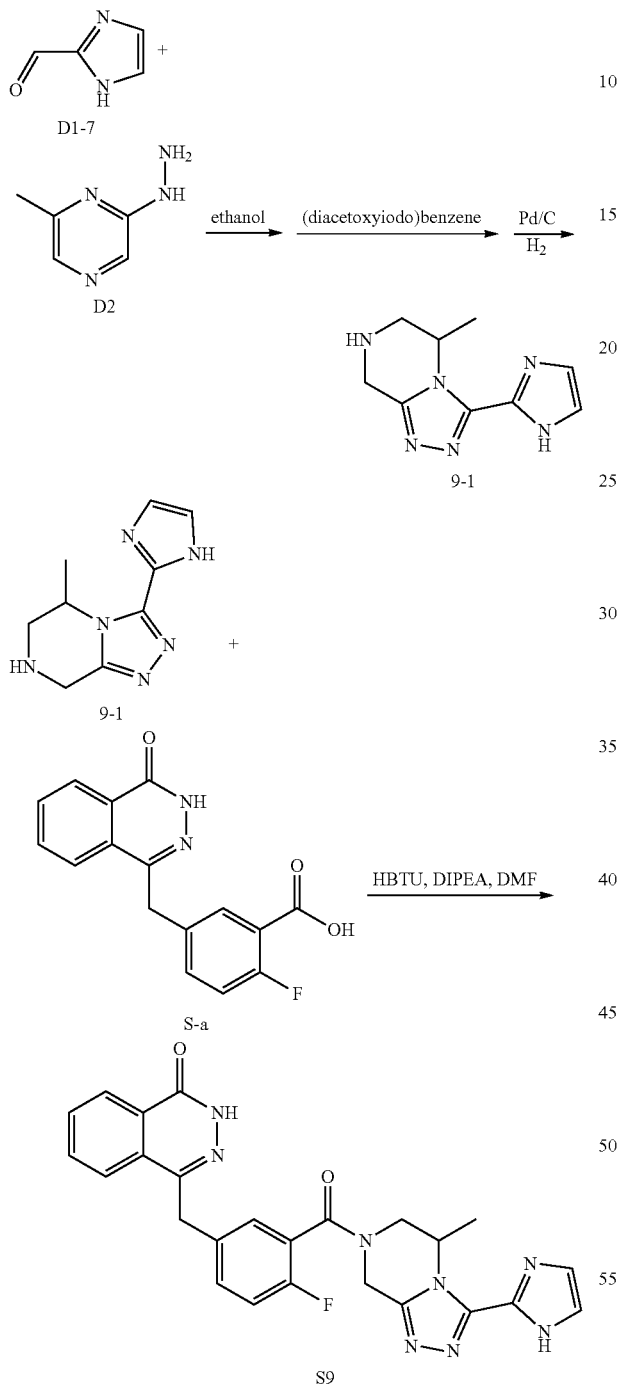

Compound 9-1 was prepared by replacing the compound D1-1 in synthesis method of compound 1-1 with compound D1-7. Analysis data of 9-1: 1H NMR (300 MHz, Chloroform-d) δ 11.38 (s, 1H), 7.70 (d, J=26.7 Hz, 2H), 4.38 (s, 1H), 4.28 (d, J=16.4 Hz, 1H), 4.04 (d, J=16.4 Hz, 1H), 3.65 (q, J=6.9 Hz, 1H), 3.21 (dd, J=13.4, 4.3 Hz, 1H), 3.03 (d, J=13.3 Hz, 1H), 1.33 (d, J=6.5 Hz, 3H).

Compound S9 was prepared by replacing the compound 1-1 in synthesis method of compound S1 with compound 9-1. Analysis data of S9: 1H NMR (300 MHz, Chloroform-d) δ 13.28 (s, 3H), 8.54-8.37 (m, 3H), 7.74 (dt, J=17.9, 5.3 Hz, 9H), 7.30 (d, J=22.8 Hz, 9H), 7.08 (t, J=8.6 Hz, 3H), 5.09-4.91 (m, 4H), 4.67 (d, J=16.9 Hz, 3H), 4.32 (s, 6H), 3.67 (d, J=15.9 Hz, 4H), 3.40 (d, J=13.7 Hz, 2H), 3.18-3.01 (m, 4H), 1.46 (s, 9H).

10 Synthesis of Compound S10

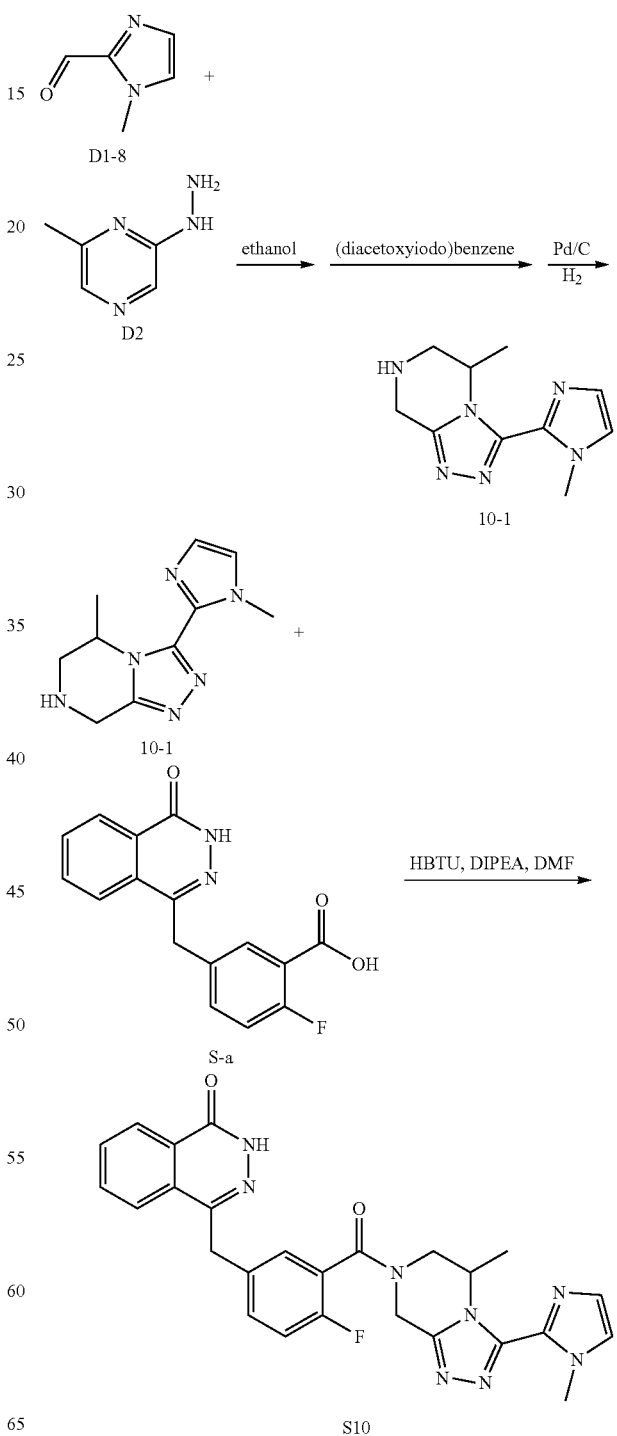

Compound 10-1 was prepared by replacing the compound D1-1 in synthesis method of compound 1-1 with compound D1-8. Analysis data of 10-1: ¹H NMR (300 MHz, Chloroform-d) δ 7.85 (s, 1H), 7.76 (s, 1H), 4.38 (s, 1H), 4.28 (d, J=16.4 Hz, 1H), 4.04 (d, J=16.4 Hz, 1H), 3.92 (d, J=1.3 Hz, 3H), 3.65 (q, J=6.9 Hz, 1H), 3.21 (dd, J=13.4, 4.3 Hz, 1H), 3.03 (d, J=13.3 Hz, 1H), 1.33 (d, J=6.5 Hz, 3H).

Compound S10 was prepared by replacing the compound 1-1 in synthesis method of compound S1 with compound 10-1. Analysis data of S10: ¹H NMR (300 MHz, Chloroform-d) δ 10.56 (s, 1H), 8.41 (dd, J=7.6, 1.8 Hz, 1H), 7.79-7.61 (m, 3H), 7.31 (d, J=6.3 Hz, 2H), 7.13-6.91 (m, 3H), 5.52 (s, 0.5H), 4.96-4.84 (m, 1H), 4.68-4.52 (m, 1H), 4.24 (s, 2H), 4.07 (d, J=3.4 Hz, 3H), 3.61 (s, 0.5H), 3.40-3.30 (m, 1H), 1.39 (d, J=6.5 Hz, 3H).

11 Synthesis of Compound S11

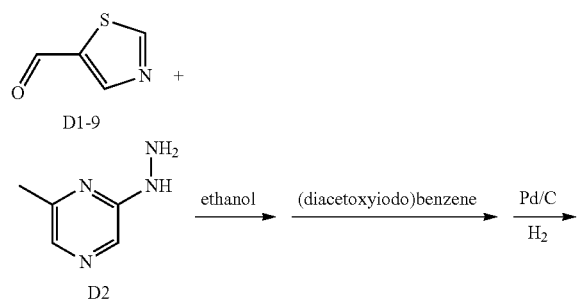

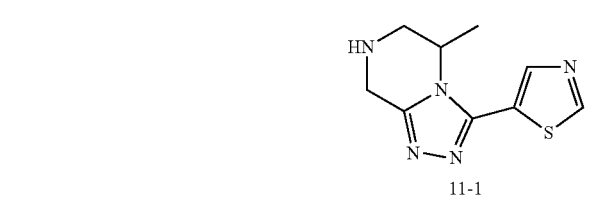

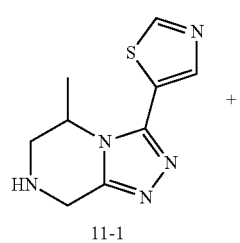

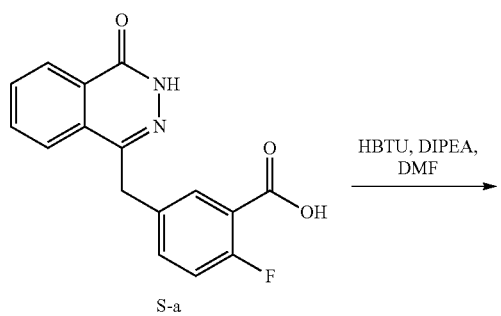

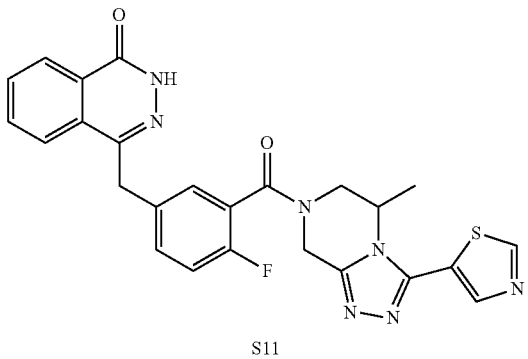

Compound 11-1 was prepared by replacing the compound D1-1 in synthesis method of compound 1-1 with compound D1-9. Analysis data of 11-1: ¹H NMR (300 MHz, Chloroform-d) δ 7.74-7.65 (m, 1H), 7.56-7.38 (m, 2H), 4.60-4.46 (m, 1H), 4.29 (d, J=16.4 Hz, 1H), 4.09 (d, J=16.4 Hz, 1H), 3.28 (dd, J=13.4, 4.3 Hz, 1H), 3.03 (dd, J=13.4, 2.8 Hz, 1H), 2.21 (d, J=27.6 Hz, 2H), 1.28 (d, J=6.5 Hz, 3H).

Compound S11 was prepared by replacing the compound 1-1 in synthesis method of compound S1 with compound 11-1. Analysis data of S11: ¹H NMR (300 MHz, Chloroform-d) δ 10.84 (d, J=61.1 Hz, 1H), 8.87 (d, J=16.6 Hz, 1H), 8.40 (d, J=7.6 Hz, 1H), 8.17 (d, J=33.4 Hz, 1H), 7.68 (dd, J=16.2, 7.5 Hz, 3H), 7.32 (s, 2H), 7.05 (t, J=8.8 Hz, 1H), 5.69 (d, J=18.3 Hz, 0.5H), 5.16-4.76 (m, 2H), 4.79-4.48 (m, 2H), 4.24 (s, 2H), 3.71 (s, 0.5H), 3.44 (d, J=13.7 Hz, 1H), 1.41 (d, J=6.6 Hz, 3H).

12 Synthesis of Compound S12

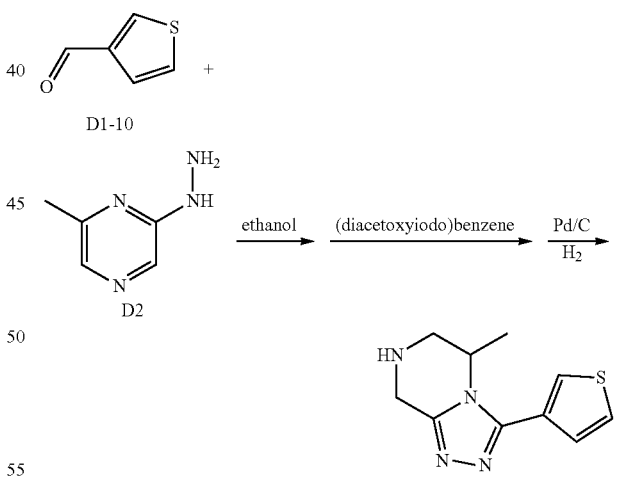

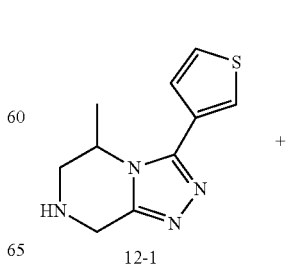

-continued

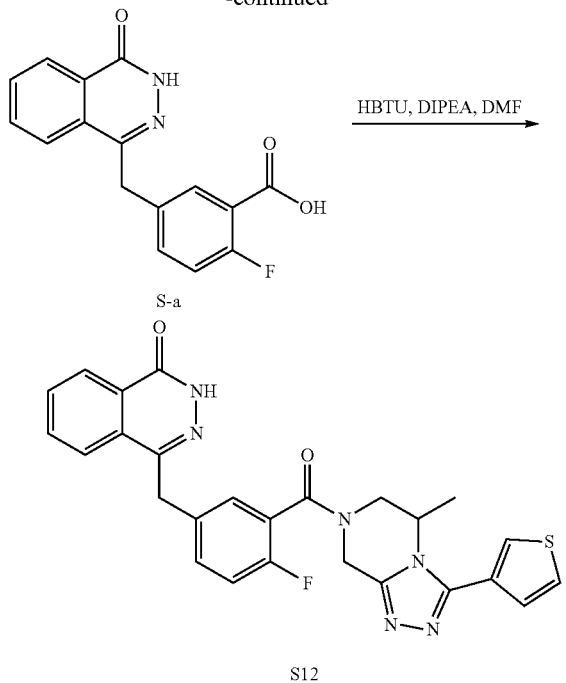

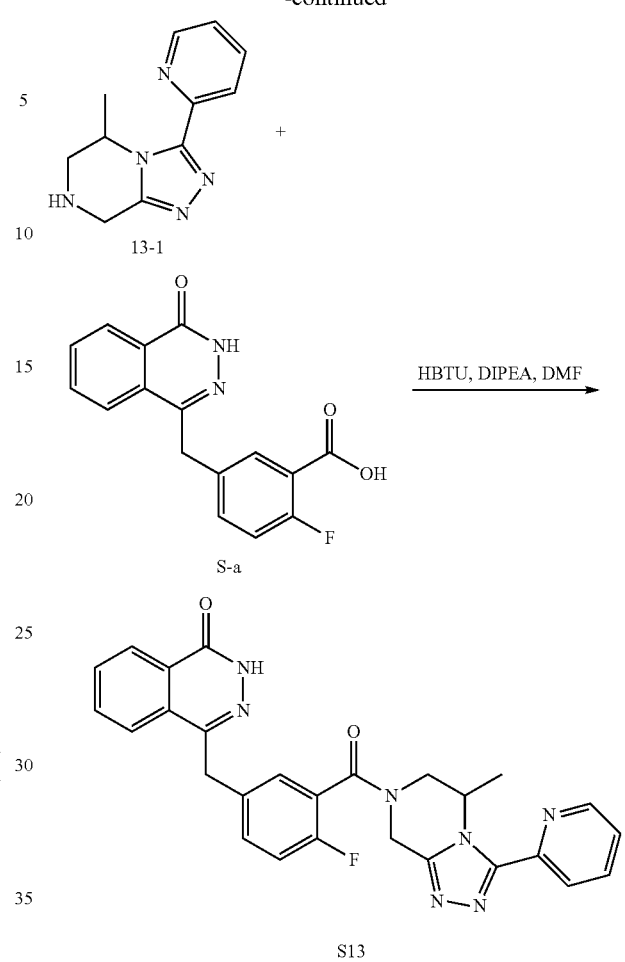

Compound 12-1 was prepared by replacing the compound D1-1 in synthesis method of compound 1-1 with compound DI-10. Analysis data of 12-1: $^1$H NMR (300 MHz, Chloroform-d) 7.85 (d, J=3.3 Hz, 1H), 7.37 (d, J=3.2 Hz, 1H), 5.18-5.01 (m, 1H), 4.36 (d, J=16.8 Hz, 1H), 4.09 (d, J=16.8 Hz, 1H), 3.26-3.01 (m, 2H), 1.86 (s, 2H), 1.44 (d, J=6.5 Hz, 3H).

Compound S12 was prepared by replacing the compound 1-1 in synthesis method of compound S1 with compound 12-1. Analysis data of S12: $^1$H NMR (300 MHz, Chloroform-d) δ 10.85 (d, J=51.2 Hz, 1H), 8.46 (d, J=7.5 Hz, 1H), 7.76 (dq, J=15.3, 8.4, 7.3 Hz, 4H), 7.60-7.28 (m, 4H), 7.10 (t, J=8.8 Hz, 1H), 5.64 (d, J=17.8 Hz, 0.5H), 4.99-4.62 (m, 3H), 4.30 (s, 2H), 3.71 (s, 0.5H), 3.62-3.43 (m, 1H), 1.39 (d, J=6.6 Hz, 3H).

13 Synthesis of Compound S13

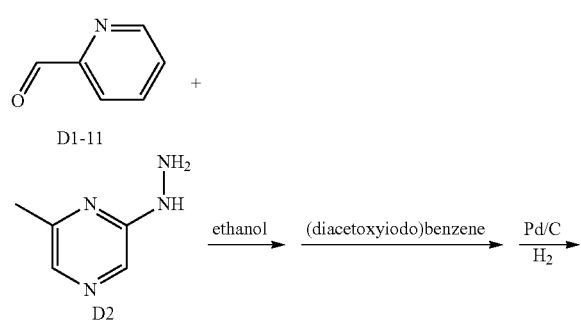

Compound 13-1 was prepared by replacing the compound D1-1 in synthesis method of compound 1-1 with compound DI-11. Analysis data of 13-1: $^1$H NMR (300 MHz, Chloroform-d) δ 7.50 (d, J=2.0 Hz, 1H), 7.20 (d, J=1.6 Hz, 1H), 7.00 (d, J=3.4 Hz, 1H), 6.50 (dd, J=3.4, 1.8 Hz, 1H), 4.68 (ddd, J=6.8, 4.4, 2.2 Hz, 1H), 4.27 (d, J=3.3 Hz, 1H), 4.03 (d, J=5.2 Hz, 1H), 3.64 (d, J=7.0 Hz, 1H), 3.17 (d, J=4.2 Hz, 1H), 3.03 (d, J=10.3 Hz, 1H), 1.34 (d, J=6.5 Hz, 3H).

Compound S13 was prepared by replacing the compound 1-1 in synthesis method of compound S1 with compound 13-1. Analysis data of S13: $^1$H NMR (300 MHz, DMSO-$d_6$) δ 12.60 (s, 1H), 8.69 (dd, J=19.2, 4.9 Hz, 1H), 8.22 (dd, J=19.7, 7.6 Hz, 2H), 7.91 (dt, J=41.6, 8.0 Hz, 4H), 7.57-7.38 (m, 3H), 7.29 (t, J=9.0 Hz, 1H), 5.50 (d, J=16.9 Hz, 1H), 5.26 (s, 1H), 4.87-4.54 (m, 2H), 4.36 (d, J=5.1 Hz, 2H), 3.87-3.73 (m, 1H), 3.56 (d, J=13.8 Hz, 1H), 1.42-1.04 (m, 3H).

14 Synthesis of Compound S14

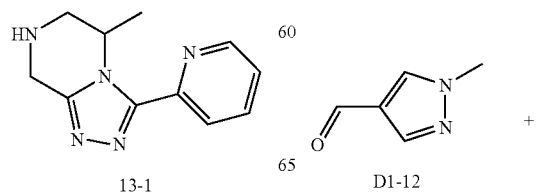

47
-continued

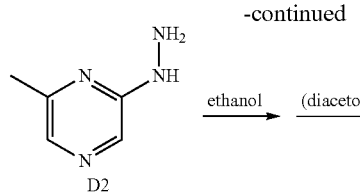

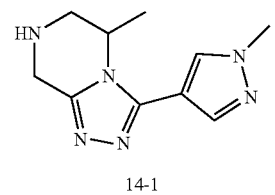

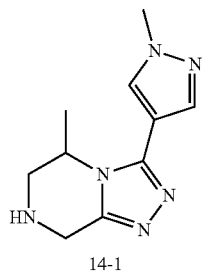

14-1

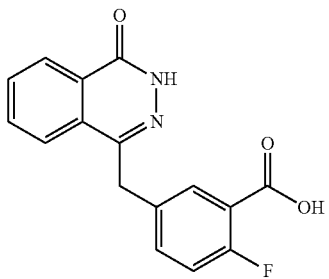

S-a

HBTU, DIPEA, DMF

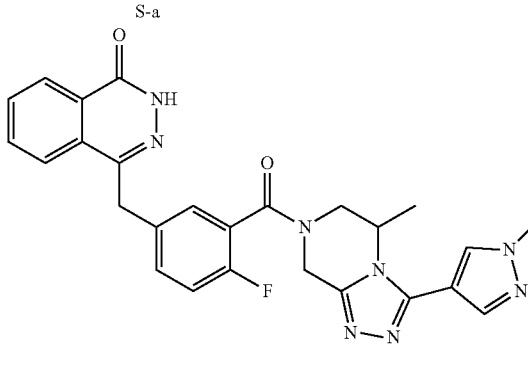

S14

Compound 14-1 was prepared by replacing the compound D1-1 in synthesis method of compound 1-1 with compound D1-12. Analysis data of 14-1: $^1$H NMR (300 MHz, Chloroform-d) δ 7.85 (s, 1H), 7.76 (s, 1H), 4.38 (s, 1H), 4.28 (d, J=16.4 Hz, 1H), 4.04 (d, J=16.4 Hz, 1H), 3.92 (d, J=1.3 Hz, 3H), 3.65 (q, J=6.9 Hz, 1H), 3.21 (dd, J=13.4, 4.3 Hz, 1H), 3.03 (d, J=13.3 Hz, 1H), 1.33 (d, J=6.5 Hz, 3H).

Compound S14 was prepared by replacing the compound 1-1 in synthesis method of compound S1 with compound 14-1. Analysis data of S14: $^1$H NMR (300 MHz, Chloroform-d) δ 10.74 (s, 1H), 8.45 (d, J=7.5 Hz, 1H), 8.09-7.64 (m, 5H), 7.35 (d, J=6.4 Hz, 2H), 7.10 (t, J=8.8 Hz, 1H), 5.71 (d, J=17.8 Hz, 0.5H), 5.03-4.84 (m, 2H), 4.62 (d, J=19.3 Hz, 2H), 4.30 (s, 2H), 3.98 (d, J=10.8 Hz, 3H), 3.71 (s, 0.5H), 3.56-3.41 (m, 1H), 1.43 (d, J=6.5 Hz, 2H), 1.22 (d, J=9.3 Hz, 1H).

48
15 Synthesis of Compound S15

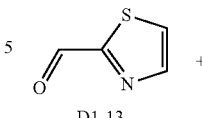

D1-13

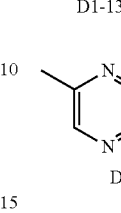

D2

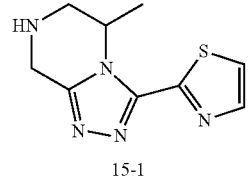

15-1

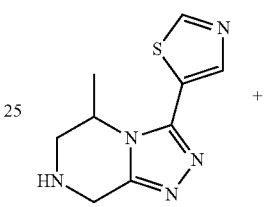

15-1

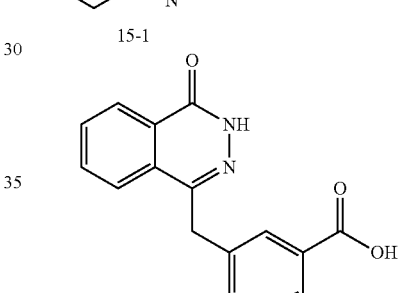

S-a

HBTU, DIPEA, DMF

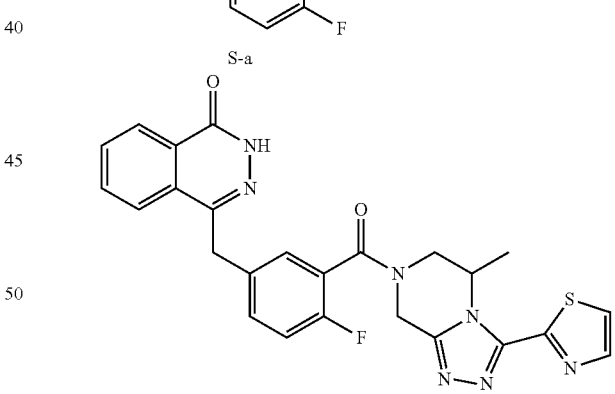

S15

Compound 15-1 was prepared by replacing the compound D1-1 in synthesis method of compound 1-1 with compound D1-13. Analysis data of 15-1: $^1$H NMR (300 MHz, Chloroform-d) δ 6.82 (s, 2H), 4.47 (dt, J=7.8, 4.3 Hz, 1H), 4.26 (d, J=16.2 Hz, 1H), 4.12 (d, J=16.1 Hz, 1H), 3.86 (d, J=3.9 Hz, 9H), 3.32 (dd, J=13.4, 4.5 Hz, 1H), 2.97 (dd, J=13.3, 3.5 Hz, 1H), 2.09 (s, 2H), 1.15 (d, J=6.5 Hz, 3H).

Compound S15 was prepared by replacing the compound 1-1 in synthesis method of compound S1 with compound 15-1. Analysis data of S15: $^1$H NMR (300 MHz, DMSO-d$_6$) δ 12.61 (s, 1H), 8.25 (d, J=7.7 Hz, 1H), 8.08 (dd, J=11.8, 3.3

Hz, 1H), 7.98-7.80 (m, 3H), 7.63-7.38 (m, 2H), 7.29 (t, J=9.2 Hz, 1H), 5.55 (d, J=17.7 Hz, 0.5H), 5.28 (s, 0.5H), 5.07 (s, 0.5H), 4.86-4.70 (m, 1H), 4.60 (d, J=17.9 Hz, 0.5H), 4.47-4.24 (m, 2H), 3.81 (d, J=12.8 Hz, 0.5H), 3.57 (t, J=15.0 Hz, 1H), 1.60-0.99 (m, 3H).

16 Synthesis of Compound S16

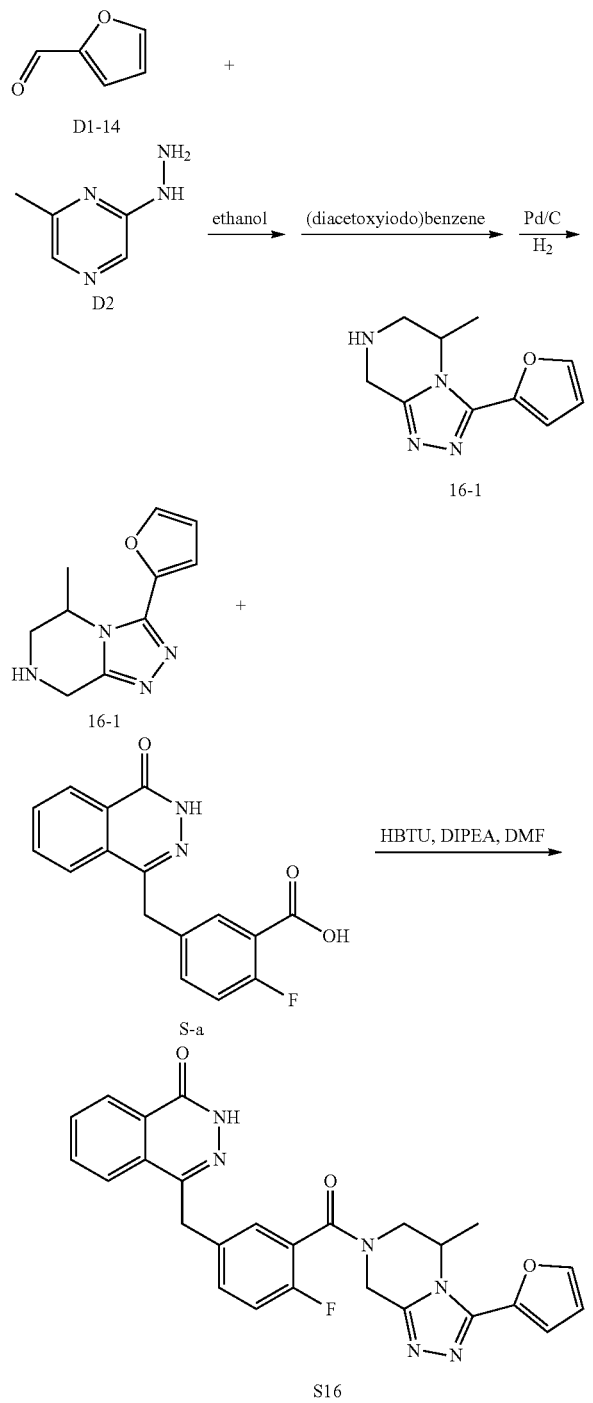

Compound 16-1 was prepared by replacing the compound D1-1 in synthesis method of compound 1-1 with compound D1-14. Analysis data of 16-1: $^1$H NMR (300 MHz, Chloroform-d) δ 8.25 (d, J=7.2 Hz, 1H), 7.30 (d, J=5.7 Hz, 1H), 6.65 (s, 1H), 4.26 (dd, J=8.1, 3.9 Hz, 1H), 4.02 (d, J=16.4 Hz, 1H), 3.79 (dd, J=16.7, 2.0 Hz, 1H), 3.15 (q, J=1.6 Hz, 2H), 3.05-2.90 (m, 1H), 2.77 (d, J=13.5 Hz, 1H), 1.06 (dd, J=6.5, 1.8 Hz, 3H).

Compound S16 was prepared by replacing the compound 1-1 in synthesis method of compound S1 with compound 16-1. Analysis data of S16: $^1$H NMR (300 MHz, Chloroform-d) δ 10.41 (s, 1H), 8.46 (d, J=7.1 Hz, 1H), 7.81-7.67 (m, 3H), 7.36 (d, J=5.7 Hz, 2H), 7.17-7.03 (m, 2H), 6.59 (s, 1H), 5.75 (d, J=17.9 Hz, 0.5H), 5.12-4.54 (m, 4H), 4.30 (s, 2H), 3.71 (s, 0.5H), 3.53-3.38 (m, 1H), 1.47 (d, J=6.5 Hz, 3H).

17 Synthesis of Compound S17

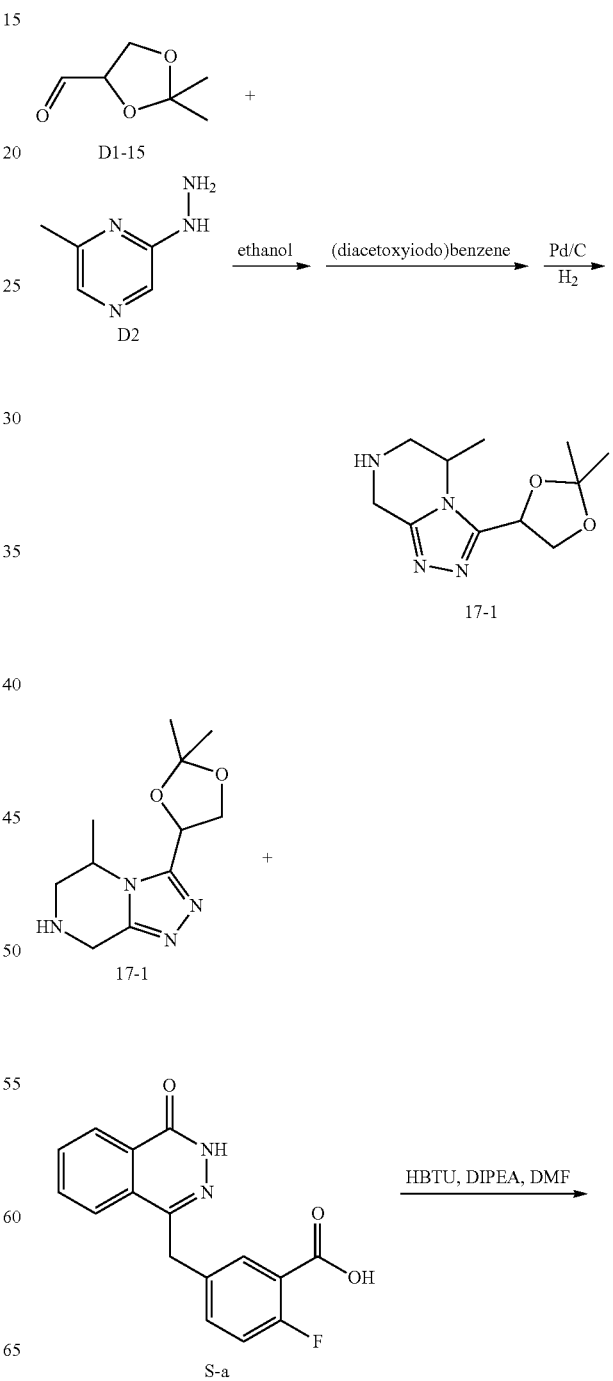

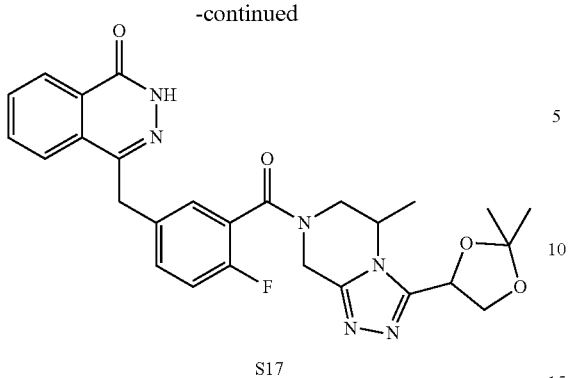

S17

Compound 17-1 was prepared by replacing the compound D1-1 in synthesis method of compound 1-1 with compound D1-15. Analysis data of 17-1: ¹H NMR (300 MHz, Chloroform-d) δ 4.70 (ddd, J=8.9, 7.5, 1.5 Hz, 1H), 4.30 (d, J=16.7 Hz, 1H), 4.08 (dd, J=16.7, 1.5 Hz, 1H), 3.14 (dd, J=13.4, 4.0 Hz, 1H), 3.04 (d, J=13.6 Hz, 1H), 1.56 (dd, J=6.6, 1.5 Hz, 3H), 1.43 (s, 6H).

Compound S17 was prepared by replacing the compound 1-1 in synthesis method of compound S1 with compound 17-1. Analysis data of S17: ¹H NMR (300 MHz, Chloroform-d) δ 10.63 (d, J=32.0 Hz, 1H), 8.52-8.35 (m, 1H), 7.90-7.61 (m, 3H), 7.46-7.29 (m, 2H), 7.15-7.01 (m, 1H), 5.61 (d, J=18.1 Hz, 0.5H), 5.14 (t, J=7.1 Hz, 1H), 4.97-4.59 (m, 4H), 4.40 (td, J=7.9, 6.7, 2.4 Hz, 1H), 4.28 (s, 2H), 3.63 (s, 0.5H), 3.35 (d, J=13.8 Hz, 1H), 1.64 (d, J=44.0 Hz, 3H), 1.53-1.32 (m, 6H).

18 Synthesis of Compound S18

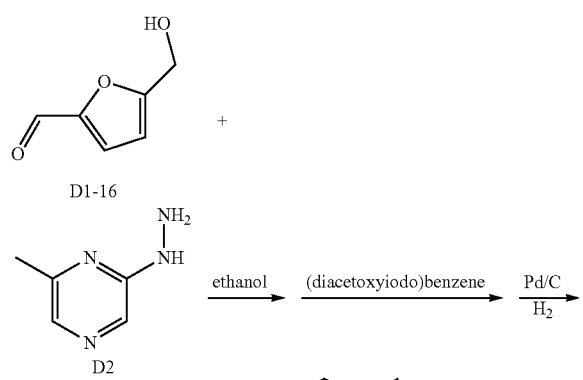

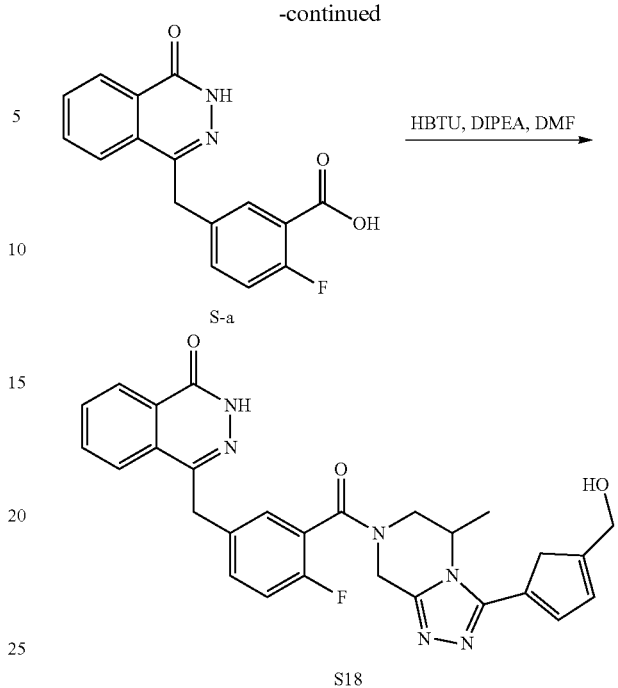

S18

Compound 18-1 was prepared by replacing the compound D1-1 in synthesis method of compound 1-1 with compound D1-16. Analysis data of 18-1: ¹H NMR (300 MHz, Chloroform-d) δ 6.92 (d, J=3.4 Hz, 1H), 6.40 (d, J=3.4 Hz, 1H), 4.72 (s, 1H), 4.66 (s, 2H), 4.31 (d, J=16.6 Hz, 1H), 4.08 (d, J=16.5 Hz, 1H), 3.47 (d, J=0.9 Hz, 1H), 3.24 (dd, J=13.5, 4.3 Hz, 1H), 3.06 (dd, J=13.2, 2.2 Hz, 1H), 1.39 (d, J=6.5 Hz, 3H).

Compound S18 was prepared by replacing the compound 1-1 in synthesis method of compound S1 with compound 18-1. Analysis data of S18: ¹H NMR (300 MHz, Chloroform-d) δ 11.11 (d, J=113.9 Hz, 1H), 8.38 (d, J=7.8 Hz, 1H), 7.69 (d, J=12.7 Hz, 3H), 7.30 (s, 2H), 7.13-6.86 (m, 2H), 6.34 (d, J=21.2 Hz, 1H), 5.61 (d, J=18.3 Hz, 0.5H), 5.00-4.52 (m, 4H), 4.23 (s, 2H), 3.56 (s, 0.5H), 3.39 (d, J=19.8 Hz, 1H), 2.79 (d, J=14.4 Hz, 1H), 1.51-1.07 (m, 3H).

19 Synthesis of Compound S19

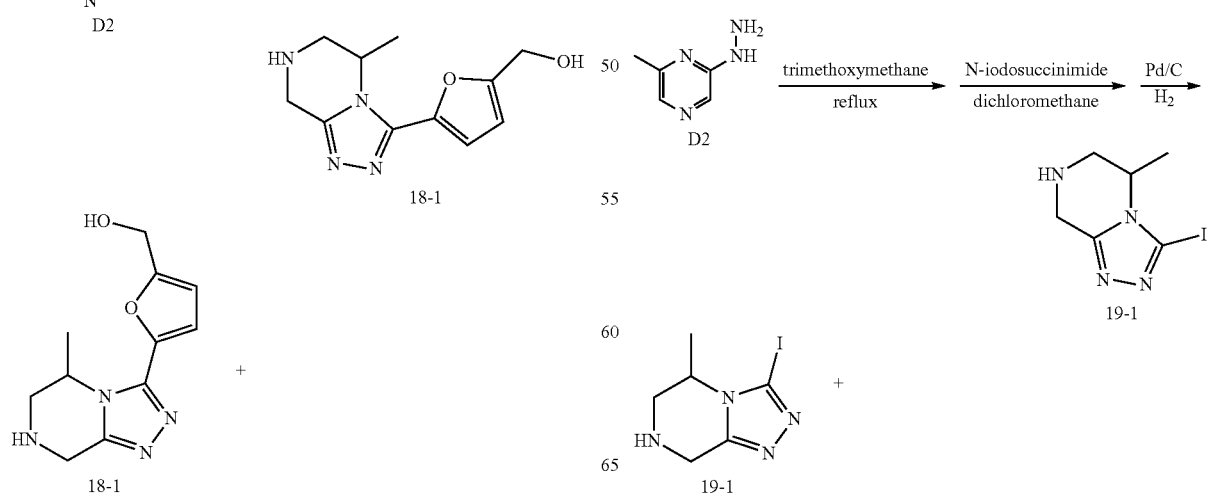

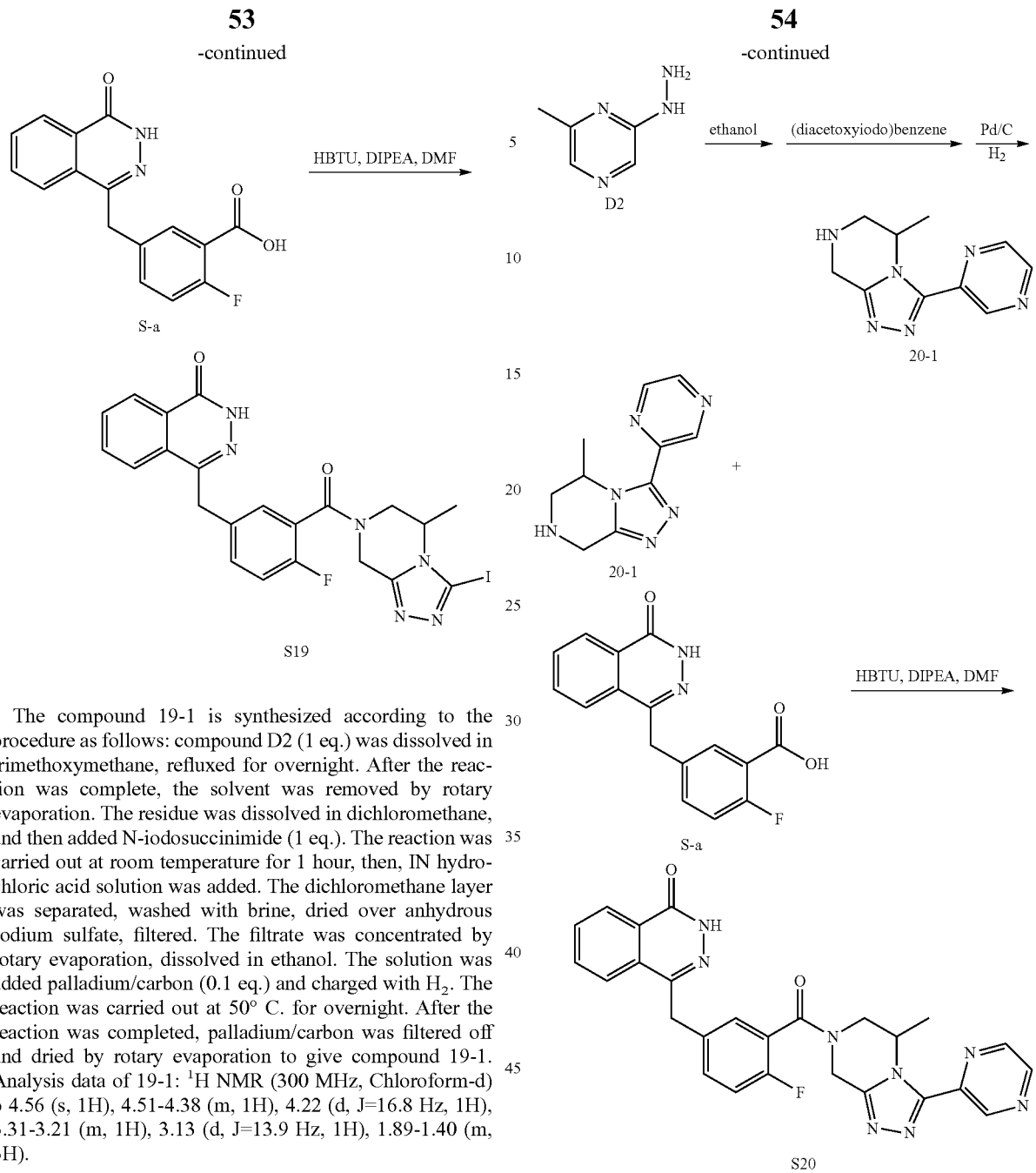

The compound 19-1 is synthesized according to the procedure as follows: compound D2 (1 eq.) was dissolved in trimethoxymethane, refluxed for overnight. After the reaction was complete, the solvent was removed by rotary evaporation. The residue was dissolved in dichloromethane, and then added N-iodosuccinimide (1 eq.). The reaction was carried out at room temperature for 1 hour, then, IN hydrochloric acid solution was added. The dichloromethane layer was separated, washed with brine, dried over anhydrous sodium sulfate, filtered. The filtrate was concentrated by rotary evaporation, dissolved in ethanol. The solution was added palladium/carbon (0.1 eq.) and charged with $H_2$. The reaction was carried out at 50° C. for overnight. After the reaction was completed, palladium/carbon was filtered off and dried by rotary evaporation to give compound 19-1. Analysis data of 19-1: $^1$H NMR (300 MHz, Chloroform-d) δ 4.56 (s, 1H), 4.51-4.38 (m, 1H), 4.22 (d, J=16.8 Hz, 1H), 3.31-3.21 (m, 1H), 3.13 (d, J=13.9 Hz, 1H), 1.89-1.40 (m, 3H).

Compound S19 was prepared by replacing the compound 1-1 in synthesis method of compound S1 with compound 19-1. Analysis data of S19: $^1$H NMR (300 MHz, Chloroform-d) δ 10.42 (d, J=43.6 Hz, 1H), 8.45 (d, J=6.7 Hz, 1H), 7.85-7.64 (m, 3H), 7.36 (dd, J=13.9, 4.8 Hz, 2H), 7.08 (t, J=8.9 Hz, 1H), 5.80 (d, J=17.8 Hz, 0.5H), 4.94 (t, J=16.2 Hz, 2H), 4.63-4.48 (m, 1H), 4.28 (s, 2H), 3.71 (s, 0.5H), 3.34 (d, J=14.0 Hz, 1H), 1.48 (d, J=6.6 Hz, 2H), 1.23 (s, 1H).

20 Synthesis of Compound S20

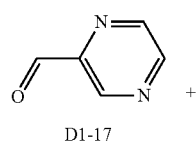

Compound 20-1 was prepared by replacing the compound D1-1 in synthesis method of compound 1-1 with compound D1-17. Analysis data of 20-1: 1H NMR (300 MHz, Chloroform-d) δ 9.50 (s, 1H), 8.59-8.65 (m, 2H), 5.18-5.01 (m, 1H), 4.36 (d, J=16.8 Hz, 1H), 4.09 (d, J=16.8 Hz, 1H), 3.26-3.01 (m, 2H), 1.44 (d, J=6.5 Hz, 3H).

Compound S20 was prepared by replacing the compound 1-1 in synthesis method of compound S1 with compound 20-1. Analysis data of S20:1H NMR (300 MHz, Chloroform-d) δ 10.82 (d, J=29.8 Hz, 1H), 9.59 (s, 1H), 8.88-8.34 (m, 3H), 7.94-7.62 (m, 3H), 7.38 (d, J=5.9 Hz, 2H), 7.11 (t, J=8.8 Hz, 1H), 5.80 (s, 0.5H), 5.55 (s, 1H), 4.99 (t, J=13.6 Hz, 1H), 4.69 (d, J=17.9 Hz, 1H), 4.31 (s, 2H), 3.73 (s, 0.5H), 3.54-3.39 (m, 1H), 1.47 (d, J=6.3 Hz, 2H), 1.26 (s, 1H).

21 Synthesis of Compound S21

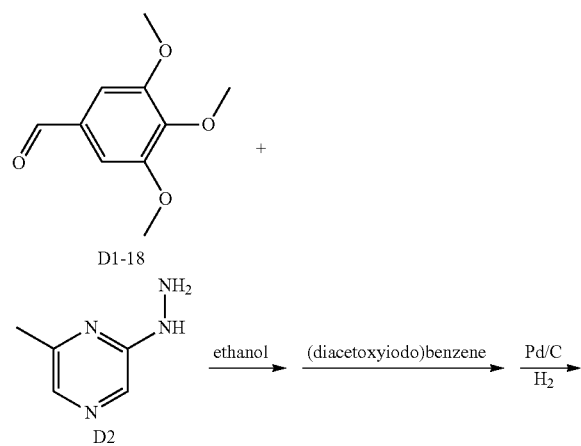

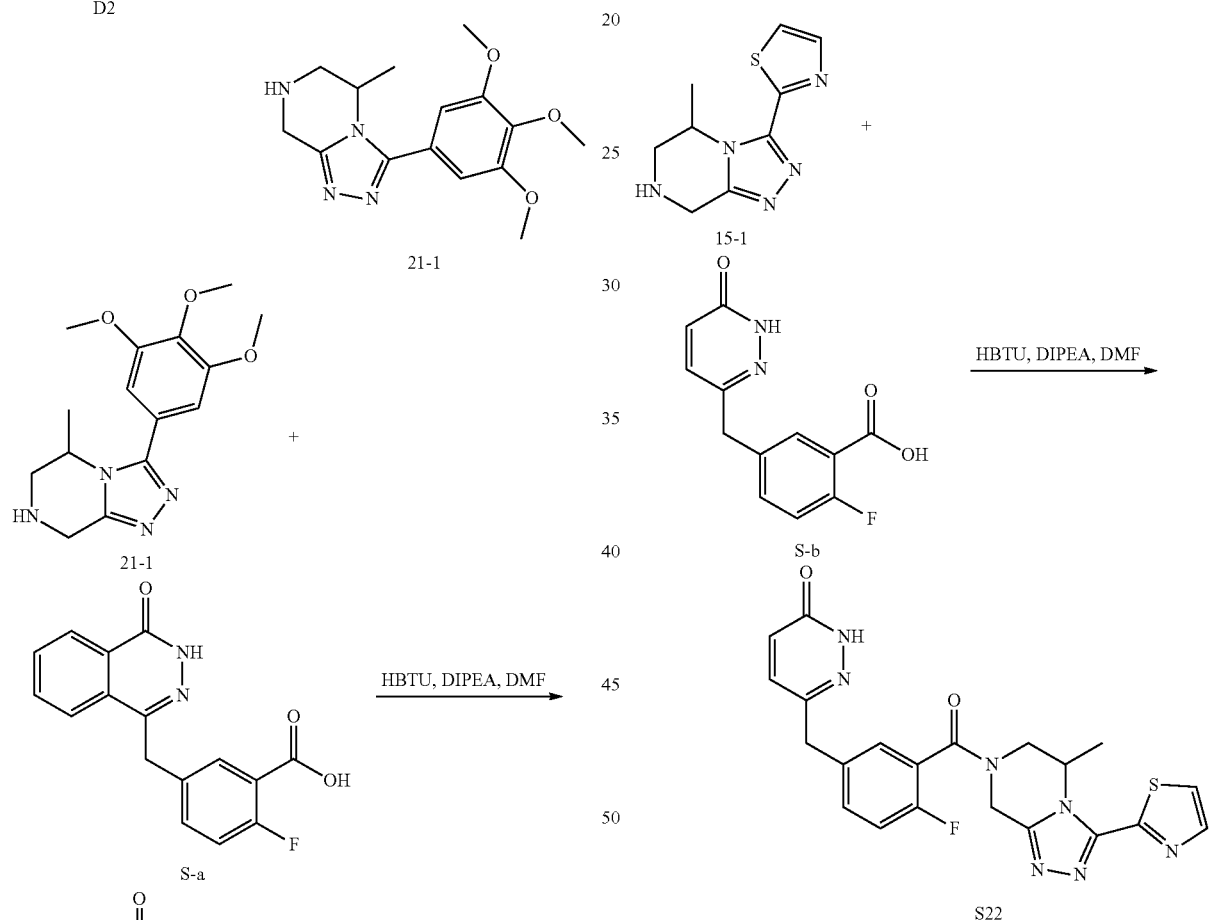

Compound 21-1 was prepared by replacing the compound D1-1 in synthesis method of compound 1-1 with compound DI-18. Analysis data of 21-1: $^1$H NMR (300 MHz, Chloroform-d) δ 6.82 (s, 2H), 4.47 (dt, J=7.8, 4.3 Hz, 1H), 4.26 (d, J=16.2 Hz, 1H), 4.12 (d, J=16.1 Hz, 1H), 3.86 (d, J=3.9 Hz, 9H), 3.32 (dd, J=13.4, 4.5 Hz, 1H), 2.97 (dd, J=13.3, 3.5 Hz, 1H), 1.15 (d, J=6.5 Hz, 3H).

Compound S21 was prepared by replacing the compound 1-1 in synthesis method of compound S1 with compound 21-1. Analysis data of S21: $^1$H NMR (300 MHz, Chloroform-d) δ 10.84 (d, J=33.7 Hz, 1H), 8.46 (d, J=7.4 Hz, 1H), 7.75 (dt, J=16.7, 8.0 Hz, 3H), 7.36 (d, J=6.1 Hz, 2H), 7.11 (t, J=8.7 Hz, 1H), 6.83 (d, J=10.7 Hz, 2H), 5.57 (d, J=18.0 Hz, 0.5H), 4.91 (d, J=16.7 Hz, 1H), 4.68 (d, J=16.7 Hz, 2H), 4.30 (s, 2H), 3.90 (d, J=3.3 Hz, 9H), 3.71 (d, J=16.2 Hz, 1.5H), 1.28 (d, J=6.5 Hz, 3H).

22 Synthesis of Compound S22

Compound S-b may be prepared using the methods described in *Bioorg. Med. Chem. Lett.* 2010. 20. 1100-1105.

Compound S22 was prepared by replacing the compound 1-1 in synthesis method of compound S1 with compound 15-1 and replacing the compound S-a with compound S-b. Analysis data of S22: $^1$H NMR (300 MHz, Chloroform-d) δ 11.96 (s, 1H), 7.88 (d, J=3.2 Hz, 1H), 7.41 (d, J=3.3 Hz, 1H), 7.26 (t, J=7.2 Hz, 2H), 7.06 (dd, J=9.3, 5.1 Hz, 2H), 6.83 (d, J=9.7 Hz, 1H), 5.77 (d, J=18.3 Hz, 0.5H), 5.40 (d, J=7.1 Hz, 1H), 5.27 (s, 0.5H), 4.93 (d, J=15.4 Hz, 1.5H), 4.65 (d, J=18.7 Hz, 1H), 3.86 (s, 2H), 3.69 (d, J=3.0 Hz, 0.5H), 3.34 (d, J=3.7 Hz, 1H), 1.47 (d, J=6.5 Hz, 3H).

23 Synthesis of Compound S23

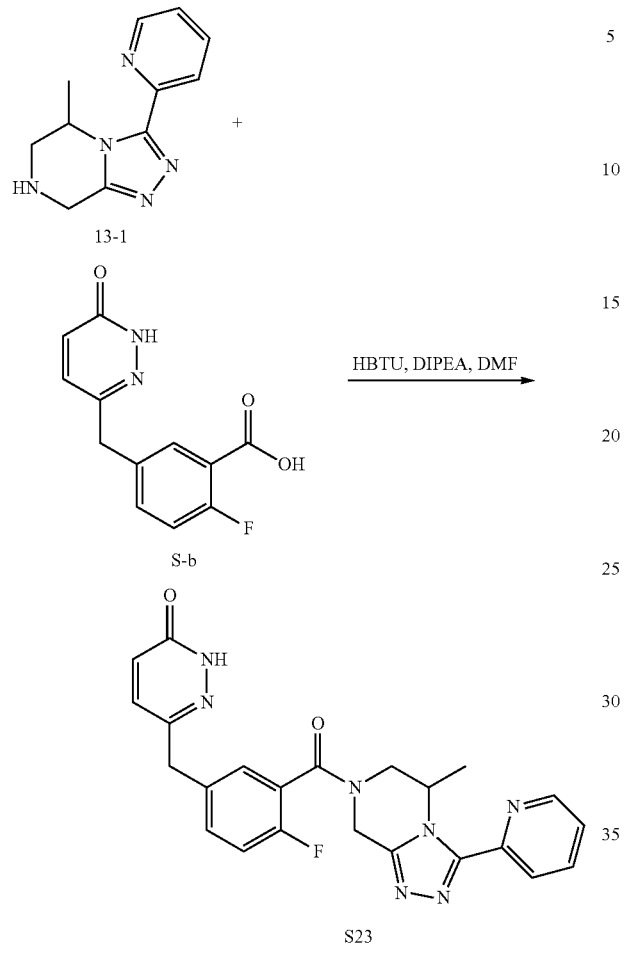

Compound S23 was prepared by replacing the compound 1-1 in synthesis method of compound S1 with compound 13-1, and replacing compound S-a with compound S-b. Analysis data of S23: $^1$H NMR (300 MHz, Chloroform-d) δ 12.01 (s, 1H), 8.58 (d, J=5.0 Hz, 1H), 8.24 (d, J=7.9 Hz, 1H), 7.76 (dd, J=8.8, 6.9 Hz, 1H), 7.27 (dt, J=14.5, 5.6 Hz, 2H), 7.05 (dt, J=7.9, 3.6 Hz, 2H), 6.83 (d, J=9.7 Hz, 1H), 5.68 (d, J=10.7 Hz, 0.5H), 4.91 (t, J=14.0 Hz, 1H), 4.65 (dd, J=17.6, 10.8 Hz, 1H), 3.86 (s, 2H), 3.67 (s, 0.5H), 3.39 (dd, J=13.8, 3.8 Hz, 1H), 1.39 (d, J=6.5 Hz, 3H).

24 Synthesis of Compound S24

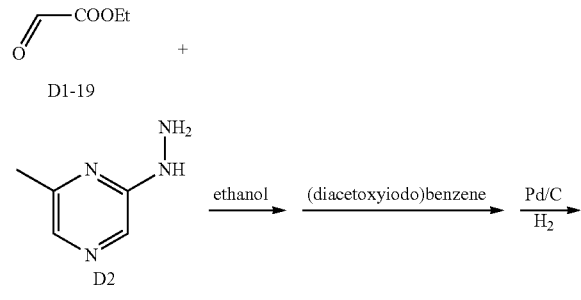

Compound 24-1 was prepared by replacing the compound D1-1 in synthesis method of compound 1-1 with compound D1-19. Analysis data of 24-1: $^1$H NMR (300 MHz, Chloroform-d) 65.09-5.01 (m, 1H), 4.36 (m, 3H), 4.11 (d, J=16.4 Hz, 1H), 3.22-3.01 (m, 2H), 1.87 (m, 2H), 1.45 (d, J=6.5 Hz, 3H), 1.33 (t, J=4.2 Hz, 3H).

Compound S24 was prepared by replacing the compound 1-1 in synthesis method of compound S1 with compound 24-1. Analysis data of S24: $^1$H NMR (300 MHz, DMSO-d$_6$) δ 12.59 (s, 1H), 8.36-8.10 (m, 1H), 8.04-7.68 (m, 3H), 7.44 (dd, J=32.6, 6.3 Hz, 2H), 7.30 (t, J=8.9 Hz, 1H), 5.50 (d, J=17.8 Hz, 0.5H), 5.03 (s, 0.5H), 4.90-4.51 (m, 2.5H), 4.37 (d, J=9.7 Hz, 4H), 3.66 (s, 0.5H), 3.53 (d, J=14.1 Hz, 1H), 1.51-1.26 (m, 4H), 1.08 (s, 2H).

25 Synthesis of Compound S25

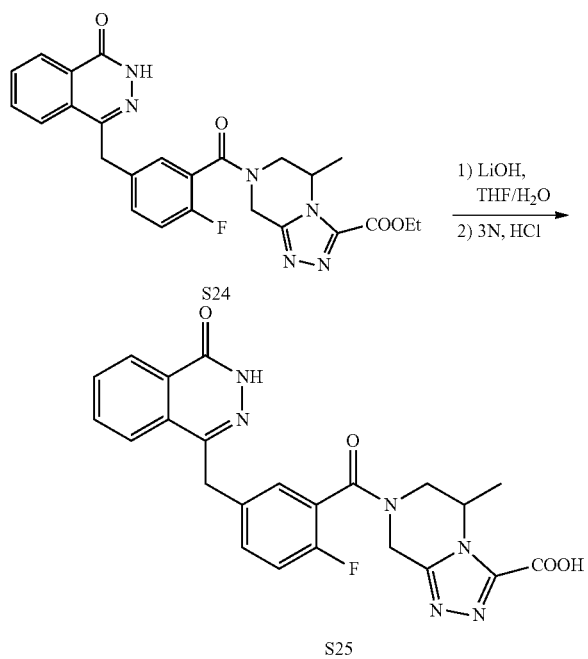

The compound S24 was dissolved in tetrahydrofuran and water, and then an aqueous solution of lithium hydroxide (4 eq) was added. The mixture was stirred at room temperature for overnight. After the reaction was determined to be completed by TLC, the pH was adjusted to 3 with 3N hydrochloric acid solution. A solid was precipitated, filtered off, washed with water and ethanol, dried to give compound S25 as a white solid. Analysis data of S25: $^1$H NMR (300 MHz, DMSO-d$_6$) δ 12.58 (s, 1H), 8.64 (d, J=6.5 Hz, 1H), 8.26 (d, J=7.6 Hz, 1H), 8.04-7.77 (m, 3H), 7.45 (s, 2H), 7.29 (d, J=10.0 Hz, 1H), 5.01 (s, 0.5H), 4.85 (s, 0.5H), 4.58 (s, 1H), 4.46 (s, 0.5H), 4.34 (s, 2H), 4.25 (s, 0.5H), 4.12 (s, 0.5H), 3.90-3.78 (m, 0.5H), 3.66 (d, J=13.9 Hz, 1H), 1.47-1.14 (m, 3H).

26 Synthesis of Compound S26

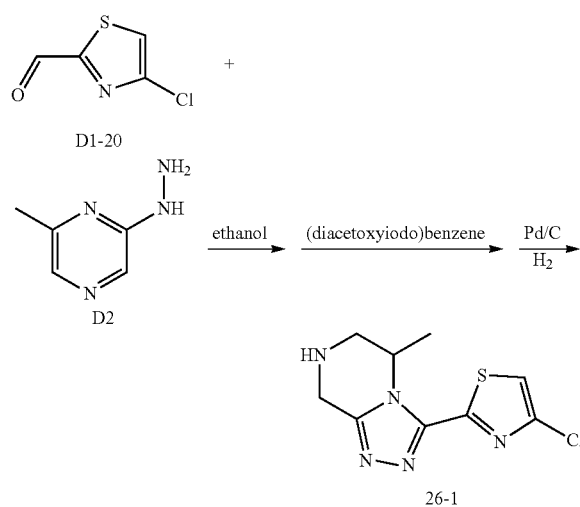

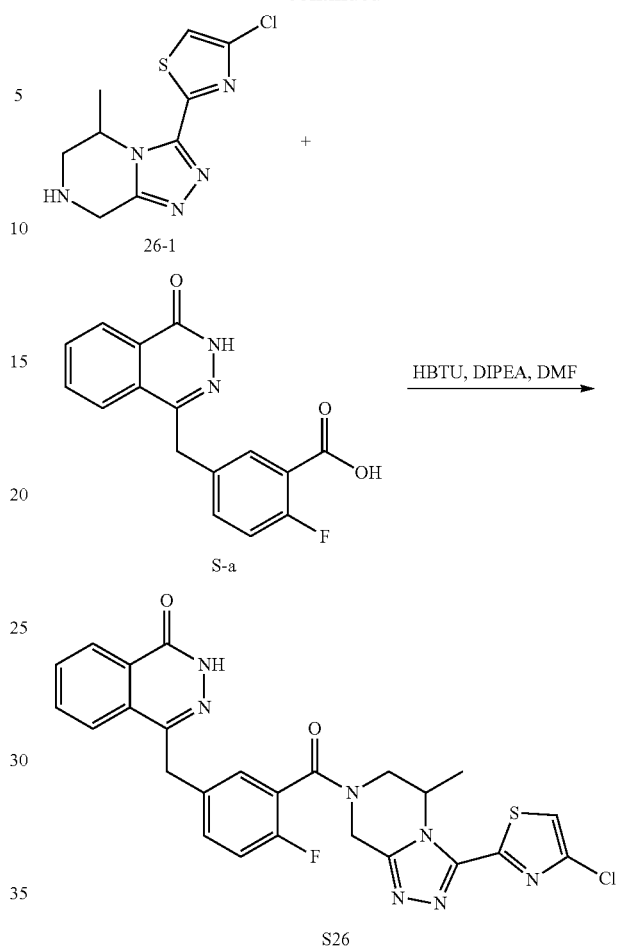

Compound 26-1 was prepared by replacing the compound D1-1 in synthesis method of compound 1-1 with compound DI-20. Analysis data of 26-1: $^1$H NMR (300 MHz, Chloroform-d) δ 7.87 (d, J=3.5 Hz, 1H), 5.09 (s, 1H), 4.43 (d, J=6.9 Hz, 1H), 4.29 (d, J=6.1 Hz, 1H), 3.12-2.99 (m, 1H), 2.90 (d, J=12.4 Hz, 1H), 1.38 (dd, J=5.7, 2.1 Hz, 3H).

Compound S26 was prepared by replacing the compound 1-1 in synthesis method of compound S1 with compound 26-1. Analysis data of S26: $^1$H NMR (300 MHz, Chloroform-d) δ 10.40 (s, 1H), 8.50-8.32 (m, 1H), 7.69-7.74 (m, 4H), 7.29 (d, J=5.4 Hz, 2H), 6.91 (t, J=7.2 Hz, 1H), 5.81 (d, J=18.3 Hz, 0.5H), 5.30 (s, 1H), 5.24 (s, 0.5H), 5.03-4.81 (m, 1H), 4.57 (t, J 19.4 Hz, 1H), 4.29 (s, 2H), 3.69 (s, 0.5H), 3.31 (s, 0.5H), 1.42 (d, J=6.5 Hz, 3H).

27 Synthesis of Compound S27

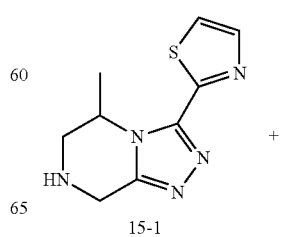

-continued

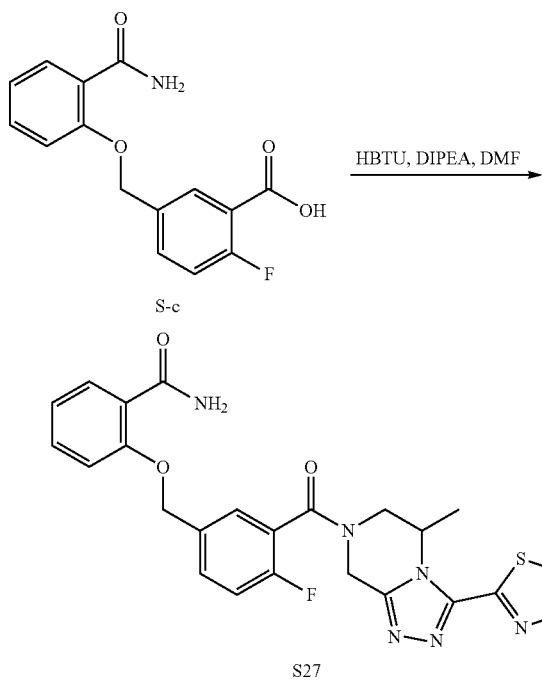

Compound S-c may be prepared using the methods described in *Bioorg. Med. Chem. Lett.* 2008. 18. 3942-3945

Compound S27 was prepared by replacing the compound 1-1 in synthesis method of compound S1 with compound 15-1, and replacing compound S-a with compound S-c. Analysis data of S27: ¹H NMR (300 MHz, Chloroform-d) δ 8.13 (d, J=7.5 Hz, 1H), 7.93-7.78 (m, 1H), 7.45 (ddt, J=14.7, 11.2, 6.7 Hz, 5H), 7.20-7.13 (m, 1H), 7.04 (t, J=7.6 Hz, 1H), 6.95 (d, J=8.4 Hz, 1H), 6.03-5.71 (m, 1H), 5.40 (d, J=7.4 Hz, 1H), 5.25 (s, 0.5H), 5.14 (d, J=3.9 Hz, 2H), 5.02-4.87 (m, 1H), 4.63 (dd, J=24.8, 17.8 Hz, 1H), 3.66 (d, J=15.5 Hz, 0.5H), 3.39 (dd, J=14.2, 3.7 Hz, 1H), 1.59-1.28 (m, 3H).

28 Synthesis of Compound S28

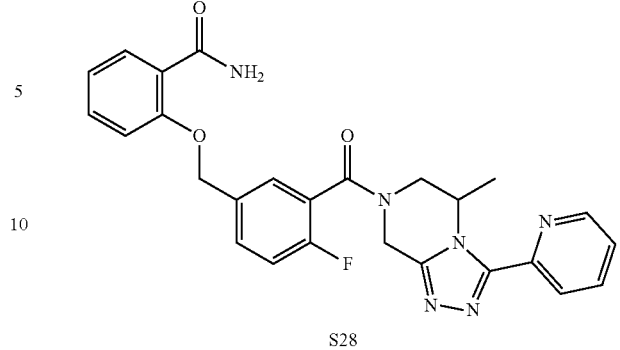

-continued

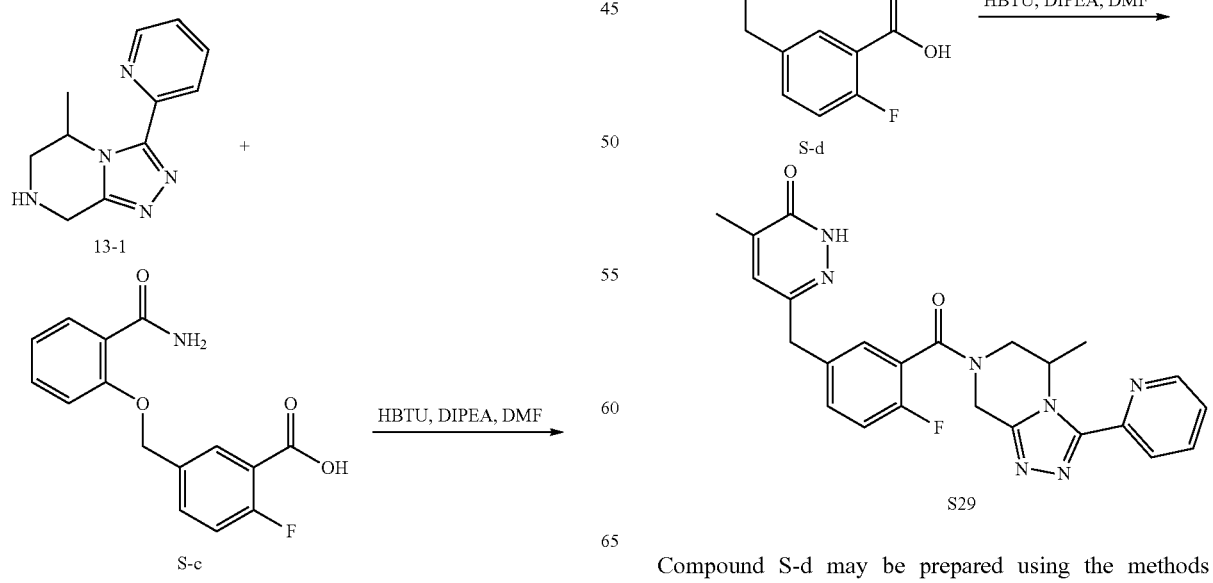

Compound S28 was prepared by replacing the compound 1-1 in synthesis method of compound S1 with compound 13-1, and replacing compound S-a with compound S-c. Analysis data of S28: ¹H NMR (300 MHz, Chloroform-d) δ 8.55 (d, J=28.1 Hz, 1H), 8.26 (d, J=8.0 Hz, 1H), 8.14 (d, J=7.6 Hz, 1H), 7.84-7.70 (m, 1H), 7.45 (dt, J=24.6, 8.6 Hz, 4H), 7.30 (t, J=6.3 Hz, 1H), 7.19 (d, J=9.2 Hz, 1H), 7.12-6.88 (m, 2H), 5.75 (d, J=37.6 Hz, 2.5H), 5.14 (d, J=3.2 Hz, 2H), 5.01-4.81 (m, 2H), 4.67 (dd, J=17.5, 10.8 Hz, 1H), 3.68 (d, J=11.3 Hz, 0.5H), 3.42 (dd, J=13.4, 4.2 Hz, 1H), 1.52-1.23 (m, 3H).

29 Synthesis of Compound S29

Compound S-d may be prepared using the methods described in *Bioorg. Med. Chem. Lett.* 2010. 20. 1100-1105.

Compound S29 was prepared by replacing the compound 1-1 in synthesis method of compound S1 with compound 13-1, and replacing compound S-a with compound S-d. Analysis data of S29: $^1$H NMR (300 MHz, Chloroform-d) δ 12.28 (s, 1H), 8.51 (dd, J=33.3, 4.9 Hz, 1H), 8.23 (t, J=7.5 Hz, 1H), 7.74 (t, J=7.9 Hz, 1H), 7.37-7.14 (m, 3H), 7.03 (t, J=8.8 Hz, 1H), 5.76-5.50 (m, 1H), 4.89 (t, J=14.0 Hz, 1.5H), 4.63 (dd, J=17.7, 11.0 Hz, 1H), 3.80 (s, 2H), 3.66 (s, 0.5H), 3.38 (q, J=6.6, 5.0 Hz, 1H), 2.07 (s, 3H), 1.31 (dd, J=41.6, 6.5 Hz, 3H).

30 Synthesis of Compound S30

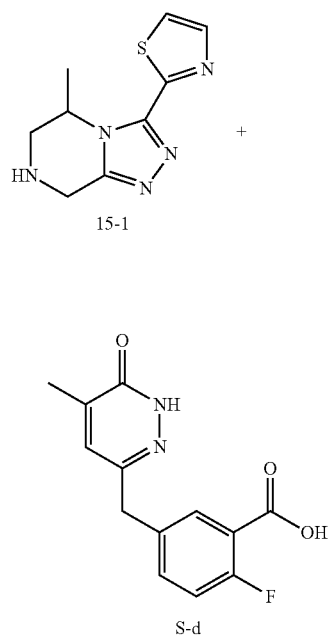

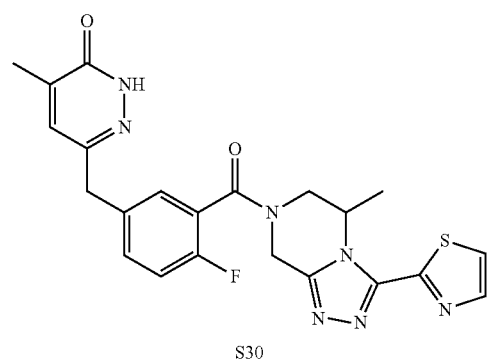

Compound S30 was prepared by replacing the compound 1-1 in synthesis method of compound S1 with compound 15-1, and replacing compound S-a with compound S-d. Analysis data of S30: $^1$H NMR (300 MHz, Chloroform-d) δ 12.14 (s, 1H), 7.83 (dd, J=26.0, 3.2 Hz, 1H), 7.39 (dd, J=8.0, 3.4 Hz, 1H), 7.31-7.18 (m, 2H), 7.04 (t, J=8.7 Hz, 1H), 6.89 (d, J=1.5 Hz, 1H), 5.76 (d, J=18.3 Hz, 0.5H), 5.44-5.20 (m, 1H), 4.92 (d, J=15.5 Hz, 2H), 4.72-4.51 (m, 1H), 3.81 (s, 2H), 3.69 (s, 0.5H), 3.42-3.32 (m, 1H), 2.08 (d, J=1.2 Hz, 3H), 1.46 (d, J=6.5 Hz, 3H).

31 Synthesis of Compound S31

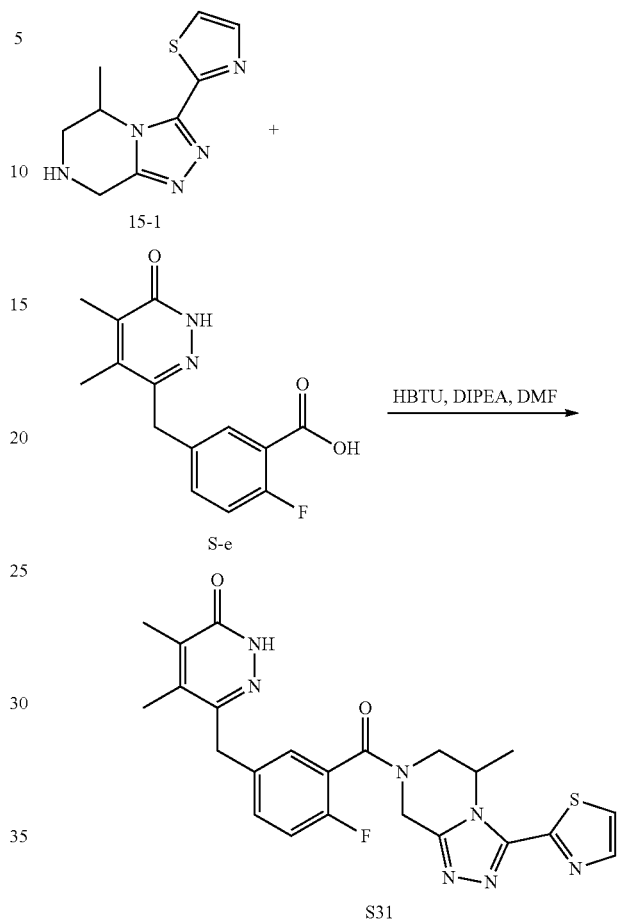

Compound S-e may be prepared using the methods described in *Bioorg. Med. Chem. Lett.* 2010. 20. 1100-1105.

Compound S31 was prepared by replacing the compound 1-1 in synthesis method of compound S1 with compound 15-1, and replacing compound S-a with compound S-e. Analysis data of S31: $^1$H NMR (300 MHz, Chloroform-d) δ 11.54 (d, J=63.5 Hz, 1H), 7.89 (d, J=3.0 Hz, 1H), 7.42 (d, J=3.1 Hz, 1H), 7.20 (s, 2H), 7.04 (t, J=8.7 Hz, 1H), 5.78 (d, J=18.4 Hz, 0.5H), 5.32 (d, J=49.4 Hz, 1H), 4.94 (d, J=15.5 Hz, 1H), 4.62 (t, J=16.3 Hz, 1H), 3.90 (s, 2H), 3.70 (s, 0.5H), 3.36 (d, J=14.0 Hz, 1H), 2.04 (d, J=23.2 Hz, 6H), 1.48 (d, J=6.4 Hz, 3H).

32 Synthesis of Compound S32

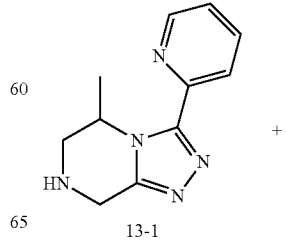

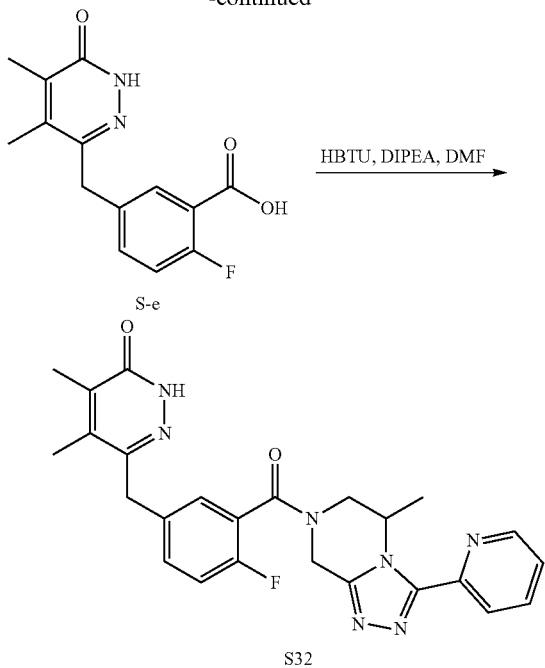

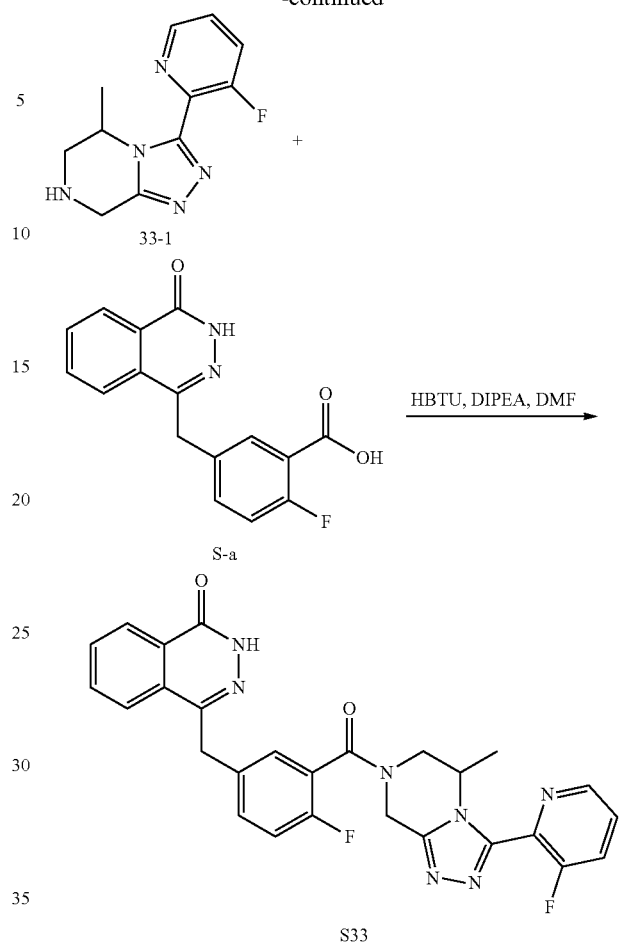

Compound S32 was prepared by replacing the compound 1-1 in synthesis method of compound S1 with compound 13-1, and replacing compound S-a with compound S-e. Analysis data of S32: $^1$H NMR (300 MHz, Chloroform-d) δ 11.34 (s, 1H), 8.54 (d, J=30.9 Hz, 1H), 8.26 (d, J=8.4 Hz, 1H), 7.77 (t, J=8.0 Hz, 1H), 7.25 (d, J=19.7 Hz, 2H), 7.04 (t, J=8.8 Hz, 1H), 5.68 (s, 1H), 4.91 (t, J=13.4 Hz, 1.5H), 4.76-4.57 (m, 1H), 3.90 (s, 2H), 3.68 (s, 0.5H), 3.39 (d, J=13.8 Hz, 1H), 2.04 (d, J=23.3 Hz, 6H), 1.40 (d, J=6.4 Hz, 3H).

33 Synthesis of Compound S33

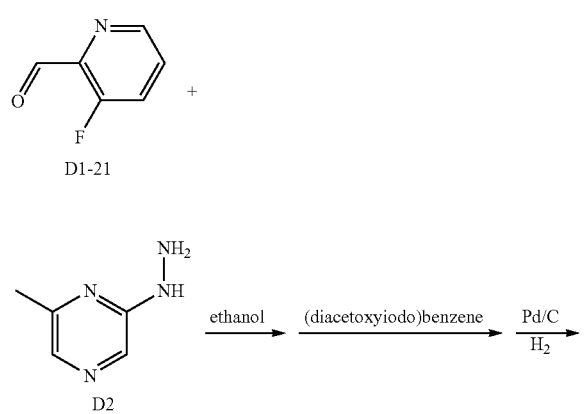

Compound 33-1 was prepared by replacing the compound D-1 in synthesis method of compound S1 with compound DI-21. Analysis data of 33-1: $^1$H NMR (300 MHz, Chloroform-d) δ $^1$H NMR (300 MHz, Chloroform-d) δ 8.43 (d, J=4.5 Hz, 1H), 7.55 (dd, J=10.0, 8.3 Hz, 1H), 7.41-7.26 (m, 1H), 5.09 (dt, J=6.7, 3.3 Hz, 1H), 4.33 (d, J=16.6 Hz, 1H), 4.13 (d, J=16.6 Hz, 1H), 3.24 (dd, J=13.5, 4.4 Hz, 1H), 2.98 (dd, J=13.5, 2.7 Hz, 1H), 1.19 (d, J=6.8 Hz, 3H).

Compound S33 was prepared by replacing the compound 1-1 in synthesis method of compound S1 with compound 33-1. Analysis data of S33: $^1$H NMR (300 MHz, Chloroform-d) δ 10.65 (d, J=12.4 Hz, 1H), 8.43 (dd, J=19.3, 6.1 Hz, 2H), 7.87-7.52 (m, 4H), 7.45-7.26 (m, 3H), 7.04 (t, J=8.9 Hz, 1H), 5.68 (d, J=17.6 Hz, 0.5H), 5.45 (s, 1H), 5.25 (s, 1H), 4.94 (d, J=17.1 Hz, 1H), 4.86-4.61 (m, 2H), 4.24 (s, 2H), 3.65 (s, 0.5H), 3.46 (d, J=14.1 Hz, 1H), 1.32 (d, J=6.5 Hz, 3H).

34 Synthesis of Compound S34

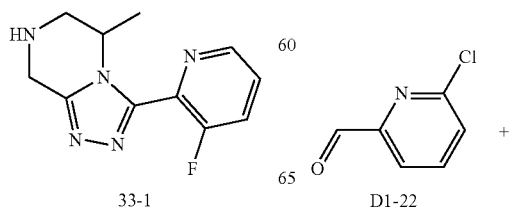

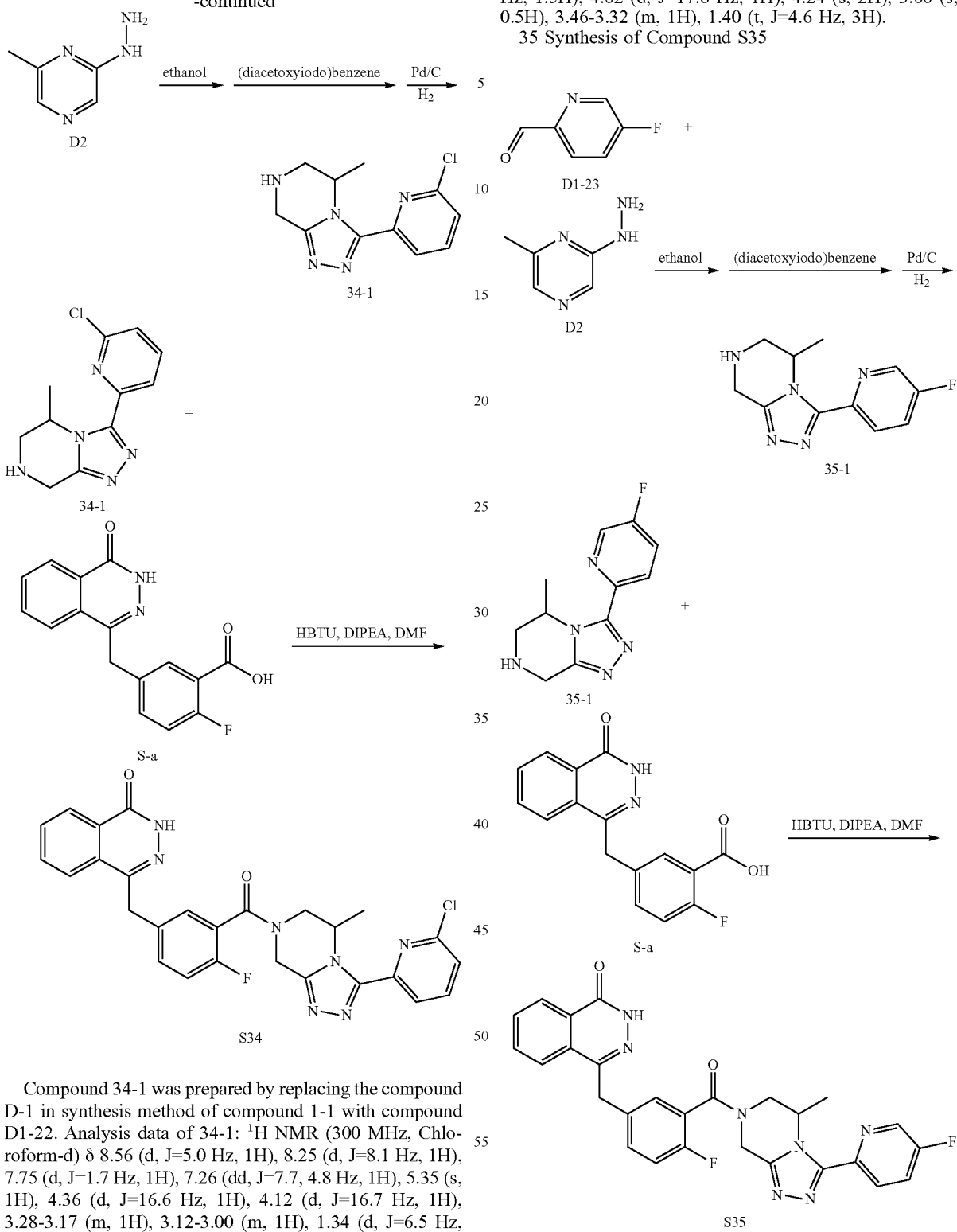

Compound 34-1 was prepared by replacing the compound D-1 in synthesis method of compound 1-1 with compound D1-22. Analysis data of 34-1: ¹H NMR (300 MHz, Chloroform-d) δ 8.56 (d, J=5.0 Hz, 1H), 8.25 (d, J=8.1 Hz, 1H), 7.75 (d, J=1.7 Hz, 1H), 7.26 (dd, J=7.7, 4.8 Hz, 1H), 5.35 (s, 1H), 4.36 (d, J=16.6 Hz, 1H), 4.12 (d, J=16.7 Hz, 1H), 3.28-3.17 (m, 1H), 3.12-3.00 (m, 1H), 1.34 (d, J=6.5 Hz, 3H).

Compound S34 was prepared by replacing the compound 1-1 in synthesis method of compound S1 with compound 34-1. Analysis data of S34: ¹H NMR (300 MHz, Chloroform-d) δ 10.87 (d, J=22.5 Hz, 1H), 8.58 (d, J=4.9 Hz, 1H), 8.40 (d, J=7.3 Hz, 1H), 8.23 (dd, J=14.8, 7.0 Hz, 1H), 7.71 (tt, J=12.5, 7.2 Hz, 4H), 7.32 (d, J=7.5 Hz, 3H), 7.03 (t, J=9.1 Hz, 1H), 5.66 (s, 0.5H), 5.48 (s, 0.5H), 4.90 (t, J=14.1 Hz, 1.5H), 4.62 (d, J=17.8 Hz, 1H), 4.24 (s, 2H), 3.66 (s, 0.5H), 3.46-3.32 (m, 1H), 1.40 (t, J=4.6 Hz, 3H).

35 Synthesis of Compound S35

Compound 35-1 was prepared by replacing the compound D-1 in synthesis method of compound 1-1 with compound D1-23. Analysis data of 35-1: ¹H NMR (300 MHz, Chloroform-d) δ 8.84 (d, J=2.3 Hz, 1H), 8.70-8.61 (m, 1H), 8.53 (d, J=2.8 Hz, OH), 7.98 (dt, J=7.9, 2.0 Hz, 1H), 7.76 (dt, J=8.8, 2.3 Hz, OH), 7.39 (dd, J=7.9, 4.9 Hz, 1H), 4.48 (tt, J=6.6, 3.9 Hz, 1H), 4.27 (dd, J=16.4, 2.6 Hz, 1H), 4.12 (d, J=16.3 Hz, 1H), 3.30 (ddd, J=13.4, 4.5, 2.6 Hz, 1H), 2.98 (ddd, J=13.5, 5.7, 3.5 Hz, 1H), 1.19-1.10 (m, 3H).

Compound S35 was prepared by replacing the compound 1-1 in synthesis method of compound S1 with compound 35-1. Analysis data of S35: ¹H NMR (300 MHz, Chloroform-d) δ 10.25 (s, 1H), 8.80-8.49 (m, 2H), 8.40 (d, J=7.5 Hz, 1H), 7.88-7.56 (m, 4H), 7.31 (d, J=6.3 Hz, 2H), 7.07 (t, J=8.9 Hz, 1H), 4.93-4.57 (m, 3.5H), 4.24 (s, 2H), 3.62 (d, J=13.0 Hz, 2H), 2.91 (d, J=48.3 Hz, 1.5H), 1.27 (d, J=6.5 Hz, 3H).

36 Synthesis of Compound S36

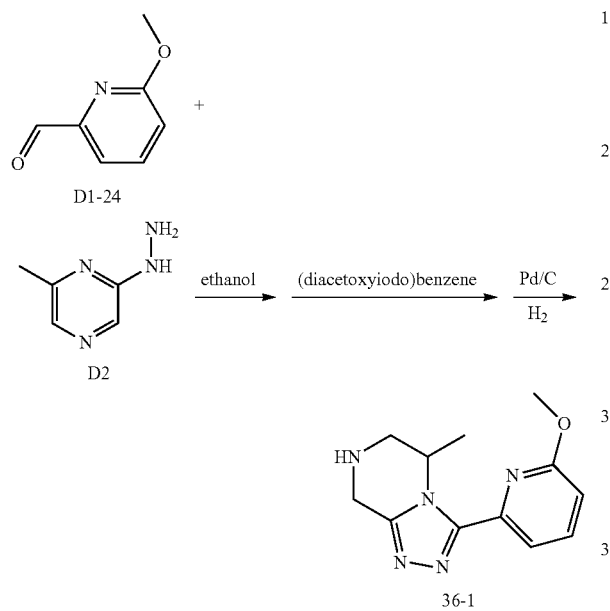

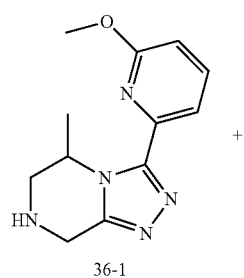

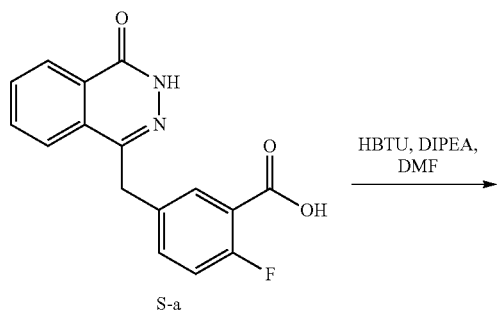

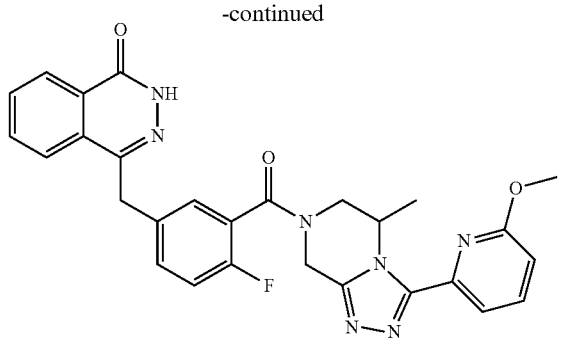

S36

Compound 36-1 was prepared by replacing the compound D-1 in synthesis method of compound 1-1 with compound D1-24. Analysis data of 36-1: ¹H NMR (300 MHz, Chloroform-d) δ 7.88 (d, J=7.4 Hz, 1H), 7.64 (s, 1H), 6.74 (d, J=8.3 Hz, 1H), 5.31 (s, 1H), 4.36 (d, J=16.6 Hz, 1H), 4.12 (d, J=16.6 Hz, 1H), 3.89 (d, J=1.5 Hz, 3H), 3.24 (dd, J=13.5, 4.1 Hz, 1H), 3.06 (d, J=13.4 Hz, 1H), 1.41 (d, J=6.6 Hz, 3H).

Compound S36 was prepared by replacing the compound 1-1 in synthesis method of compound S1 with compound 36-1. Analysis data of S36: ¹H NMR (300 MHz, Chloroform-d) δ 10.63 (d, J=16.9 Hz, 1H), 8.47-8.33 (m, 1H), 7.89 (d, J=7.2 Hz, 1H), 7.69 (dq, J=18.3, 7.4, 6.5 Hz, 4H), 7.31 (d, J=6.0 Hz, 2H), 7.05 (t, J=8.8 Hz, 1H), 6.77 (d, J=8.4 Hz, 1H), 5.73 (d, J=18.3 Hz, 0.5H), 5.61 (s, 1H), 5.42 (s, 0.5H), 4.91 (t, J=13.7 Hz, 1H), 4.62 (d, J=17.6 Hz, 1H), 4.24 (s, 2H), 3.85 (d, J=39.4 Hz, 3H), 3.67 (s, 0.5H), 3.41 (d, J=12.2 Hz, 1H), 1.52-1.25 (m, 3H).

37 Synthesis of Compound S37

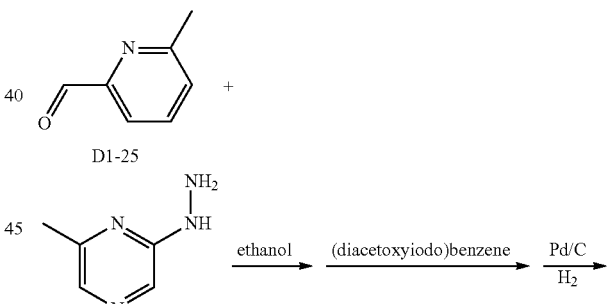

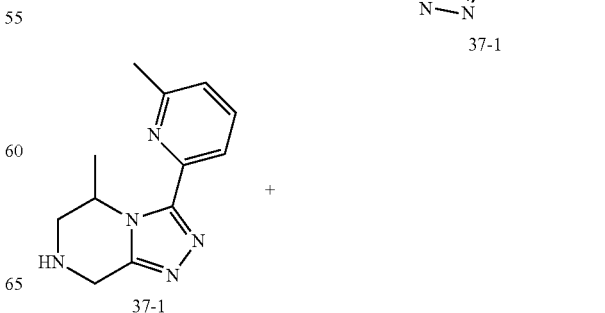

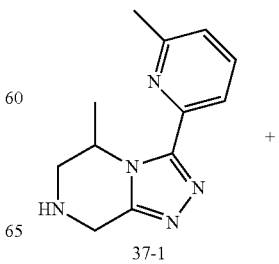

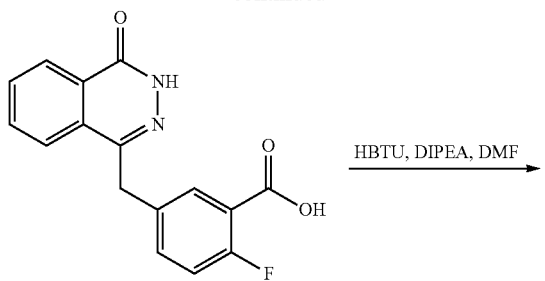
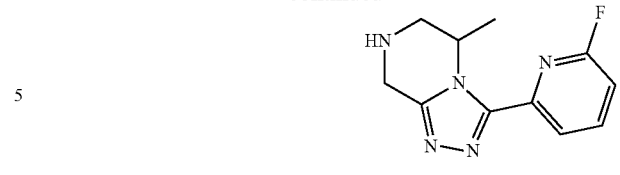
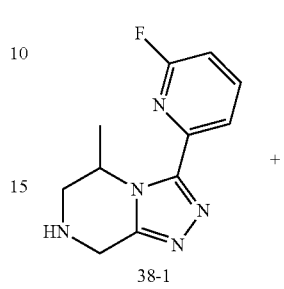
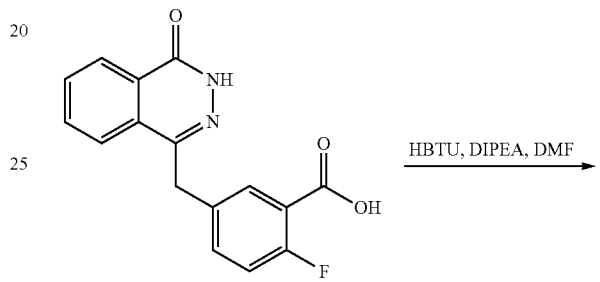

Compound 37-1 was prepared by replacing the compound D-1 in synthesis method of compound 1-1 with compound D1-25. Analysis data of 37-1: $^1$H NMR (300 MHz, Chloroform-d) 8.02 (d, J=7.9 Hz, 1H), 7.62 (t, J=7.8 Hz, 1H), 7.10 (d, J=7.7 Hz, 1H), 5.35 (t, J=6.0 Hz, 1H), 4.34 (d, J=16.6 Hz, 1H), 4.09 (d, J=16.6 Hz, 1H), 3.20 (dd, J=13.5, 4.1 Hz, 1H), 3.04 (d, J=13.5 Hz, 1H), 2.50 (s, 3H), 1.35 (d, J=6.5 Hz, 3H).

Compound S37 was prepared by replacing the compound 1-1 in synthesis method of compound S1 with compound 37-1. Analysis data of S37: $^1$H NMR (300 MHz, Chloroform-d) δ 10.45 (d, J=15.0 Hz, 1H), 8.48-8.32 (m, 1H), 8.05 (d, J=8.2 Hz, 1H), 7.85-7.52 (m, 4H), 7.31 (t, J=5.8 Hz, 2H), 7.09 (dt, J=25.4, 8.7 Hz, 2H), 5.69 (d, J=11.8 Hz, 1H), 4.91 (t, J=15.1 Hz, 1.5H), 4.61 (d, J=18.5 Hz, 1H), 4.24 (s, 2H), 3.66 (s, 0.5H), 3.46-3.29 (m, 1H), 2.54 (s, 3H), 1.42 (d, J=6.4 Hz, 3H).

38 Synthesis of Compound S38

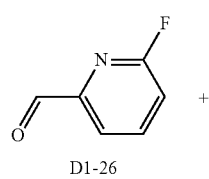
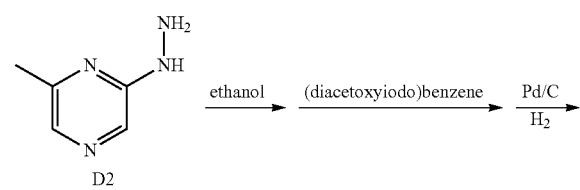

Compound 38-1 was prepared by replacing the compound D-1 in synthesis method of compound 1-1 with compound D1-26. Analysis data of 38-1: $^1$H NMR (300 MHz, Chloroform-d) δ 8.16 (dd, J=7.6, 2.2 Hz, 1H), 7.85 (q, J=8.0 Hz, 1H), 6.90 (dd, J=8.2, 2.8 Hz, 1H), 5.25 (ddd, J=8.9, 4.3, 2.2 Hz, 1H), 4.35 (dd, J=16.7, 1.0 Hz, 1H), 4.10 (d, J=16.7 Hz, 1H), 3.20 (dd, J=13.5, 4.1 Hz, 1H), 3.06 (dt, J=13.5, 1.4 Hz, 1H), 1.38 (d, J=6.5 Hz, 3H).

Compound S38 was prepared by replacing the compound 1-1 in synthesis method of compound S1 with compound 38-1. Analysis data of S38: $^1$H NMR (300 MHz, Chloroform-d) δ 10.54 (s, 1H), 8.40 (dd, J=7.3, 1.9 Hz, 1H), 8.18 (d, J=7.4 Hz, 1H), 7.88 (d, J=7.9 Hz, 1H), 7.80-7.57 (m, 3H), 7.31 (d, J=6.0 Hz, 2H), 7.04 (t, J=9.0 Hz, 1H), 6.95 (d, J=8.6 Hz, 1H), 5.75 (d, J=18.2 Hz, OH), 5.56 (s, 0.5H), 5.39 (s, 1H), 5.01-4.84 (m, 1H), 4.61 (d, J=18.9 Hz, 1H), 4.24 (s, 2H), 3.66 (s, 0.5H), 3.37 (d, J=13.7 Hz, 1H), 1.43 (d, J=6.5 Hz, 2H).

39 Synthesis of Compound S39

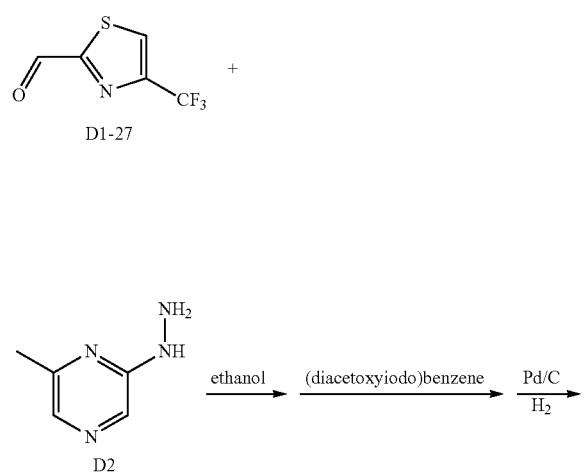

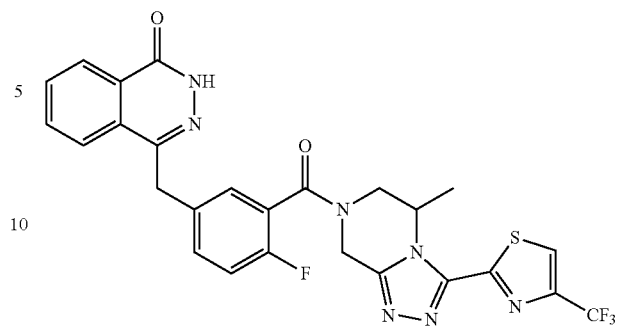

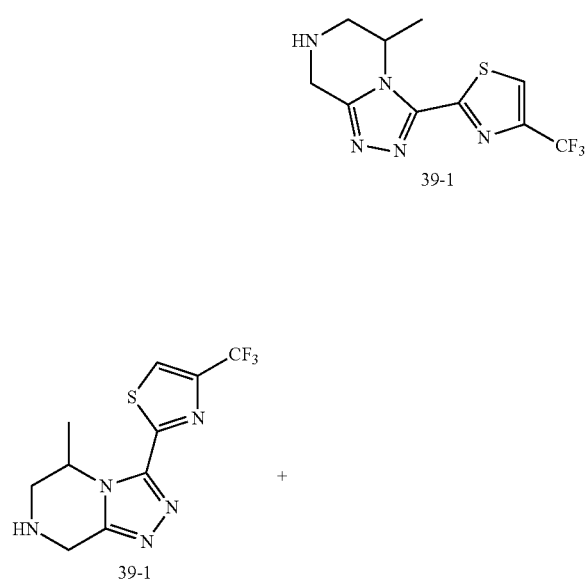

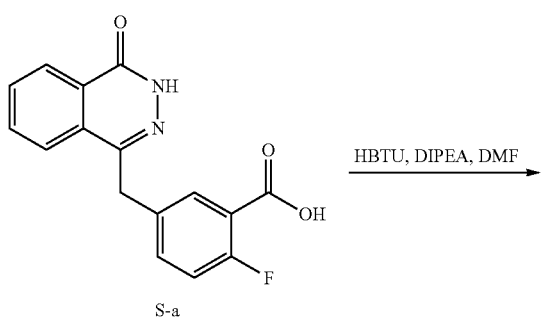

Compound 39-1 was prepared by replacing the compound D-1 in synthesis method of compound 1-1 with compound D1-27. Analysis data of 39-1: $^1$H NMR (300 MHz, Chloroform-d) δ 7.78 (q, J=0.9 Hz, 1H), 5.04 (ddd, J=6.1, 4.0, 1.8 Hz, 1H), 4.38 (dd, J=16.8, 0.9 Hz, 1H), 4.10 (d, J=16.8 Hz, 1H), 3.27-3.04 (m, 2H), 1.47 (d, J=6.4 Hz, 3H).

Compound S39 was prepared by replacing the compound 1-1 in synthesis method of compound S1 with compound 39-1. Analysis data of S39: $^1$H NMR (300 MHz, Chloroform-d) δ 10.60 (d, J=15.1 Hz, 1H), 8.50-8.32 (m, 1H), 7.73 (ddd, J=23.0, 18.8, 6.5 Hz, 4H), 7.32 (d, J=6.0 Hz, 2H), 7.05 (t, J=8.9 Hz, 1H), 5.84 (d, J=18.3 Hz, 0.5H), 5.34 (s, 1H), 5.14 (s, 0.5H), 5.05-4.87 (m, 1H), 4.59 (t, J=19.4 Hz, 1H), 4.25 (s, 2H), 3.68 (s, 0.5H), 3.44-3.31 (m, 0.5H), 1.48 (d, J=6.5 Hz, 3H).

II. Test Examples

1. High-Throughput Screening of PARP-1 Inhibitors at Molecular Level Using ELISA The HTb-PARP-1 positive clones were obtained using the full-length PARP-1 plasmid, through PCR amplification, enzyme digestion, ligation, and transformation into DH5a. The plasmids were extracted and determined by enzyme digestion, and then transformed into DH10Bac. Bacmid/PARP is determined by PCR and sequencing. TNI was transfected, the viruses were collected, and cells were lysed. PARP-1 protein was purified by affinity chromatography and determined by Western blotting. A plate was coated by substrate histone, NAD$^+$ and DNA, as well as expressed PARP-1 enzyme, was placed into 96-well plate reaction system. Various reaction conditions were optimized and ultimately determined. The product PAR was reacted with PAR monoclonal antibody, and then a secondary antibody was added. The OD value was read on a microplate reader, and PARP-1 enzyme activity inhibition was calculated accordingly, as shown in Table 1. wherein, AZD2281 (Orapani) was the first PARP inhibitor on the market developed by international pharmaceutical company AstraZeneca in 2014 and was a positive control compound in this trial.

TABLE 1
PARP-1 Enzymatic Inhibition of Compounds at Molecular Level
| Compound | Structure | Molecular Level (PARP-1) IC$_{50}$(nM) |
|---|---|---|
| AZD2281 | 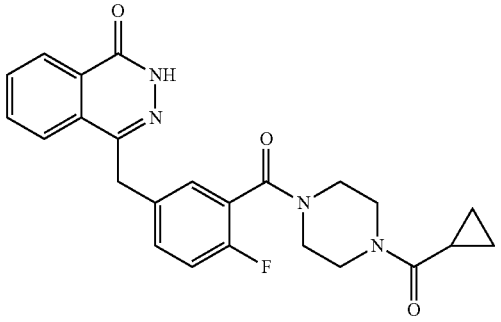 [SMILES: O=C(c1cc(Cc2n[nH]c(=O)c3ccccc23)ccc1F)N1CCN(C(=O)C2CC2)CC1] | <50 |
| S1 | 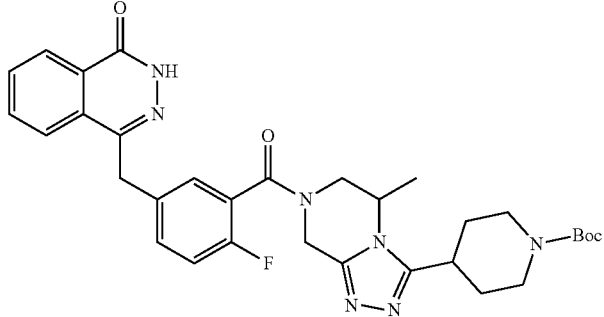 [SMILES: CC1CN(C(=O)c2cc(Cc3n[nH]c(=O)c4ccccc34)ccc2F)Cc2nnc(C3CCN(C(=O)OC(C)(C)C)CC3)n21] | <5 |
| S2 | 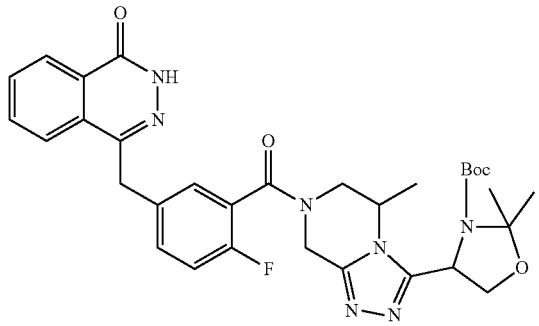 [SMILES: CC1CN(C(=O)c2cc(Cc3n[nH]c(=O)c4ccccc34)ccc2F)Cc2nnc(C3COC(C)(C)N3C(=O)OC(C)(C)C)n21] | <20 |
| S3 | 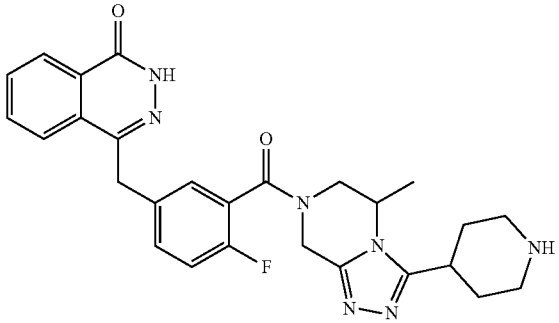 [SMILES: CC1CN(C(=O)c2cc(Cc3n[nH]c(=O)c4ccccc34)ccc2F)Cc2nnc(C3CCNCC3)n21] | <20 |

TABLE 1-continued

PARP-1 Enzymatic Inhibition of Compounds at Molecular Level

| Compound | Structure | Molecular Level (PARP-1) IC$_{50}$(nM) |
|---|---|---|
| S4 | 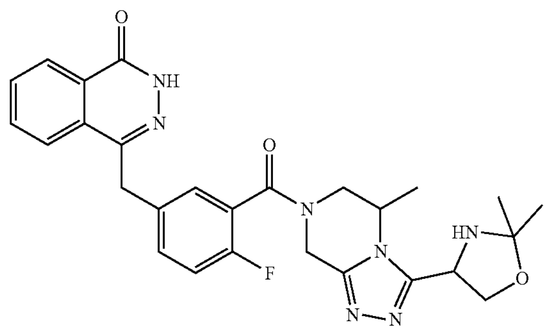 [SMILES: CC1CN(C(=O)c2cc(Cc3n[nH]c(=O)c4ccccc34)ccc2F)Cc2nnc(C3COC(C)(C)N3)n21] | <20 |
| S5 | 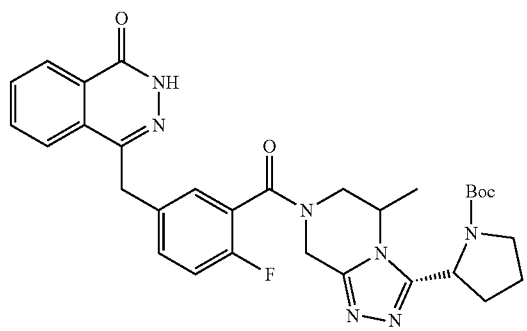 | <20 |
| S6 | 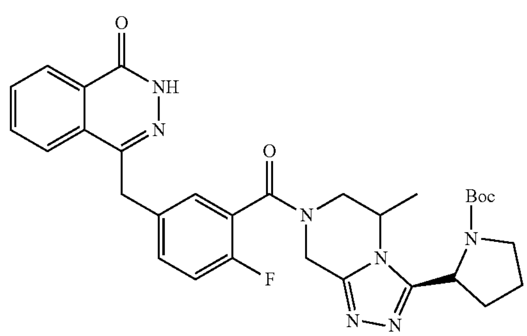 | <20 |
| S7 | 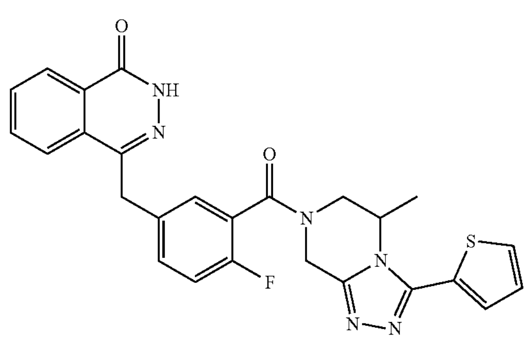 | <1 |

TABLE 1-continued

PARP-1 Enzymatic Inhibition of Compounds at Molecular Level

| Compound | Structure | Molecular Level (PARP-1) IC$_{50}$(nM) |
|---|---|---|
| S8 | 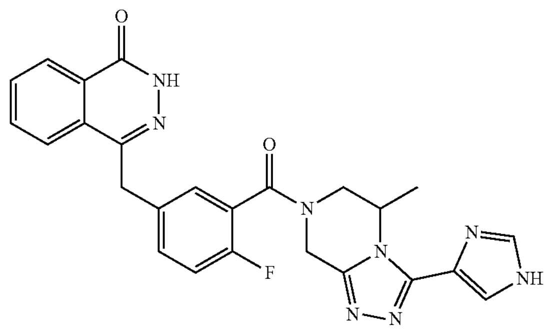 [SMILES: CC1CN(C(=O)c2cc(Cc3n[nH]c(=O)c4ccccc34)ccc2F)Cc2nnc(-c3c[nH]cn3)n21] | <20 |
| S9 | 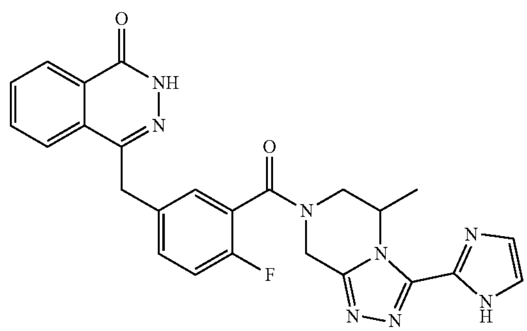 [SMILES: CC1CN(C(=O)c2cc(Cc3n[nH]c(=O)c4ccccc34)ccc2F)Cc2nnc(-c3ncc[nH]3)n21] | <5 |
| S10 | 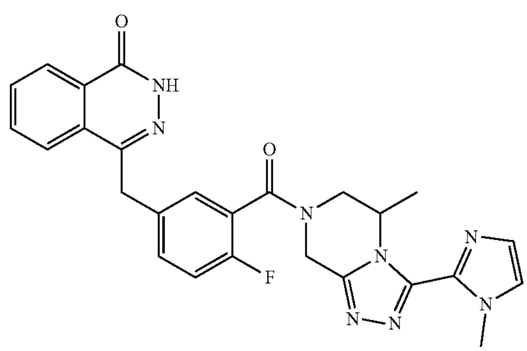 [SMILES: CC1CN(C(=O)c2cc(Cc3n[nH]c(=O)c4ccccc34)ccc2F)Cc2nnc(-c3nccn3C)n21] | <20 |
| S11 | 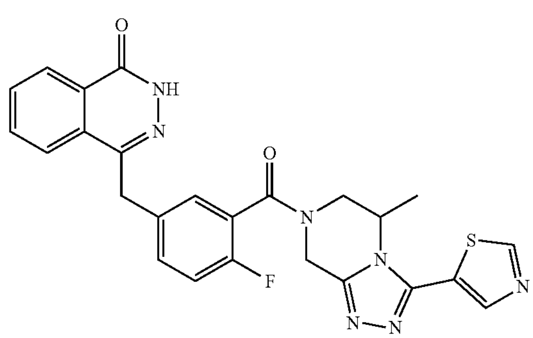 [SMILES: CC1CN(C(=O)c2cc(Cc3n[nH]c(=O)c4ccccc34)ccc2F)Cc2nnc(-c3cncs3)n21] | <20 |

TABLE 1-continued
PARP-1 Enzymatic Inhibition of Compounds at Molecular Level
| Compound | Structure | Molecular Level (PARP-1) IC$_{50}$(nM) |
|---|---|---|
| S12 | 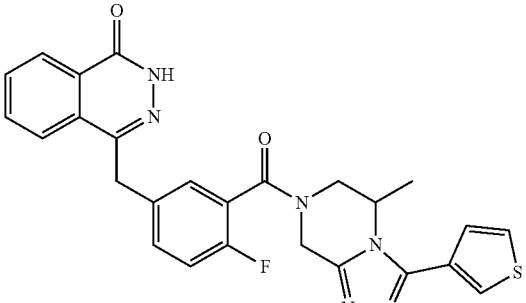 | <5 |
| S13 | 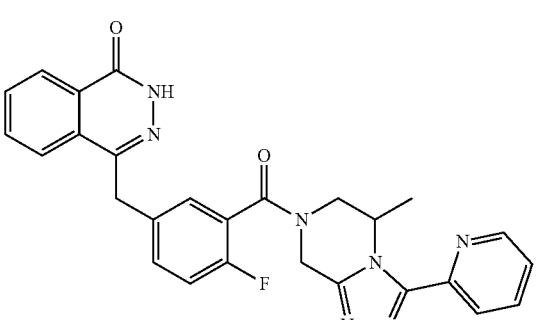 | <5 |
| S14 | 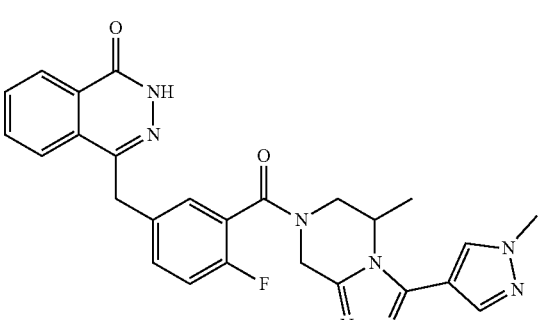 | <5 |
| S15 | 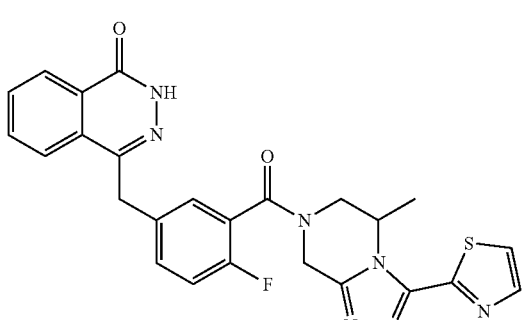 | <5 |

TABLE 1-continued

PARP-1 Enzymatic Inhibition of Compounds at Molecular Level

| Compound | Structure | Molecular Level (PARP-1) IC$_{50}$(nM) |
|---|---|---|
| S16 | 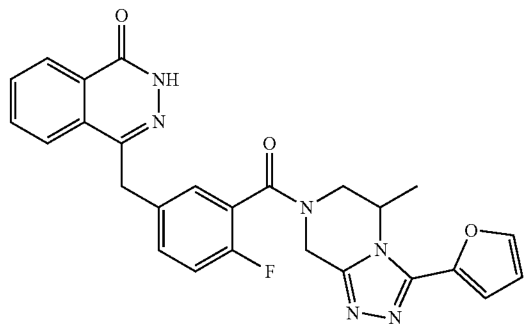 | <5 |
| S17 | 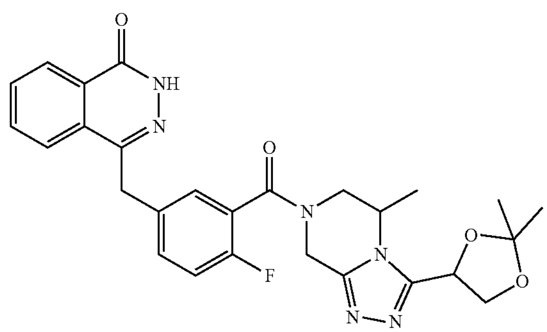 [SMILES: CC1CN(C(=O)c2cc(Cc3n[nH]c(=O)c4ccccc34)ccc2F)Cc2nnc(C3COC(C)(C)O3)n21] | <20 |
| S18 | 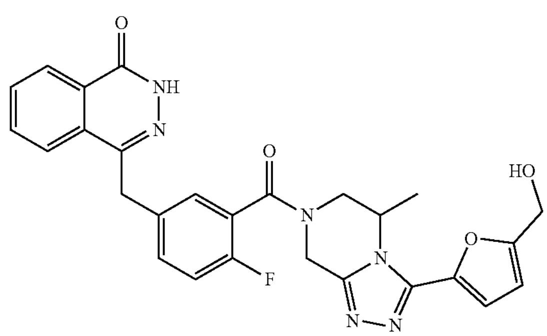 [SMILES: CC1CN(C(=O)c2cc(Cc3n[nH]c(=O)c4ccccc34)ccc2F)Cc2nnc(-c3ccc(CO)o3)n21] | <5 |
| S19 | 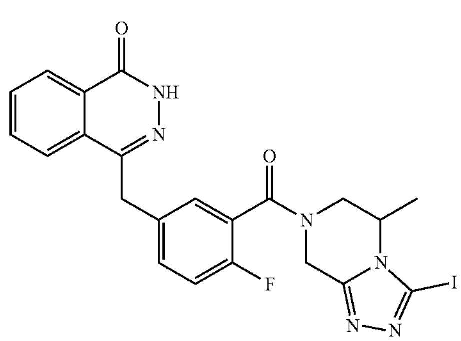 [SMILES: CC1CN(C(=O)c2cc(Cc3n[nH]c(=O)c4ccccc34)ccc2F)Cc2nnc(I)n21] | <5 |

TABLE 1-continued
PARP-1 Enzymatic Inhibition of Compounds at Molecular Level
| Compound | Structure | Molecular Level (PARP-1) IC$_{50}$(nM) |
|---|---|---|
| S20 | 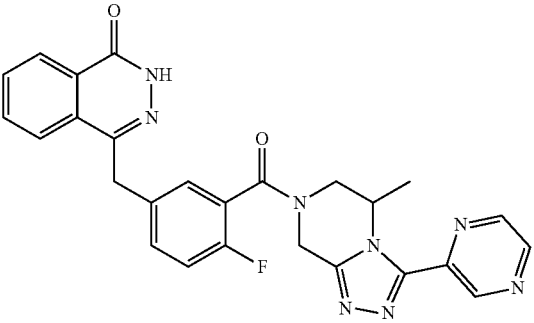 | <5 |
| S21 | 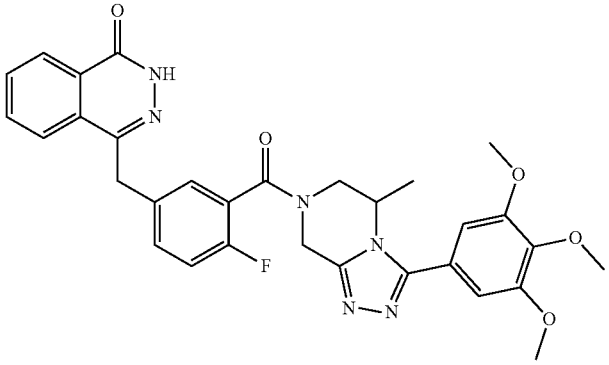 [SMILES: COc1cc(-c2nnc3n2C(C)CN(C(=O)c2cc(Cc4n[nH]c(=O)c5ccccc45)ccc2F)C3)cc(OC)c1OC] | <20 |
| S22 | 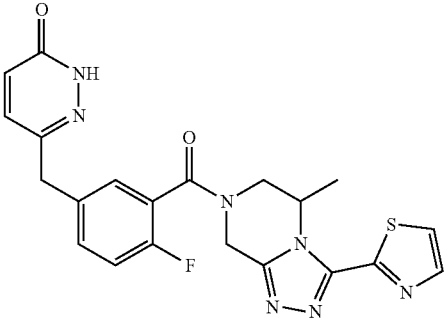 [SMILES: CC1CN(C(=O)c2cc(Cc3ccc(=O)[nH]n3)ccc2F)Cc2nnc(-c3nccs3)n21] | <100 |
| S23 | 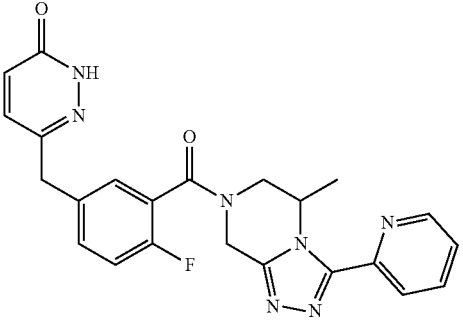 [SMILES: CC1CN(C(=O)c2cc(Cc3ccc(=O)[nH]n3)ccc2F)Cc2nnc(-c3ccccn3)n21] | <100 |

TABLE 1-continued

PARP-1 Enzymatic Inhibition of Compounds at Molecular Level

| Compound | Structure | Molecular Level (PARP-1) IC$_{50}$(nM) |
|---|---|---|
| S24 | 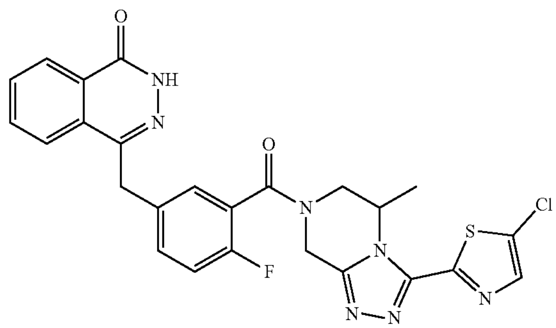 [SMILES: CC1CN(C(=O)c2cc(Cc3n[nH]c(=O)c4ccccc34)ccc2F)Cc2nnc(-c3ncc(Cl)s3)n21] | <20 |
| S25 | 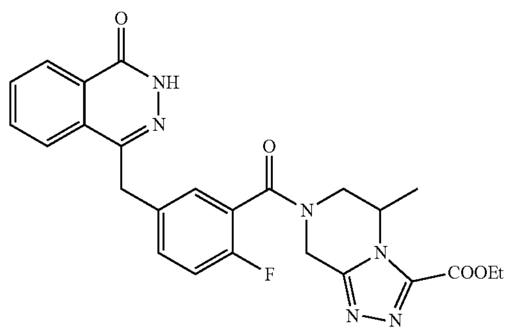 [SMILES: CCOC(=O)c1nnc2n1C(C)CN(C(=O)c1cc(Cc3n[nH]c(=O)c4ccccc34)ccc1F)C2] | <5 |
| S26 | 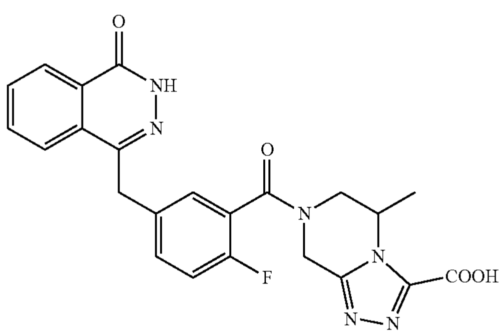 [SMILES: CC1CN(C(=O)c2cc(Cc3n[nH]c(=O)c4ccccc34)ccc2F)Cc2nnc(C(=O)O)n21] | <5 |
| S27 | 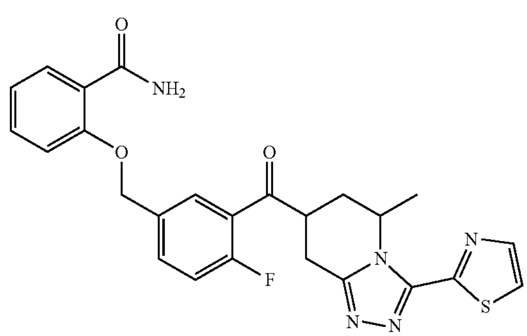 [SMILES: CC1CC(C(=O)c2cc(COc3ccccc3C(N)=O)ccc2F)Cc2nnc(-c3nccs3)n21] | <100 |

TABLE 1-continued

PARP-1 Enzymatic Inhibition of Compounds at Molecular Level

| Compound | Structure | Molecular Level (PARP-1) IC$_{50}$(nM) |
|---|---|---|
| S28 | 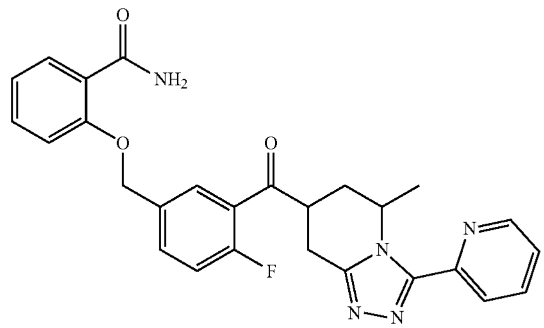 | <100 |
| S29 | 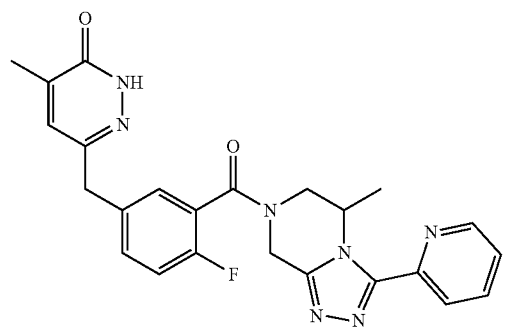 [SMILES: Cc1cc(Cc2ccc(F)c(C(=O)N3Cc4nnc(-c5ccccn5)n4C(C)C3)c2)n[nH]c1=O] | <100 |
| S30 | 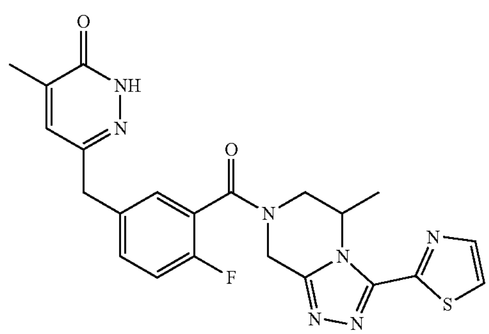 [SMILES: Cc1cc(Cc2ccc(F)c(C(=O)N3Cc4nnc(-c5nccs5)n4C(C)C3)c2)n[nH]c1=O] | <100 |
| S31 | 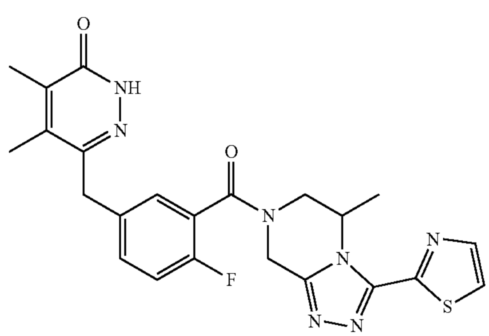 [SMILES: Cc1c(Cc2ccc(F)c(C(=O)N3Cc4nnc(-c5nccs5)n4C(C)C3)c2)n[nH]c(=O)c1C] | <100 |

TABLE 1-continued

PARP-1 Enzymatic Inhibition of Compounds at Molecular Level

| Compound | Structure | Molecular Level (PARP-1) IC$_{50}$(nM) |
|---|---|---|
| S32 | 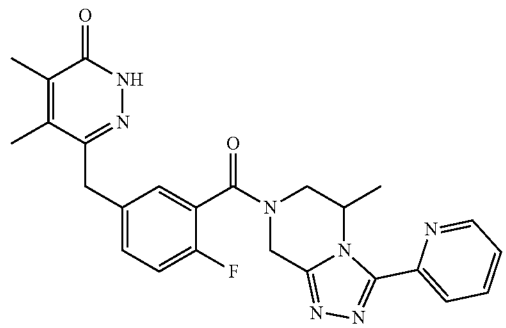 | <100 |
| S33 | 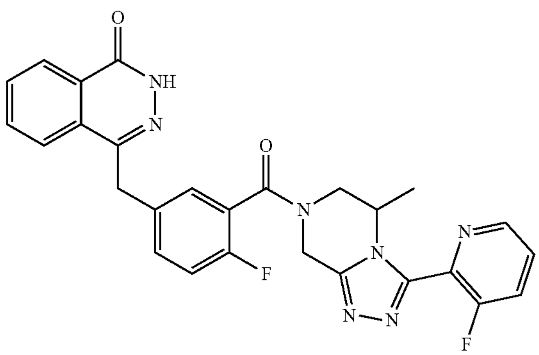 [SMILES: CC1CN(C(=O)c2cc(Cc3n[nH]c(=O)c4ccccc34)ccc2F)Cc2nnc(-c3ncccc3F)n21] | <5 |
| S34 | 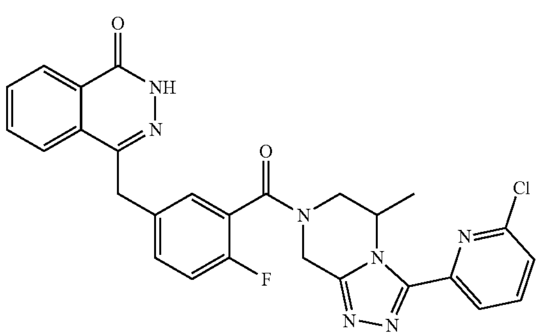 | <5 |
| S35 | 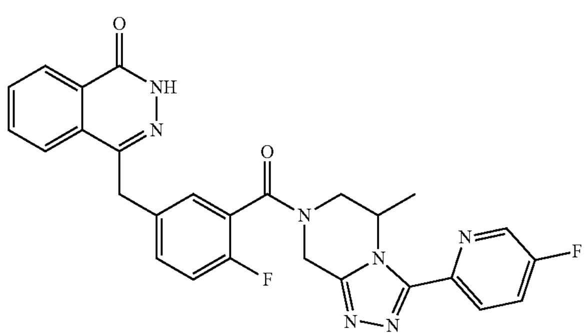 [SMILES: CC1CN(C(=O)c2cc(Cc3n[nH]c(=O)c4ccccc34)ccc2F)Cc2nnc(-c3ccc(F)cn3)n21] | <5 |

TABLE 1-continued

PARP-1 Enzymatic Inhibition of Compounds at Molecular Level

| Compound | Structure | Molecular Level (PARP-1) IC$_{50}$(nM) |
|---|---|---|
| S36 | 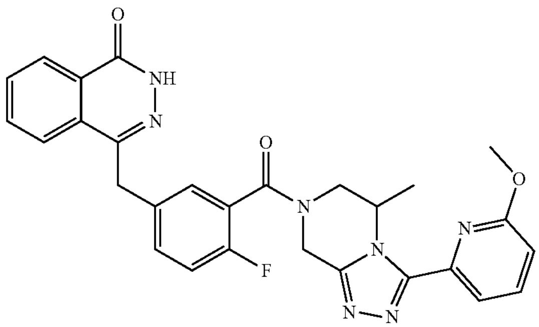 [SMILES: COc1cccc(-c2nnc3n2C(C)CN(C(=O)c2cc(Cc4n[nH]c(=O)c5ccccc45)ccc2F)C3)n1] | <1 |
| S37 | 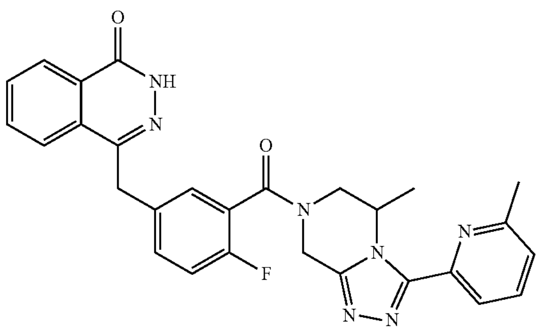 [SMILES: Cc1cccc(-c2nnc3n2C(C)CN(C(=O)c2cc(Cc4n[nH]c(=O)c5ccccc45)ccc2F)C3)n1] | <5 |
| S38 | 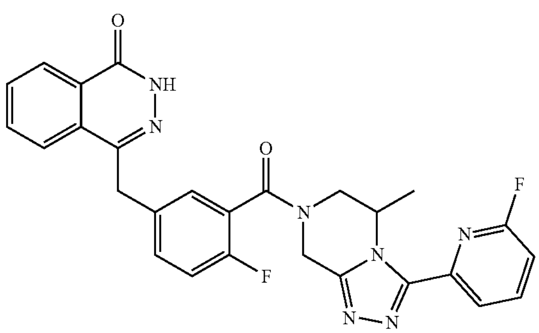 | <5 |
| S39 | 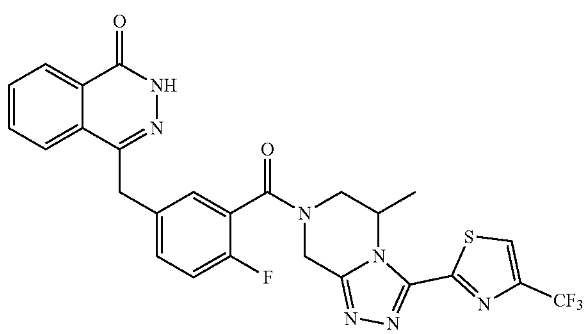 [SMILES: CC1CN(C(=O)c2cc(Cc3n[nH]c(=O)c4ccccc34)ccc2F)Cc2nnc(-c3nc(C(F)(F)F)cs3)n21] | <5 |

It was shown in Table 1 that most of the compounds exhibited high affinity for PARP-1 enzyme at molecular level and exhibited significant inhibitory effect against PARP. The inhibition concentrations for most compounds were in nanomolar range (<100 nM). And, most of the compounds exhibited higher PARP inhibitory activity than the positive compound. The best compound even reached 1 nM or less, which was 50 times more potent than the positive compound AZD-2281. Therefore, the compounds of the present invention can be used as novel potent PARP-1 inhibitors for the prevention and treatment of diseases associated with PARP (poly(ADP-ribose) polymerase), such as ischemic diseases, neurodegenerative diseases and cancers.

2. Chiral Separation of Compounds

Figure 2:
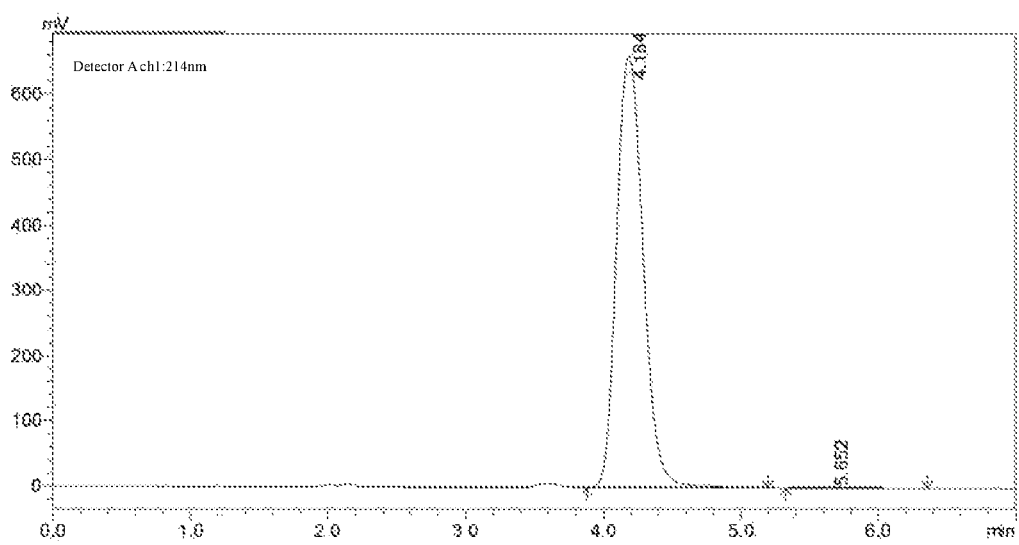
FIG. 2 is a HPLC spectrum of compound S13-(−)
Figure 3:
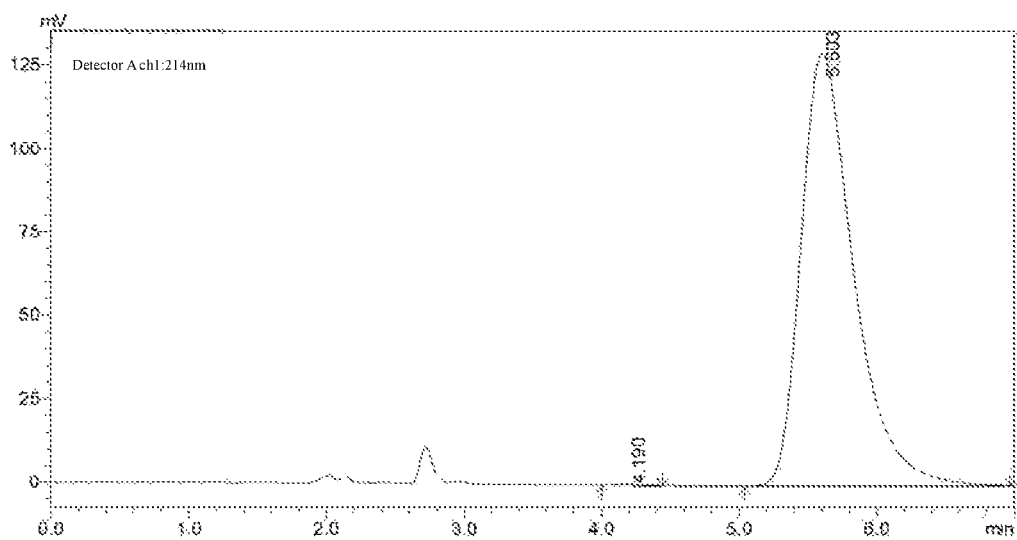
FIG. 3 is a HPLC spectrum of compound S13-(+).

Since most of the compounds have one or two chiral centers, the optical isomers were separated by chiral preparative HPLC. For example, both enantiomers of compound S13 showed relatively high inhibitory activity to PARP-1 enzyme, wherein the activity of (+)-S13 was twice of that of (−)-S13, indicating that the (+)-isomer interacts with PARP enzyme more effectively. Specific results were listed as follows:

1) Chiral Resolution Conditions:
Chiral column: CHIRALPAK IA
Chiral column size: 0.46 cm I.D.×15 cm L
Mobile phase: Hexane/IPA=40/60 (v/v); Flow rate: 1 ml/min Detection wavelength: UV 254 nm 2) Chiral HPLC Spectrum: Referring to Figure. 1-3.

FIG. 1 is a HPLC spectrum of compound S13;

FIG. 2 is a HPLC spectrum of compound S13-(−);

FIG. 3 is a HPLC spectrum of compound S13-(+).

3) PARP-1 Inhibitory Activity of Enantiomers, See Table 2

TABLE 2

| | PARP-1 Inhibitory Activity of S13 and Its Corresponding Enantiomers | | |
|---|---|---|---|
| Compound | Structure | Optical rotation value$[\alpha]^{20}_D$ | Molecular level (PARP-1) IC$_{50}$(nM) |
| AZD2281 | (structure) | none | 43 |
| S13 | (structure) | none | 1.25 |
| S13-(+) | (structure) | 98.8 (c 0.1, MeOH) | 0.86 |

TABLE 2-continued

PARP-1 Inhibitory Activity of S13 and Its Corresponding Enantiomers

| Compound | Structure | Optical rotation value$[\alpha]^{20}_D$ | Molecular level (PARP-1) $IC_{50}$(nM) |
|---|---|---|---|
| S13-(−) | 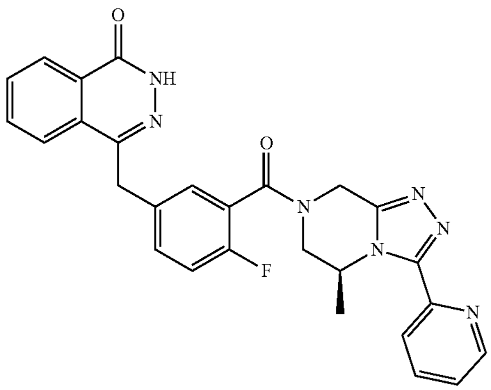 [SMILES: C[C@H]1CN(C(=O)c2cc(Cc3n[nH]c(=O)c4ccccc34)ccc2F)Cc2nnc(-c3ccccn3)n21] | −91.6 (c 0.1, MeOH) | 1.7 |

3. Cellular Assay of Representative Compounds

The inhibitory effect of the compound on the proliferation of MDA-MB-436 and Capan-1 cells was evaluated by the CCK-8 and SRB method using AZD2281 as a positive control compound. The results are shown in Table 3.

TABLE 3

Inhibitory of Representative Compounds on the Proliferation of MDA-MB-436 and Capan-1 Cells

| | Cellular $IC_{50}$ (nM) | |
|---|---|---|
| compound | MDA-MB-436 (BRCA1gene defect) | Capan-1 (BRCA2gene defect) |
| AZD2281 | ~200 | ~500 |
| S3 | <200 | <200 |
| S7 | <5 | <5 |
| S8 | <20 | <20 |
| S9 | <5 | <20 |
| S10 | <20 | <20 |
| S11 | <20 | <20 |
| S12 | <20 | <20 |
| S13 | <5 | <5 |
| S14 | <20 | <20 |
| S15 | <5 | <5 |
| S16 | <5 | <5 |
| S18 | <5 | <5 |
| S20 | <20 | <20 |
| S33 | <20 | <20 |

From the results above, it can be seen that the new compounds not only have high activity on PARP-1 at the enzyme level, but also possess strong inhibitory effect on the proliferation of BRCA-deficient MDA-MB-436 and Capan-1 cells. The results indicated that most of the compounds have higher (10 times or more) activity than positive control compound AZD2281.

4. Comparison of Inhibitory Effects of Representative Compound S13 and AZD2281 on Proliferation of Different Tumor Cells In order to further clarify the potential advantage of the new compounds over AZD2281, the inhibitory effects of the representative compound S13 and AZD2281 on the proliferation of different tumor cells were tested. The results are shown in Table 4. This result indicated that the inhibition of compound S13 on proliferation of tumor cells derived from four different tissues is stronger than that of AZD2281, up to 628-fold for the best.

TABLE 4

Inhibition of Representative Compound S13 and AZD2281 on Proliferation of Different Tumor Cells

| | | $IC_{50}$ (nM) | | Ratio |
|---|---|---|---|---|
| Cell stain | Tumor type | S13 | AZD2281 | $IC_{50\ AZD}/IC_{50\ S13}$ |
| Capan-1 | pancreatic cancer | 1.04 | 653 | 628 |
| HCC-1937 | breast cancer | 21.88 | 7389 | 338 |
| HCT-15 | colon cancer | 143 | >10 uM | 70 |
| SW-620 | colon cancer | 45 | 5839 | 130 |
| UWB1.289 | ovarian cancer | 3 | 177 | 59 |

5. Anti-Proliferative Effect of Compounds Against AZD2281 Resistant Cells

Compared with AZD2281, the substituted triazolopiperazine compounds in present invention have higher activity. In order to study the activity of these compounds against AZD2281 resistant cells, the inventors investigated the anti-proliferative ability of compound S13 against AZD2281 resistant cells. The results are shown in Table 5. Comparing the $IC_{50}$ of AZD2281 in the Capan-1 parental cell line and drug resistant cell line, AZD2281 shows drug resistance for about 14-fold, while the $IC_{50}$ of compound S13 remained below 0.256 nM. It can be seen that the compound of the present invention is highly active against drug-resistant cells and has an excellent development prospect.

TABLE 5

Inhibition Effect of Compound S13 and AZD2281 on the Proliferation of Capan-1 Parental Cell and Drug Resistant Cell

| Cell strain | $IC_{50}$ & Resistance index | AZD2281 | S13 |
|---|---|---|---|
| Capan-1 parental cell | $IC_{50}$ (nM) | 2899 ± 17 | <0.256 |
| Capan-1/AZD2281 drug resistant cell | $IC_{50}$ (nM) | 41074 ± 1593 | <0.256 |
| Drug Resistance | Resistance index | >14 | none |

6. Inhibitory Activity of Compounds on the hERG Potassium Channel

In order to evaluate whether the new compounds have good safety, especially for the inhibitory activity of the hERG potassium channel-related cardiotoxicity, the inhibitory activity of these compounds on hERG were further tested. The results are shown in Table 6:

TABLE 6

Inhibition of Compounds on the hERG Potassium Channel

| compound | IC$_{50}$ (μM) |
|---|---|
| S3 | >10 |
| S13 | >10 |
| S13-(+) | >10 |
| S13-(−) | >10 |
| S7 | >10 |
| S8 | >10 |
| S20 | >10 |
| S33 | >10 |

It is clear that these compounds, either as racemates or as stereoisomers, have no inhibition on the hERG potassium channel, and thus they have a low risk of cardiotoxicity.

In summary, these aryl- or heteroaryl-substituted triazolopiperazine compounds, such as compound S13, have extremely high inhibitory activity against PARP-1 enzyme, and their cell activities are also significantly higher than that of the positive control compound AZD2281. At the same time, the presence of the methyl substituent on the ring significantly increases the selectivity of the compound for the telomerases TNKS1 and TNKS2, resulting in low risk of cardiotoxicity. Therefore, these compounds can be used as novel and highly selective poly (ADP-ribose) polymerase-1 (PARP-1) inhibitors for prevention and/or treatment of diseases associated with PARP.

The invention claimed is:

1. A substituted triazolopiperazine compound represented by formula (I), or a tautomer, enantiomer, diastereomer, racemate, pharmaceutically acceptable salt, ester or hydrate thereof:

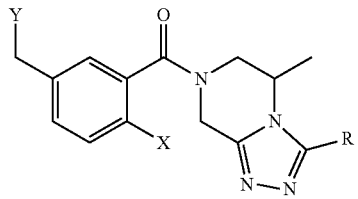
(I)

wherein,
Y is

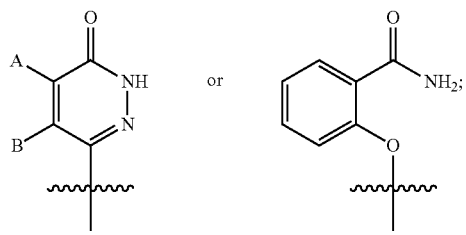

A and B together with the carbon atoms to which they are attached form a substituted or unsubstituted C4-C6 aliphatic ring or a substituted or unsubstituted C6-C8 aromatic ring, wherein the substituent in the substituted rings is selected from one or more of the group consisting of halogen, cyano, nitro, hydroxyl, and amino;

X is hydrogen, halogen, hydroxyl, or cyano;

R is halogen, COOR$^1$, substituted or unsubstituted heterocyclic ring, substituted or unsubstituted heteroaromatic ring, substituted or unsubstituted aromatic ring, wherein the substituent in the substituted heterocyclic ring, heteroaromatic ring, or aromatic ring is selected from one or more of the group consisting of substituted or unsubstituted C1-C4 alkyl, halogen, cyano, nitro, hydroxyl, amino, C1-C4 alkoxy, C2-C4 alkylcarbonyl, A and B together with the carbon atoms to which they are attached form a substituted or unsubstituted C4-C8 aliphatic ring, a substituted or unsubstituted C6-C10 aromatic ring, a substituted or unsubstituted 4-8 membered heterocyclic ring containing 1-3 heteroatoms selected from N, O and S, or a substituted or unsubstituted 5-8 membered heteroaromatic ring containing 1-3 heteroatoms selected from N, O, and S; wherein the substituent in the substituted rings is selected from one or more of the group consisting of halogen, cyano, nitro, hydroxyl, and amino;

X is hydrogen, halogen, hydroxyl, or cyano;

R is halogen, COOR$^1$, substituted or unsubstituted heterocyclic ring, substituted or unsubstituted heteroaromatic ring, substituted or unsubstituted aromatic ring, wherein the substituent in the substituted heterocyclic ring, heteroaromatic ring or aromatic ring is selected from one or more of the group consisting of substituted or unsubstituted C1-C8 alkyl, halogen, cyano, nitro, hydroxyl, amino, C1-C6 alkoxy, C2-C6 alkylcarbonyl, C2-C6 alkoxycarbonyl, C2-C6 alkenyl, C2-C6 alkynyl, and C6-C10 aryl, wherein the substituent in the substituted C1-C8 alkyl is selected from one or more of the group consisting of halogen, cyano, nitro, hydroxyl, amino;

R$^1$ is selected from the group consisting of hydrogen, C1-C8 alkyl, substituted or unsubstituted aryl, or substituted or unsubstituted heterocyclyl, wherein the substituent in the substituted aryl or heterocyclyl is selected from one or more of the group consisting of C1-C8 alkyl, halogen, cyano, nitro, hydroxyl, amino, C1-C6 alkoxy, C2-C6 alkylcarbonyl, C2-C6 alkoxycarbonyl, C2-C6 alkenyl, C2-C6 alkynyl, and C6-C10 aryl.

2. The substituted triazolopiperazine compound represented by formula (I) according to claim 1, or a tautomer, enantiomer, diastereomer, racemate, pharmaceutically acceptable salt, ester or hydrate thereof,
wherein,
Y is

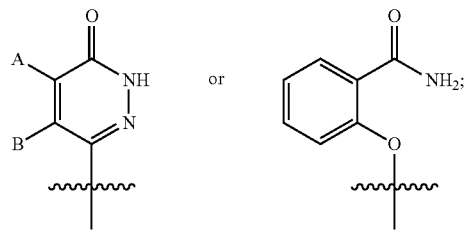

C2-C4 alkoxycarbonyl, C2-C4 alkenyl, C2-C4 alkynyl and phenyl, wherein the substituent in the substituted C1-C4 alkyl is selected from one or more of the group consisting of halogen, cyano, nitro, hydroxyl, amino;

R¹ is selected from the group consisting of hydrogen, C1-C4 alkyl, substituted or unsubstituted aryl, or substituted or unsubstituted heterocyclyl, wherein the substituent in the substituted aryl or heterocyclyl is selected from one or more of the group consisting of C1-C4 alkyl, halogen, cyano, nitro, hydroxy, amino, C1-C4 alkoxy, C2-C4 alkylcarbonyl, C2-C4 alkoxycarbonyl, C2-C4 alkenyl, C2-C4 alkynyl and phenyl.

3. The substituted triazolopiperazine compound represented by formula (I) according to claim 1, or a tautomer, enantiomer, diastereomer, racemate, pharmaceutically acceptable salt, ester or hydrate thereof,
wherein,
Y is

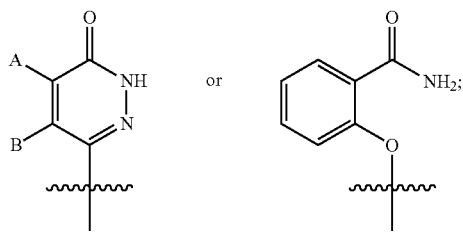

A and B together with the carbon atoms to which they are attached form a benzene ring;
X is hydrogen or halogen;
R is halogen, COOR¹, substituted or unsubstituted phenyl, substituted or unsubstituted 5- and 6-membered heterocyclic ring, substituted or unsubstituted 5- and 6-membered heteroaromatic ring, wherein the substituent in the substituted phenyl, heterocyclic ring, or heteroaromatic ring is selected from one or more of the group consisting of methyl, halogen, trifluoromethyl, methoxy, hydroxymethyl;
R¹ is selected from hydrogen, methyl and ethyl.

4. The substituted triazolopiperazine compound represented by formula (I) according to claim 1, or a tautomer, enantiomer, diastereomer, racemate, pharmaceutically acceptable salt, ester or hydrate thereof,
wherein the tautomer has the structure of the following formula II, wherein X, A, B and R are as defined in formula (I) of claim 1:

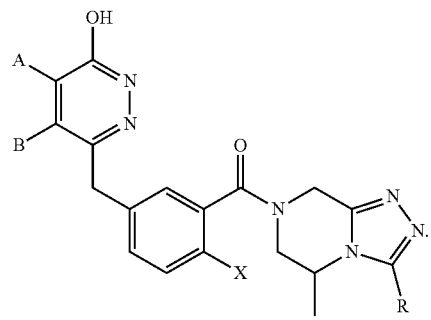

5. The substituted triazolopiperazine compound represented by formula (I) according to claim 1, or a tautomer, enantiomer, diastereomer, racemate, pharmaceutically acceptable salt, ester or hydrate thereof,
wherein, the substituted triazolopiperazine compound represented by formula (I) is selected from the group consisting of the following:

| compound | Structure |
|---|---|
| S1 | 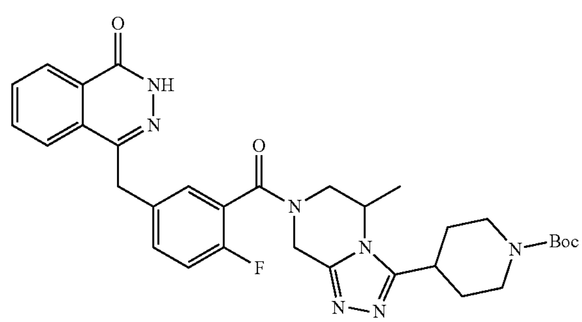 [SMILES: CC1CN(C(=O)c2cc(Cc3n[nH]c(=O)c4ccccc34)ccc2F)Cc2nnc(C3CCN(C(=O)OC(C)(C)C)CC3)n21] |
| S2 | 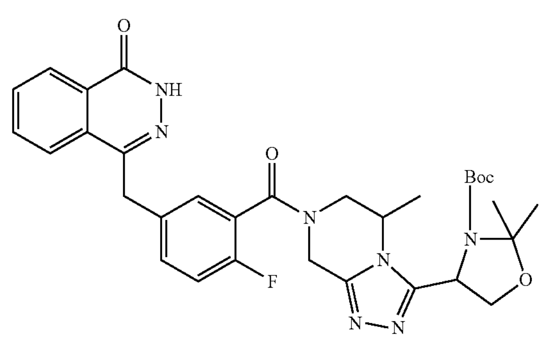 [SMILES: CC1CN(C(=O)c2cc(Cc3n[nH]c(=O)c4ccccc34)ccc2F)Cc2nnc(C3COC(C)(C)N3C(=O)OC(C)(C)C)n21] |

-continued

| compound | Structure |
|---|---|
| S3 | 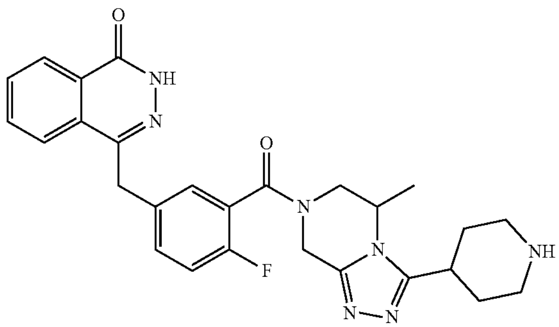 [SMILES: CC1CN(C(=O)c2cc(Cc3n[nH]c(=O)c4ccccc34)ccc2F)Cc2nnc(C3CCNCC3)n21] |
| S4 | 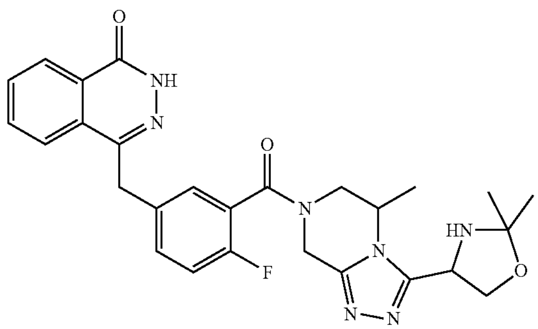 [SMILES: CC1CN(C(=O)c2cc(Cc3n[nH]c(=O)c4ccccc34)ccc2F)Cc2nnc(C3COC(C)(C)N3)n21] |
| S5 | 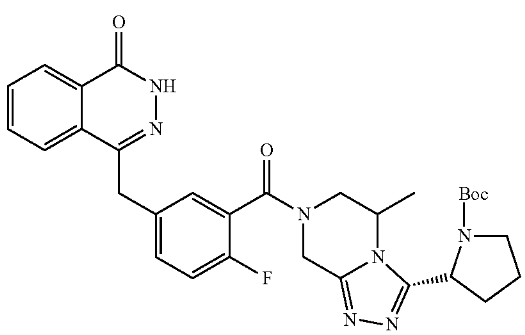 |
| S6 | 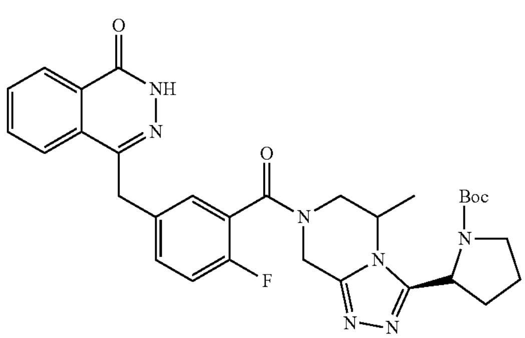 |

-continued
| compound | Structure |
|---|---|
| S7 | 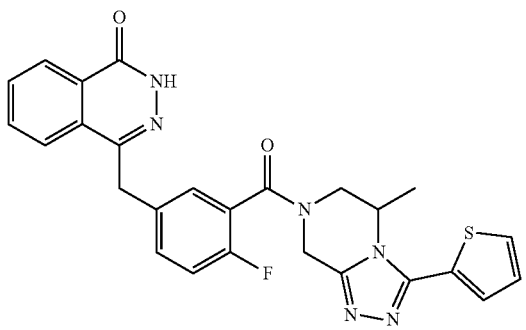 |
| S8 | 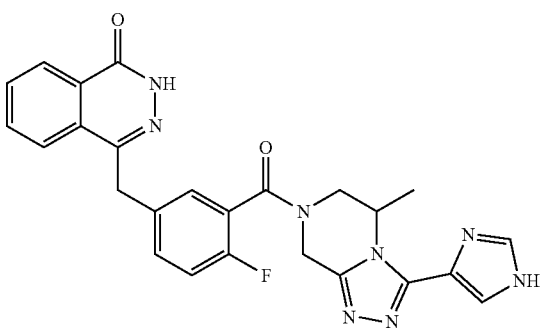 [SMILES: CC1CN(C(=O)c2cc(Cc3n[nH]c(=O)c4ccccc34)ccc2F)Cc2nnc(-c3c[nH]cn3)n21] |
| S9 | 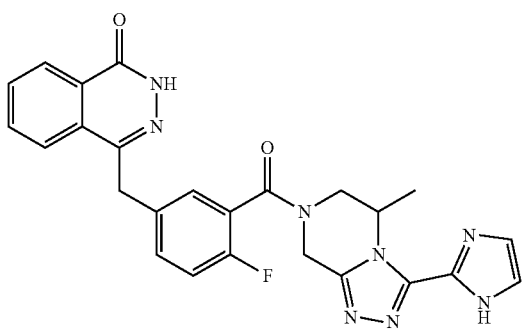 [SMILES: CC1CN(C(=O)c2cc(Cc3n[nH]c(=O)c4ccccc34)ccc2F)Cc2nnc(-c3ncc[nH]3)n21] |
| S10 | 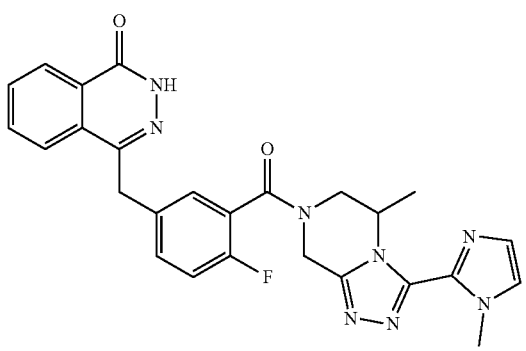 [SMILES: CC1CN(C(=O)c2cc(Cc3n[nH]c(=O)c4ccccc34)ccc2F)Cc2nnc(-c3nccn3C)n21] |

| compound | Structure |
|---|---|
| S11 | 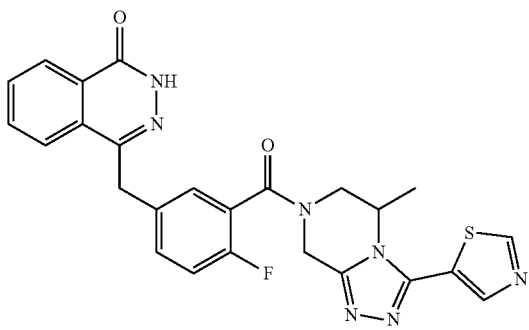 [SMILES: CC1CN(C(=O)c2cc(Cc3n[nH]c(=O)c4ccccc34)ccc2F)Cc2nnc(-c3cncs3)n21] |
| S12 | 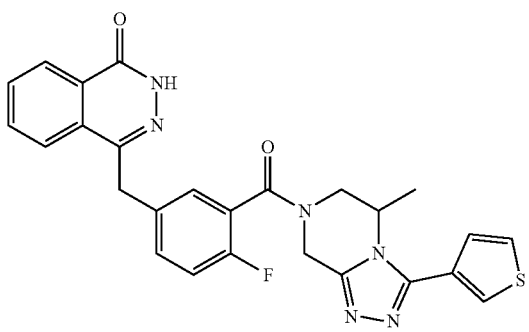 [SMILES: CC1CN(C(=O)c2cc(Cc3n[nH]c(=O)c4ccccc34)ccc2F)Cc2nnc(-c3ccsc3)n21] |
| S13 | 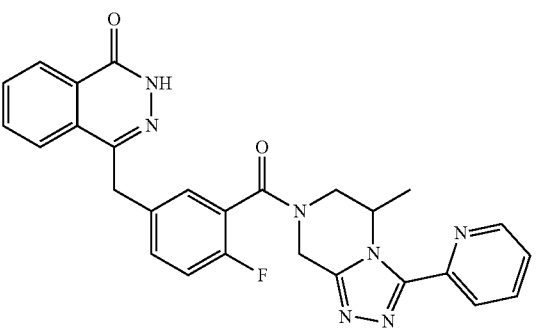 [SMILES: CC1CN(C(=O)c2cc(Cc3n[nH]c(=O)c4ccccc34)ccc2F)Cc2nnc(-c3ccccn3)n21] |
| S14 | 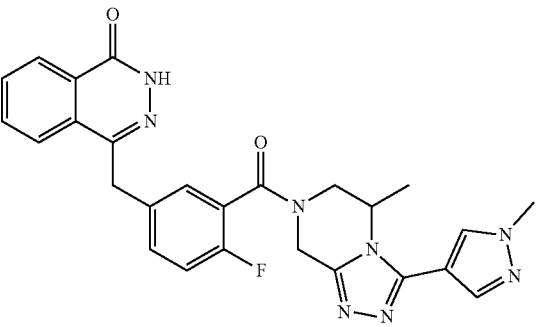 [SMILES: CC1CN(C(=O)c2cc(Cc3n[nH]c(=O)c4ccccc34)ccc2F)Cc2nnc(-c3cnn(C)c3)n21] |

| compound | Structure |
|---|---|
| S15 | 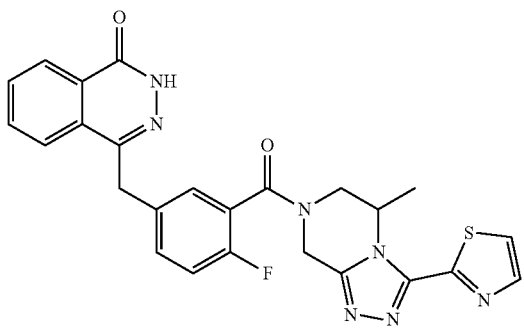 [SMILES: CC1CN(C(=O)c2cc(Cc3n[nH]c(=O)c4ccccc34)ccc2F)Cc2nnc(-c3nccs3)n21] |
| S16 | 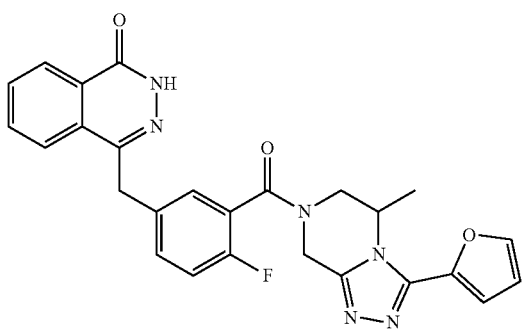 |
| S17 | 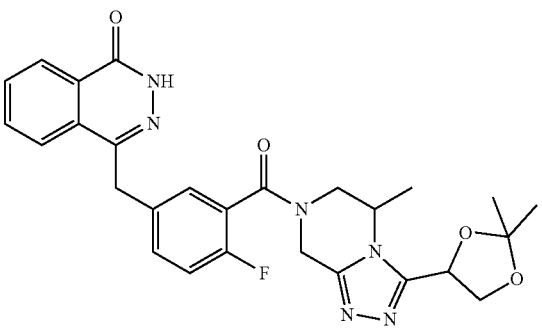 [SMILES: CC1CN(C(=O)c2cc(Cc3n[nH]c(=O)c4ccccc34)ccc2F)Cc2nnc(C3COC(C)(C)O3)n21] |
| S18 | 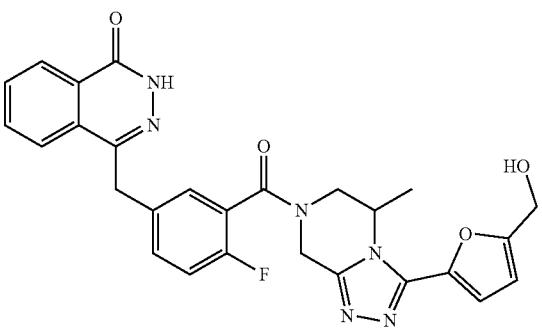 [SMILES: CC1CN(C(=O)c2cc(Cc3n[nH]c(=O)c4ccccc34)ccc2F)Cc2nnc(-c3ccc(CO)o3)n21] |

| compound | Structure |
|---|---|
| S19 | 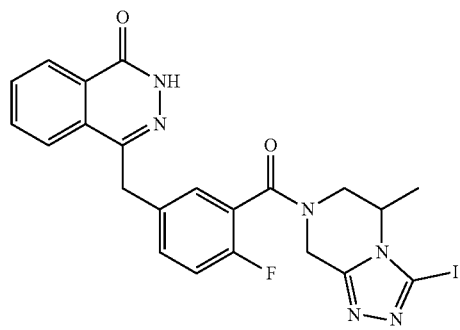 [SMILES: CC1CN(C(=O)c2cc(Cc3n[nH]c(=O)c4ccccc34)ccc2F)Cc2nnc(I)n21] |
| S20 | 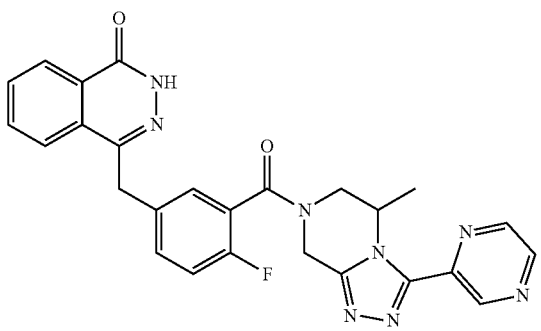 [SMILES: CC1CN(C(=O)c2cc(Cc3n[nH]c(=O)c4ccccc34)ccc2F)Cc2nnc(-c3cnccn3)n21] |
| S21 | 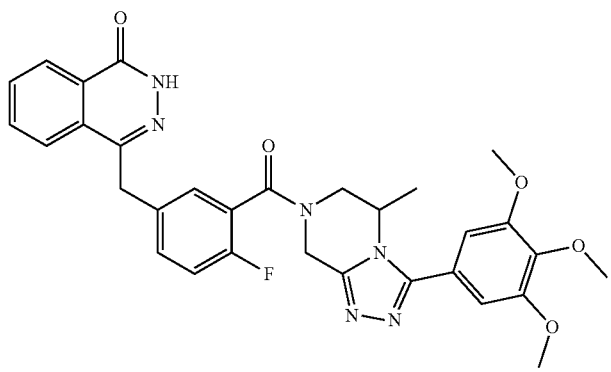 [SMILES: COc1cc(-c2nnc3n2C(C)CN(C(=O)c2cc(Cc4n[nH]c(=O)c5ccccc45)ccc2F)C3)cc(OC)c1OC] |
| S24 | 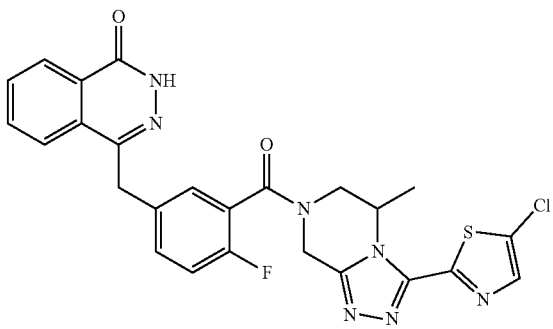 [SMILES: CC1CN(C(=O)c2cc(Cc3n[nH]c(=O)c4ccccc34)ccc2F)Cc2nnc(-c3ncc(Cl)s3)n21] |

-continued
| compound | Structure |
|---|---|
| S25 | 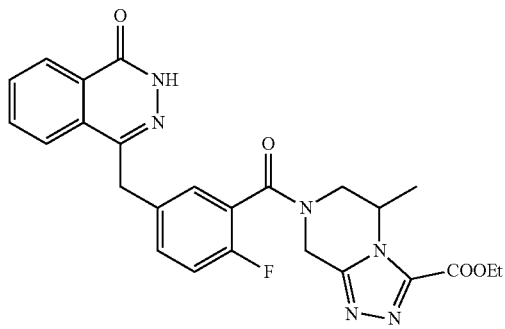 [SMILES: CCOC(=O)c1nnc2n1C(C)CN(C(=O)c1cc(Cc3n[nH]c(=O)c4ccccc34)ccc1F)C2] |
| S26 | 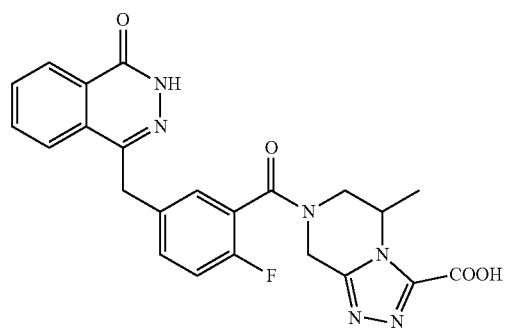 [SMILES: CC1CN(C(=O)c2cc(Cc3n[nH]c(=O)c4ccccc34)ccc2F)Cc2nnc(C(=O)O)n21] |
| S27 | 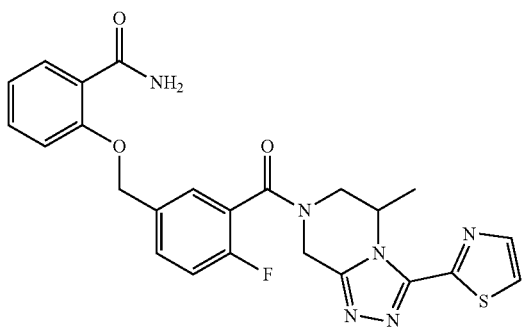 [SMILES: CC1CN(C(=O)c2cc(COc3ccccc3C(N)=O)ccc2F)Cc2nnc(-c3nccs3)n21] |
| S28 | 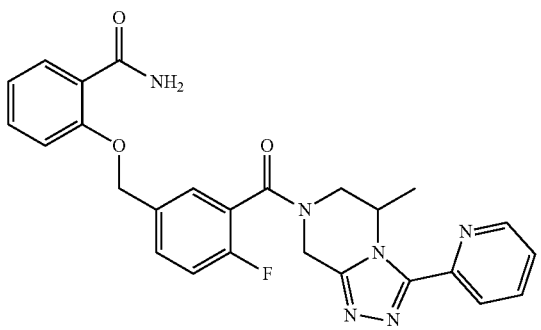 [SMILES: CC1CN(C(=O)c2cc(COc3ccccc3C(N)=O)ccc2F)Cc2nnc(-c3ccccn3)n21] |

| compound | Structure |
|---|---|
| S33 | 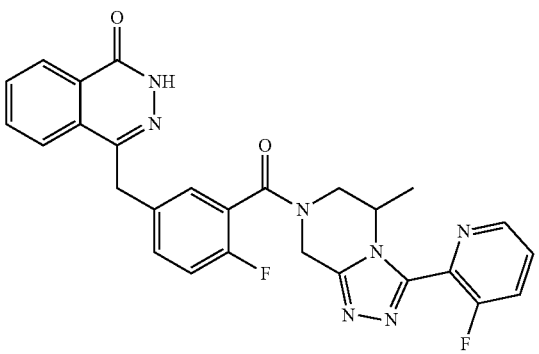 [SMILES: CC1CN(C(=O)c2cc(Cc3n[nH]c(=O)c4ccccc34)ccc2F)Cc2nnc(-c3ncccc3F)n21] |
| S34 | 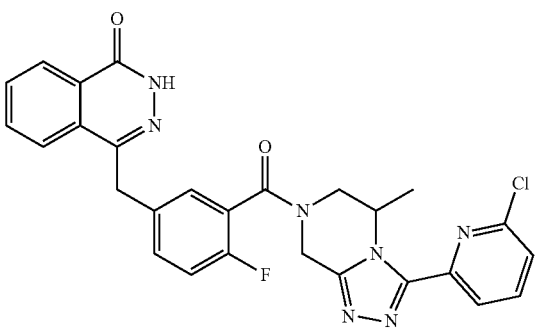 [SMILES: CC1CN(C(=O)c2cc(Cc3n[nH]c(=O)c4ccccc34)ccc2F)Cc2nnc(-c3cccc(Cl)n3)n21] |
| S35 | 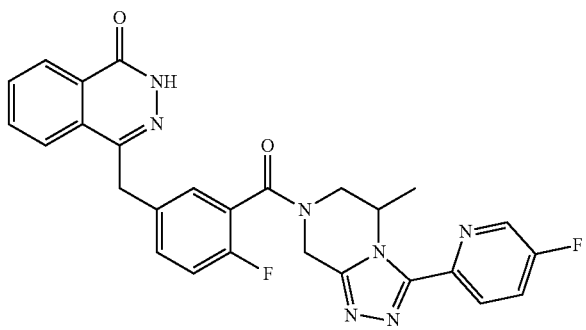 [SMILES: CC1CN(C(=O)c2cc(Cc3n[nH]c(=O)c4ccccc34)ccc2F)Cc2nnc(-c3ccc(F)cn3)n21] |
| S36 | 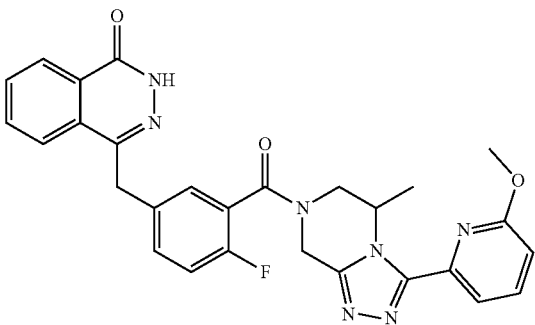 [SMILES: COc1cccc(-c2nnc3n2C(C)CN(C(=O)c2cc(Cc4n[nH]c(=O)c5ccccc45)ccc2F)C3)n1] |

| compound | Structure |
|---|---|
| S37 | 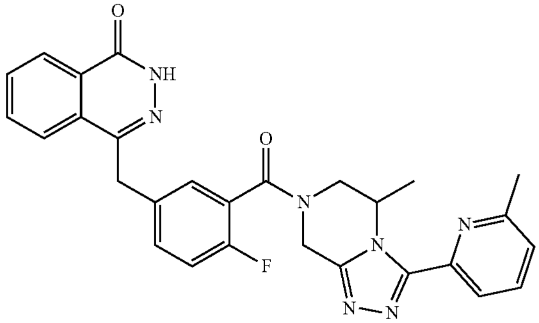 [SMILES: Cc1cccc(-c2nnc3n2C(C)CN(C(=O)c2cc(Cc4n[nH]c(=O)c5ccccc45)ccc2F)C3)n1] |
| S38 | and |
| S39 | 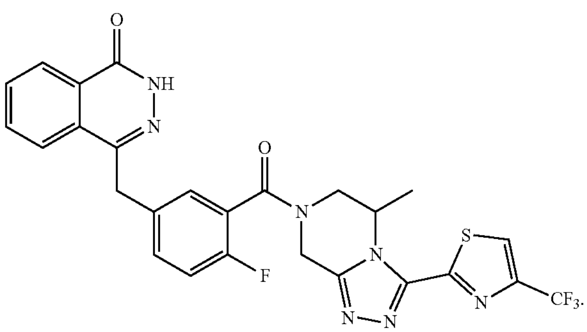 [SMILES: CC1CN(C(=O)c2cc(Cc3n[nH]c(=O)c4ccccc34)ccc2F)Cc2nnc(-c3nc(C(F)(F)F)cs3)n21] |

6. A method for preparing the substituted triazolopiperazine compound represented by formula (I) according to claim 1, the reaction route thereof is as follows:

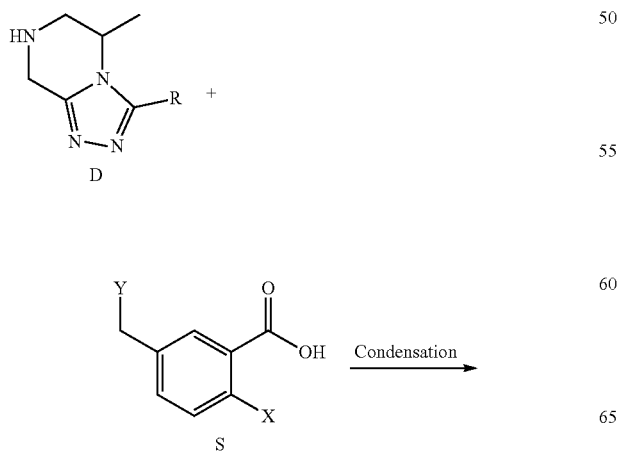

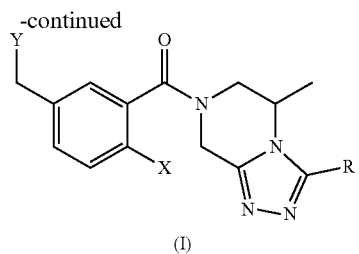

wherein the definitions of X, Y and R are defined as those in any one of claims 1 to 5;
reacting compound S with compound D via condensation reaction to give a substituted triazolopiperazine compound represented by formula (I).

7. A method of treatment of a disease associated with PARP, comprising administering a subject a therapeutically effective amount of one or more selected from the group consisting of the substituted triazolopiperazine compound represented by formula (I) according to claim 1, and a tautomer, enantiomer, diastereomer, racemate, pharmaceutically acceptable salt, ester and hydrate thereof, wherein the disease associated with PARP is one or more selected from the group consisting of breast cancer, ovarian cancer, pancreatic cancer, and colon cancer.

8. A pharmaceutical composition comprising a therapeutically effective amount of one or more selected from the group consisting of the substituted triazolopiperazine compound represented by formula (I) according to claim 1, and a tautomer, enantiomer, diastereomer, racemate, pharmaceutically acceptable salt, ester and hydrate thereof.

9. The method of claim 6, wherein the condensation reaction is performed by reacting compound S with compound D in a solvent in the presence of a condensing agent and a base;

wherein the condensing agent is selected from one or more of the group consisting of N,N'-dicyclohexylcarbodiimide, N-(3-Dimethylaminopropyl)-N'-ethylcarbodimide or hydrochloride thereof, 1,1'-carbonyldiimidazole, N,N'-diisopropylcarbodiimide, O-(1,2-dihydro-2-oxo-pyridyl)-N,N,N',N'-tetramethyluronium tetrafluoroborate, O-(benzotriazol-1-yl)-N,N,N',N'-tetramethyluronium tetrafluoroborate, O-(7-azabenzotriazol-1-yl)-N,N,N',N'-tetramethyluronium hexafluorophosphate, benzotriazole-N,N,N',N'-tetramethyluronium hexafluorophosphate, 2-(7-azabenzotriazole)-N,N,N',N'-tetramethyluronium hexafluorophosphate, O-(6-chloro-1H-benzotriazol-1-yl)-N,N,N',N'-tetramethyluronium hexafluorophosphate, benzotriazol-1-yloxytris(dimethylamino)phosphonium hexafluorophosphate and benzotriazole-1-yloxytripyrrolidinophosphonium hexafluorophosphate, wherein the base is one or more selected from the group consisting of triethylamine, diethylamine, tributylamine, tripropylamine, diisopropylamine, diisopropylethylamine, trimethylamine, pyridine, 2,6-lutidine, 4-dimethylaminopyridine, piperidine, pyrrolidine, quinoline, morpholine, N-methylmorphine, N-ethylmorpholine, N-methylpiperidine, diisopropylamine, diisopropylethylamine, 1,8-Diazabicyclo[5.4.0]undec-7-ene, and 1,5-diazabicyclo[4.3.0]-non-5-ene; and wherein the solvent is one or more selected from the group consisting of benzene, xylene, toluene, dichloromethane, chloroform, carbon tetrachloride, tetrahydrofuran, 2-methyltetrahydrofuran, ethyl ether, acetone, 1,4-dioxane, N,N-dimethylformamide, N,N-diethylformamide, N,N-dimethylacetamide, acetonitrile, and dimethyl sulfoxide.

* * * * *